US012569688B2

(12) United States Patent
Zhang et al.

(10) Patent No.: US 12,569,688 B2
(45) Date of Patent: Mar. 10, 2026

(54) MEDICAL DEVICE AND METHOD FOR DETECTING ARRHYTHMIA

(71) Applicant: Medtronic, Inc., Minneapolis, MN (US)

(72) Inventors: Xusheng Zhang, Shoreview, MN (US); Saul E. Greenhut, Denver, CO (US); Yuanzhen Liu, Palo Alto, CA (US); Alfonso Aranda Hernandez, Minneapolis, MN (US); Michael W. Heinks, New Brighton, MN (US); Jean E. Hudson, Blaine, MN (US); Timothy A. Ebeling, Circle Pines, MN (US); Irving J. Sanchez, Blaine, MN (US); Scott R. Hawkinson, Andover, MN (US); Troy E. Jackson, Rogers, MN (US); James Vander Heyden, Delano, MN (US)

(73) Assignee: Medtronic, Inc., Minneapolis, MN (US)

( * ) Notice: Subject to any disclaimer, the term of this patent is extended or adjusted under 35 U.S.C. 154(b) by 542 days.

(21) Appl. No.: 18/054,137

(22) Filed: Nov. 9, 2022

(65) Prior Publication Data

US 2023/0173279 A1     Jun. 8, 2023

Related U.S. Application Data

(60) Provisional application No. 63/286,442, filed on Dec. 6, 2021.

(51) Int. Cl.
*A61N 1/36*          (2006.01)
*A61B 5/363*         (2021.01)
(Continued)

(52) U.S. Cl.
CPC .............. *A61N 1/362* (2013.01); *A61B 5/363* (2021.01); *A61N 1/36507* (2013.01)

(58) Field of Classification Search
CPC ............... A61N 1/362; A61N 1/36507; A61N 1/3925; A61N 1/365; A61B 5/363; A61B 5/4836
See application file for complete search history.

(56) References Cited

U.S. PATENT DOCUMENTS 5,800,464 A  *  9/1998  Kieval ................. A61N 1/3622
                                                                607/9
7,194,302 B2     3/2007  Bardy et al.
                (Continued)

FOREIGN PATENT DOCUMENTS

WO        2008137536 A1    11/2008

OTHER PUBLICATIONS (PCT/US2022/061223) PCT Notification of Transmittal of the International Search Report and the Written Opinion of the International Searching Authority, Mailed Feb. 17, 2023, 9 pages.
(Continued)

*Primary Examiner* — Rex R Holmes

(57)                ABSTRACT

A medical device is configured to determine tachyarrhythmia evidence in a cardiac signal segment received from a cardiac electrical signal sensed during a pacing escape interval started to schedule a pending cardiac pacing pulse. The medical device may delay the pending cardiac pacing pulse in response to determining the tachyarrhythmia evidence during the pacing escape interval.

35 Claims, 16 Drawing Sheets

(51) Int. Cl.
    *A61N 1/362*        (2006.01)
    *A61N 1/365*        (2006.01)

(56)       References Cited

U.S. PATENT DOCUMENTS

| | | |
|---|---|---|
| 7,761,142 B2 | 7/2010 | Ghanem et al. |
| 7,761,150 B2 | 7/2010 | Ghanem et al. |
| 7,991,471 B2 | 8/2011 | Ghanem et al. |
| 8,078,277 B2 | 12/2011 | Gunderson et al. |
| 8,170,654 B1 | 5/2012 | Zhang et al. |
| 8,301,233 B2 | 10/2012 | Zhang et al. |
| 8,825,145 B1 | 9/2014 | Zhang |
| 9,002,443 B2 | 4/2015 | Zhang et al. |
| 10,130,824 B2 | 11/2018 | Grinberg et al. |
| 10,252,071 B2 | 4/2019 | Cao et al. |
| 10,328,274 B2 | 6/2019 | Zhang et al. |
| 10,448,855 B2 | 10/2019 | Reinke et al. |
| 10,556,118 B2 | 2/2020 | Anderson et al. |
| 10,561,332 B2 | 2/2020 | Zhang et al. |
| 10,675,471 B2 | 6/2020 | Zhang et al. |
| 10,675,478 B2 | 6/2020 | Marshall et al. |
| 10,799,710 B2 | 10/2020 | Cao et al. |
| 11,089,989 B2 | 8/2021 | Freed et al. |
| 11,331,035 B2 | 5/2022 | Stadler et al. |
| 2008/0269624 A1 | 10/2008 | Zhang et al. |
| 2014/0330328 A1 | 11/2014 | Christie et al. |
| 2015/0305642 A1* | 10/2015 | Reinke .................. A61B 5/686 |
| | | 600/510 |
| 2019/0308026 A1 | 10/2019 | Zhang et al. |

OTHER PUBLICATIONS

Greenhut et al., U.S. Appl. No. 63/251,803, entitled "Medical Device and Method for Cardiac Pacing and Sensing," filed Oct. 4, 2021, 123 pages.

Greenhut et al., U.S. Appl. No. 63/251,820, entitled "Medical Device and Method for Cardiac Pacing and Sensing," filed Oct. 4, 2021, 147 pages.

Greenhut et al., U.S. Appl. No. 17/822,681, entitled "Medical Device and Method for Cardiac Pacing and Sensing," filed Aug. 26, 2022, 177 pages.

Liu et al., U.S. Appl. No. 63/250,535, entitled "Medical Device and Method for Detecting Tachyarrhythmia," filed Sep. 30, 2021, 129 pages.

Liu et al., U.S. Appl. No. 17/823,055, entitled "Medical Device and Method for Detecting Tachyarrhythmia," filed Aug. 29, 2022, 135 pages.

Aranda Hernandez et al., U.S. Appl. No. 63/278,955, entitled "Medical Device and Method for Detecting Arrhythmia," filed Nov. 12, 2021, 123 pages.

Aranda Hernandez et al., U.S. Appl. No. 18/045,135, entitled "Medical Device and Method for Detecting Arrhythmia," filed Oct. 7, 2022, 126 pages.

* cited by examiner

250

260

270

350

355

MEDICAL DEVICE AND METHOD FOR DETECTING ARRHYTHMIA

REFERENCE TO RELATED APPLICATION

This application claims the benefit of provisional U.S. Patent Application No. 63/286,442, filed on Dec. 6, 2021, incorporated herein by reference in its entirety.

TECHNICAL FIELD

The disclosure relates generally to a medical device and method for sensing cardiac signals and detecting arrhythmia.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. The medical device may sense cardiac electrical signals from a heart chamber and deliver electrical stimulation therapies to the heart chamber using electrodes carried by a transvenous medical electrical lead that positions electrodes within the patient's heart.

A cardiac pacemaker or cardioverter defibrillator may deliver therapeutic electrical stimulation to the heart via electrodes carried by one or more medical electrical leads coupled to the medical device. The electrical stimulation may include signals such as pacing pulses and/or cardioversion or defibrillation shocks. In some cases, a medical device may sense cardiac electrical signals attendant to the intrinsic depolarizations of the myocardium and control delivery of stimulation signals to the heart based on sensed cardiac electrical signals. Cardiac signals sensed within a heart chamber using endocardial electrodes carried by transvenous leads, for example, generally have a high signal strength and quality for reliably sensing cardiac electrical events, such as ventricular R-waves sensed from within a ventricle. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia and may deliver anti-tachycardia pacing (ATP) and/or cardioversion or defibrillation (CV/DF) shocks to the heart upon detecting tachycardia or fibrillation.

SUMMARY

In general, this disclosure is directed to a medical device and techniques for detecting arrhythmias and controlling the delivery of cardiac pacing pulses based on detected arrhythmias. In some examples, the medical device may be coupled to extracardiac medical leads carrying electrodes positioned outside the heart for sensing cardiac electrical signals and delivering electrical stimulation pulses, including cardiac pacing pulses and/or CV/DF shocks. A medical device operating according to the techniques disclosed herein is configured to schedule a cardiac pacing pulse and, prior to pacing pulse delivery, analyze a cardiac electrical signal to verify that ventricular tachyarrhythmia (VT) or ventricular fibrillation (VF) are not present in the signal in order to minimize the likelihood of delivering a cardiac pacing pulse during VT or VF. When evidence of VT or VF (VT/VF) is detected in a cardiac electrical signal received by the medical device during a time interval preceding a scheduled pacing pulse, the medical device may delay or cancel a scheduled cardiac pacing pulse. Evidence of VT/VF may be a morphology metric of the amplitude, slope content and/or frequency content of a time segment of the cardiac electrical signal that meets a threshold or corresponds to an expected value or range of the morphology metric during a VT/VF rhythm.

The medical device may be configured to schedule a bradycardia pacing pulse by starting a pacing escape interval in response to sensing a ventricular event signal, e.g., an R-wave, or when a pacing pulse is delivered. The scheduled pacing pulse may be delivered when the pacing escape interval expires if another ventricular event signal is not sensed during the pacing escape interval. Prior to delivering the scheduled pacing pulse, however, the medical device may analyze a cardiac electrical signal to verify that a VT/VF rhythm is unlikely to be occurring. When VT/VF evidence is not present in the cardiac electrical signal, the scheduled pacing pulse can be delivered. When VT/VF evidence is determined from the cardiac electrical signal prior to the scheduled time of the pacing pulse, the medical device may delay the scheduled pacing pulse.

In one example, the disclosure provides a medical device including a sensing circuit configured to sense at least one cardiac electrical signal, a therapy delivery circuit configured to deliver cardiac pacing pulses, and a control circuit in communication with the sensing circuit and the therapy delivery circuit. The control circuit may be configured to schedule a pending pacing pulse by starting a first pacing escape interval, receive a first cardiac signal segment from the at least one cardiac electrical signal sensed by the sensing circuit during the first pacing escape interval, determine tachyarrhythmia evidence in the first cardiac signal segment, and delay the pending pacing pulse scheduled at an expiration of the first pacing escape interval in response to determining the tachyarrhythmia evidence in at least the first cardiac signal segment.

In another example, the disclosure provides a method that includes sensing at least one cardiac electrical signal, scheduling a pending pacing pulse by starting a first pacing escape interval, receiving a first cardiac signal segment from the at least one cardiac electrical signal sensed during the first pacing escape interval, determining tachyarrhythmia evidence in the first cardiac signal segment, and delaying the pending pacing pulse scheduled at an expiration of the first pacing escape interval in response to determining the tachyarrhythmia evidence in at least the first cardiac signal segment.

In another example, the disclosure provides a non-transitory computer-readable medium storing a set of instructions which, when executed by a control circuit of a medical device, cause the medical device to sense at least one cardiac electrical signal, schedule a pending pacing pulse by starting a pacing escape interval, receive a cardiac signal segment from the at least one cardiac electrical signal sensed during the pacing escape interval, determine tachyarrhythmia evidence in the cardiac signal segment, and delay the pending pacing pulse scheduled at an expiration of the pacing escape interval in response to determining the tachyarrhythmia evidence in at least the cardiac signal segment.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
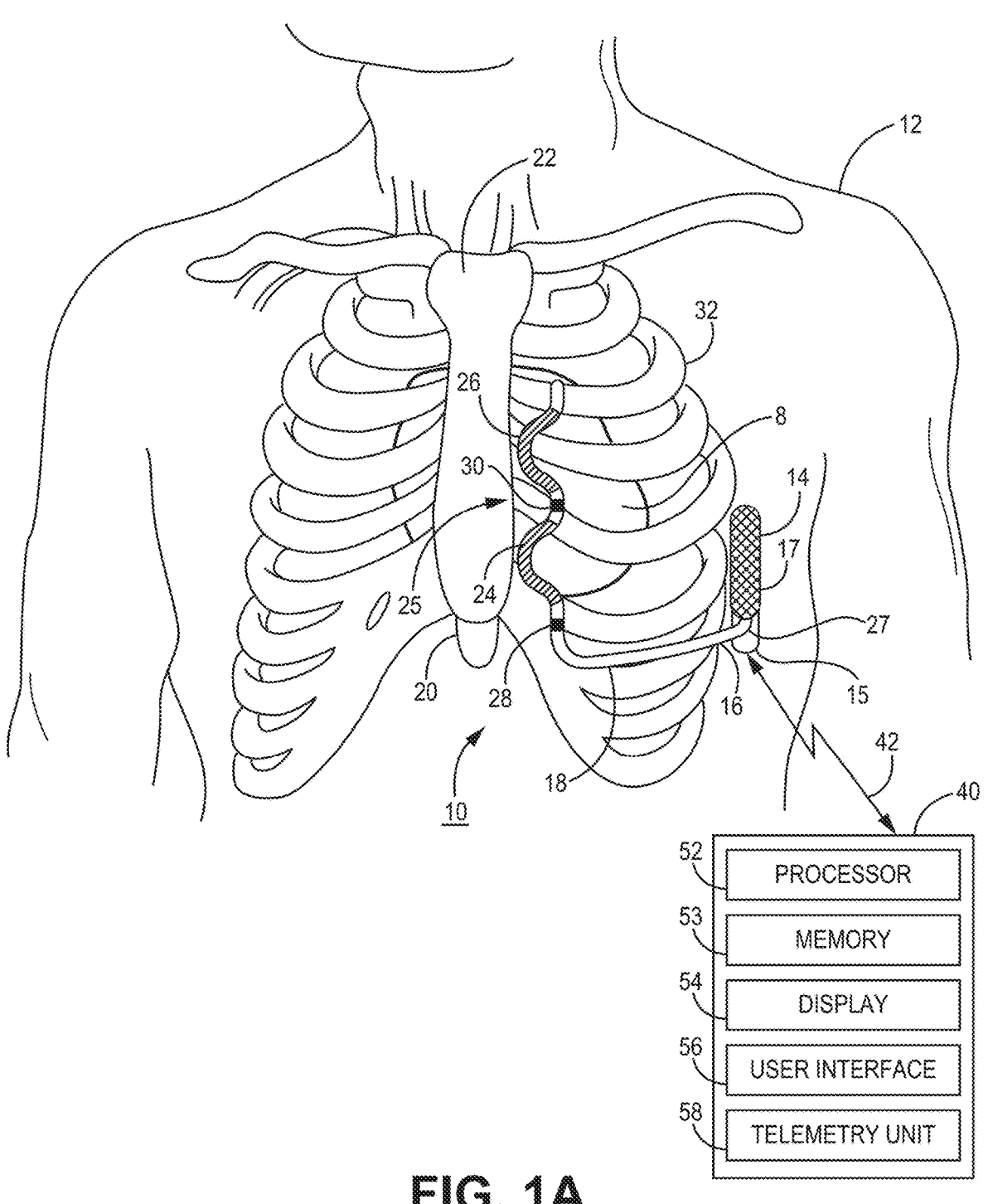
FIGS. 1A and 1B are conceptual diagrams of one example of an ICD system that may be configured to sense cardiac event signals, detect arrhythmia and deliver electrical stimulation therapy according to the techniques disclosed herein.

In general, this disclosure describes a medical device and techniques for detecting arrhythmia and delivering electrical stimulation therapy for treating arrhythmia. In various examples, the medical device performing the techniques disclosed herein may be included in an ICD capable of sensing cardiac electrical signals, detecting arrhythmia based on an analysis of the sensed cardiac electrical signals, and delivering electrical stimulation therapy for treating the arrhythmia. In some examples, the ICD is coupled to an extra-cardiovascular lead. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. In other examples, a transvenous extra-cardiac lead may carry implantable electrodes that can be positioned intravenously but outside the heart in an extra-cardiac location, e.g., within the internal thoracic vein, jugular vein, or other vein, for sensing cardiac electrical signals and delivering cardiac pacing pulses.

As disclosed herein, a medical device capable of delivering cardiac pacing pulses is configured to analyze at least one time segment of a cardiac electrical signal that is sensed during a pacing escape interval, prior to delivering a pending cardiac pacing pulse. The cardiac electrical signal segment is analyzed by the medical device for determining evidence of VT/VF. The pending cardiac pacing pulse may be delayed or cancelled when evidence of VT/VF is determined. Multiple segments of the cardiac electrical signal may be analyzed for delaying a pending cardiac pacing pulse multiple times when evidence of VT/VF is determined from the multiple time segments. When criteria for determining evidence of VT/VF are not met, a pending pacing pulse may be delivered, which may be after one or more delays. The pending pacing pulse that is delayed due to determination of VT/VF evidence may be delivered after a maximum allowable pacing delay when VT/VF is not detected by the medical device during the maximum pacing delay. Various techniques for controlling cardiac pacing pulse delivery to avoid starting cardiac pacing during undetected VT/VF are described herein in conjunction with the various flow charts and diagrams. Various techniques are also described herein for delaying or terminating cardiac pacing when a VT/VF rhythm is present or VT/VF onset occurs after cardiac pacing at a given rate has already started.

It is noted that determination of VT/VF evidence in a cardiac electrical signal for controlling cardiac pacing for treating bradycardia or asystole may be distinct from detecting VT/VF for controlling tachyarrhythmia therapy delivery. Cardiac signal processing and analysis for determining VT/VF evidence for delaying or cancelling a pending pacing pulse does not require detection of a VT/VF rhythm. The VT/VF evidence determined in a cardiac signal segment may be insufficient evidence for detecting VT/VF but may be sufficient evidence to warrant delaying a cardiac pacing pulse as a precaution against pacing during a VT/VF rhythm that may have started but is not yet detected by the medical device. Determination of VT/VF evidence therefore may not cause the medical device to deliver a tachyarrhythmia therapy, such as an ATP therapy or CV/DF shock but may cause the medical device to delay delivery of cardiac pacing pulses to enable VT/VF detection without interference of bradycardia pacing pulses. In this way, a prolonged delay in detecting a potential underlying VT/VF rhythm due brady-cardia pacing interference is avoided. If VT/VF is subse-quently detected by the medical device according to tach-yarrhythmia detection algorithm(s) during cardiac pacing that is being delivered for treating bradycardia or asystole, before or after delaying a pending cardiac pacing pulse one or more times, the cardiac pacing may be terminated, e.g., by cancelling a pending pacing pulse without restarting a pacing escape interval. The medical device may prepare for delivering a tachyarrhythmia therapy.

Figure 1B:
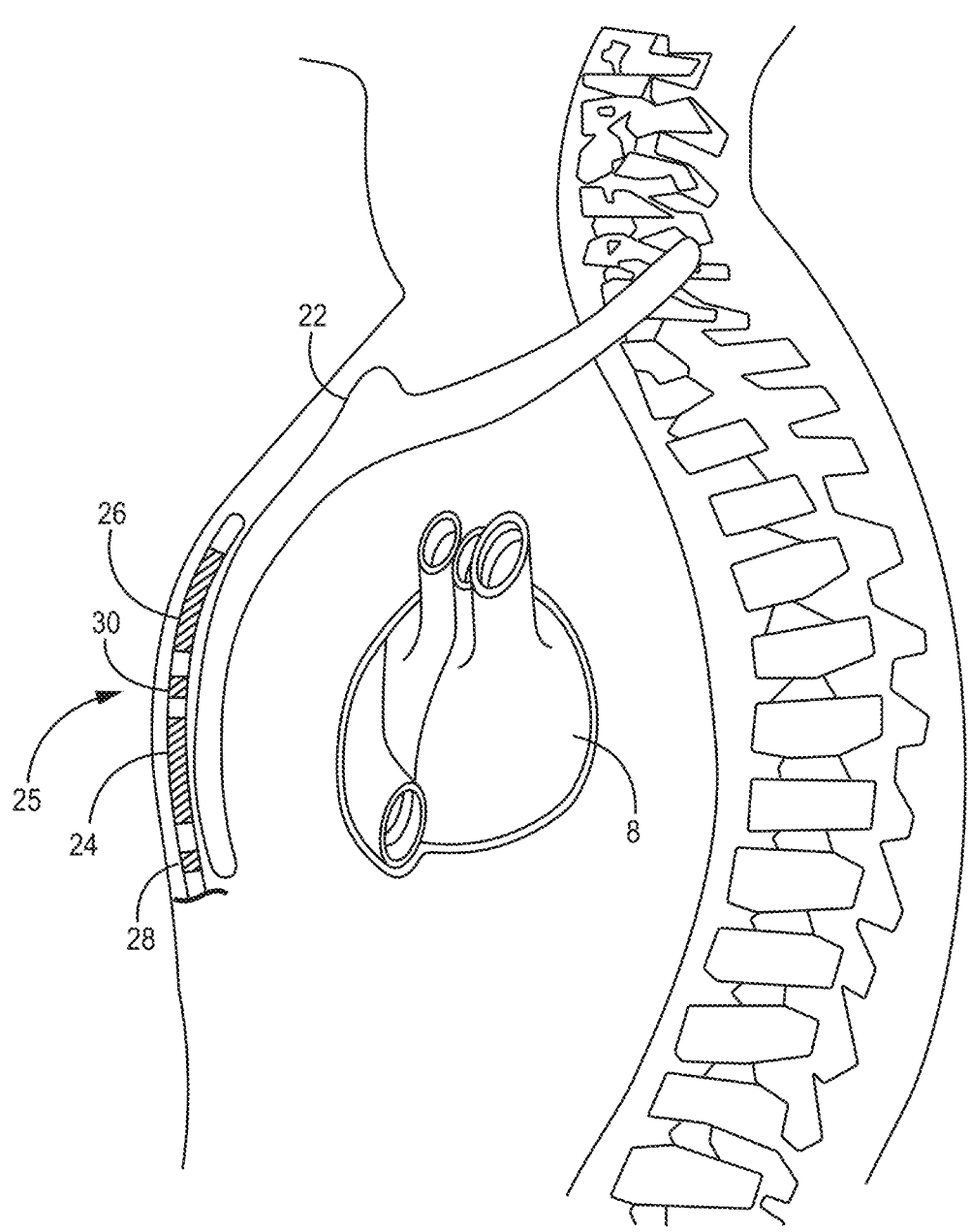

FIGS. 1A and 1B are conceptual diagrams of one example of an ICD system 10 that may be configured to sense cardiac electrical signals, detect arrhythmia and deliver electrical stimulation therapy according to the techniques disclosed herein. FIG. 1A is a front view of ICD system 10 implanted within patient 12. FIG. 1B is a side view of ICD system 10 implanted within patient 12. ICD system 10 includes an ICD 14 connected to an electrical stimulation and sensing lead 16, positioned in an extra-cardiovascular location in this example. FIGS. 1A and 1B are described in the context of an ICD system 10 capable of providing high voltage CV/DF shocks and/or cardiac pacing pulses in response to detecting a cardiac arrhythmia based on processing of sensed cardiac electrical signals. The techniques disclosed herein for sens-ing cardiac electrical signals and detecting arrhythmia may be implemented in a variety of medical devices including external or implantable cardiac monitors, pacemakers, and ICDs.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, relatively lower voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical con-nections between conductors extending within the lead body 18 of lead 16 and electronic components included within the housing 15 of ICD 14. As will be described in further detail herein, housing 15 may house one or more processing circuits, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrilla-tion electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated indepen-dently.

Electrodes 24 and 26 (and in some examples housing 15) are referred to herein as defibrillation electrodes because they are utilized, individually or collectively, for delivering high voltage stimulation therapy (e.g., CV/DF shocks). Electrodes 24 and 26 may be elongated coil electrodes and generally have a relatively high surface area for delivering high voltage electrical stimulation pulses compared to pac-ing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing electrode vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to deliver-ing high voltage CV/DF shocks. In some instances, elec-trodes 28 and 30 may provide only pacing functionality, only sensing functionality or both.

ICD 14 may obtain cardiac electrical signals correspond-ing to electrical activity of heart 8 via a combination of sensing electrode vectors that include combinations of elec-trodes 24, 26, 28 and/or 30. In some examples, housing 15 of ICD 14 is used in combination with one or more of electrodes 24, 26, 28 and/or 30 in at least one sensing electrode vector. Various sensing electrode vectors utilizing combinations of electrodes 24, 26, 28, and 30 and/or housing 15 are described below for sensing one or more cardiac electrical signals. Each cardiac electrical signal that is sensed by ICD 14 may be sensed using a different sensing electrode vector, which may be selected by sensing circuitry included in ICD 14. The cardiac electrical signal(s) received via a selected sensing electrode vector may be used by ICD 14 for sensing cardiac event signals attendant to intrinsic depolarizations of the myocardium, e.g., R-waves attendant to ventricular depolarization and in some cases P-waves attendant to atrial depolarization. Sensed cardiac event sig-nals may be used for determining the heart rate and deter-mining a need for cardiac pacing, e.g., for treating brady-cardia or asystole for preventing a long ventricular pause or delivering a post-shock pacing pulse. Sensed cardiac event signals may also be used for detecting a VT/VF rate and a need for tachyarrhythmia therapies, e.g., anti-tachycardia pacing (ATP) or CV/DF shocks.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit electrical stimulation pulses from a therapy delivery circuit within ICD 14 to one or more of defibrillation electrodes 24 and 26 and/or pace/sense electrodes 28 and 30 and transmit electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in U.S. Pat. No. 10,675,478 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signal(s) received from one or more sensing electrode vectors to monitor for abnormal rhythms, such as asystole, bradycardia, VT and/or VF. ICD 14 may analyze the heart rate and/or morphology of the cardiac electrical signals to monitor for tachyarrhythmia in accordance with tachyarrhythmia detection techniques. ICD 14 generates and delivers electrical stimulation therapy in response to detecting a tachyarrhythmia, e.g., VT/VF, using a therapy delivery electrode vector which may be selected from any of the available electrodes 24, 26, 28 30 and/or housing 15. ICD 14 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

In the absence of a ventricular event signal, ICD 14 may generate and deliver a cardiac pacing pulse, such as a post-shock pacing pulse or bradycardia pacing pulse when asystole is detected or when a pacing escape interval expires prior to sensing a ventricular event signal, e.g., when AV block is present. The cardiac pacing pulses may be delivered using a pacing electrode vector that includes one or more of the electrodes 24, 26, 28, and 30 and the housing 15 of ICD 14. As described below, ICD 14 may analyze a time segment of a cardiac electrical signal sensed prior to delivering a pending cardiac pacing pulse for verifying that VT/VF is not occurring before delivering the pending pacing pulse. A VT/VF rhythm that has started may not yet be detected by ICD 14 if VT/VF detection criteria have not yet been met. For example, in some instances a VT/VF rhythm onset may occur before or after a pacing pulse is scheduled, but the VT/VF is not yet detected according to VT/VF detection algorithms. In other examples, a VT/VF rhythm may be undersensed, e.g., due to low amplitude or variable amplitude R-waves and/or fibrillation waves. Undersensing of the ventricular event signals could result in delivery of a pacing pulse for treating bradycardia or asystole during an actual VT/VF rhythm, when tachyarrhythmia therapy is actually needed. Pacing during undersensed or undetected VT/VF is undesirable because it may further confound detection of the VT/VF rhythm by ICD 14, accelerate an ongoing tachyarrhythmia, and/or delay or preclude appropriate tachyarrhythmia therapy delivery, e.g., ATP or CV/DF shock therapy, when VT/VF is occurring. According to techniques disclosed herein, ICD 14 may delay or withhold a pending cardiac pacing pulse when VT/VF evidence is determined in one or more cardiac signal segments in order to minimize the likelihood of pacing during VT/VF. In some instances, VT/VF detection criteria may be met when cardiac pacing is being withheld such that a pending cardiac pacing pulse may be cancelled and a tachyarrhythmia therapy may be delivered instead.

In FIG. 1A, ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting in the practice of the techniques disclosed herein.

A medical device operating according to techniques disclosed herein may be coupled to a transvenous or non-transvenous lead in various examples for carrying electrodes for sensing cardiac electrical signals and delivering electrical stimulation therapy. For example, the medical device, such as ICD 14, may be coupled to an extra-cardiovascular lead as illustrated in the accompanying drawings, referring to a lead that positions electrodes outside the blood vessels, heart, and pericardium surrounding the heart of a patient. Implantable electrodes carried by extra-cardiovascular leads may be positioned extra-thoracically (outside the ribcage and sternum), subcutaneously or submuscularly, or intra-thoracically (beneath the ribcage or sternum, sometimes referred to as a sub-sternal position) and may not necessarily be in intimate contact with myocardial tissue. An extra-cardiovascular lead may also be referred to as a "non-transvenous" lead.

In other examples, the medical device may be coupled to a transvenous lead that positions electrodes within a blood vessel, which may remain outside the heart in an "extra-cardiac" location or be advanced to position electrodes within a heart chamber. For instance, a transvenous medical lead may be advanced along a venous pathway to position electrodes in an extra-cardiac location within the internal thoracic vein (ITV), an intercostal vein, the superior epigastric vein, or the azygos, hemiazygos, or accessory hemi-azygos veins, as examples. In still other examples, a transvenous lead may be advanced to position electrodes within the heart, e.g., within an atrial and/or ventricular heart chambers.

An external device 40 is shown in telemetric communication with ICD 14 by a wireless communication link 42 in FIG. 1A. External device 40 may include a processor 52, memory 53, display 54, user interface 56 and telemetry unit 58. Processor 52 controls external device operations and processes data and signals received from ICD 14. Display unit 54, which may include a graphical user interface, displays data and other information to a user for reviewing ICD operation and programmed parameters as well as cardiac electrical signals retrieved from ICD 14.

User interface 56 may include a mouse, touch screen, keypad or the like to enable a user to interact with external device 40 to initiate a telemetry session with ICD 14 for retrieving data from and/or transmitting data to ICD 14, including programmable parameters for controlling cardiac event signal sensing, arrhythmia detection and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, battery status, and histories of detected rhythm episodes and delivered therapies, etc., may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or handheld device. External device 40 may be used to program cardiac signal sensing parameters, cardiac rhythm detection parameters and therapy control parameters used by ICD 14. At least some control parameters used in sensing cardiac event signals, detecting arrhythmias, controlling tachyarrhythmia therapy and for determining VT/VF evidence and controlling bradycardia pacing pulses according to the techniques disclosed herein may be programmed into ICD 14 using external device 40 in some examples.

Figure 2A:
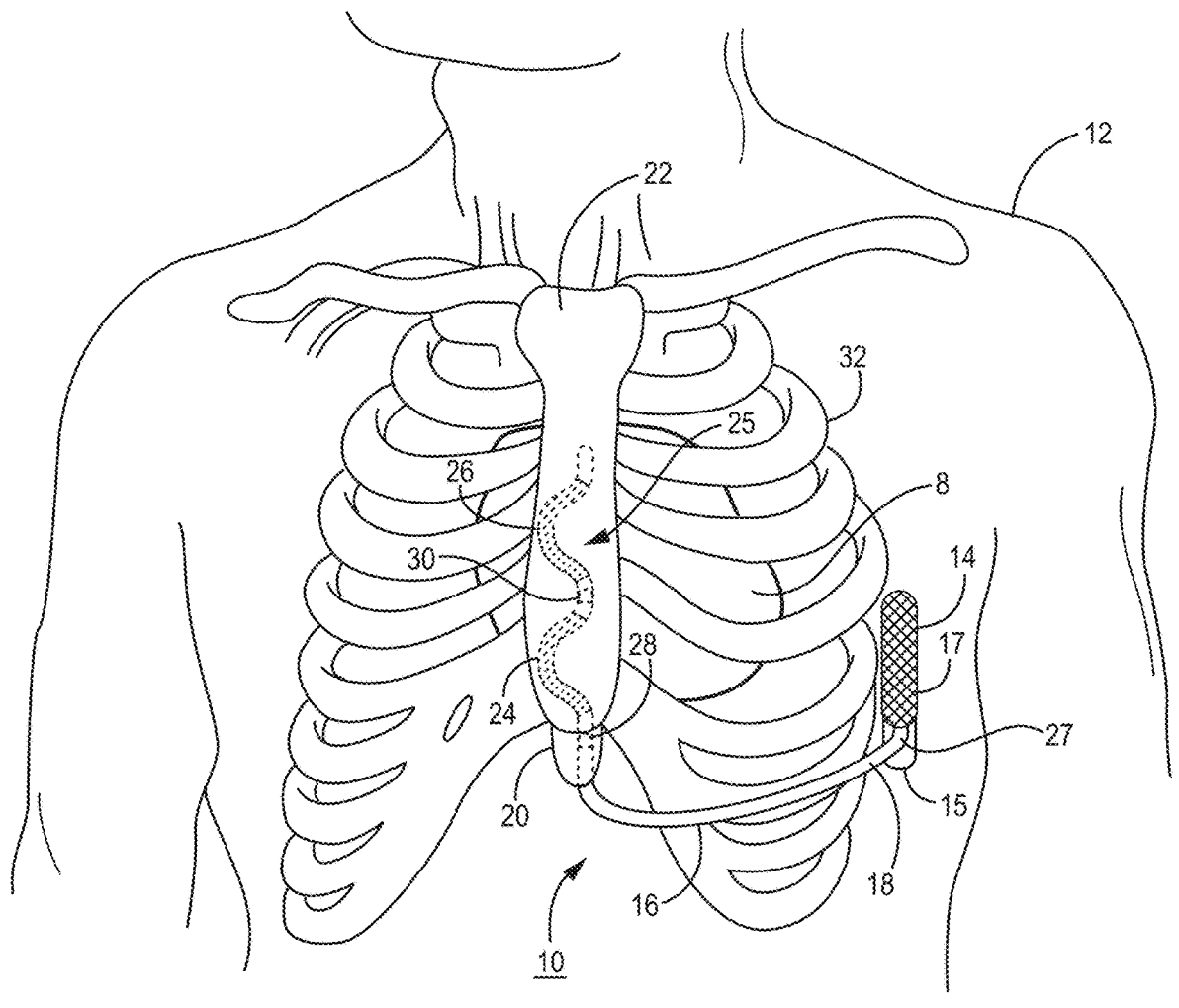
FIGS. 2A-2C are conceptual diagrams of a patient implanted with an ICD system in a different implant configuration than the arrangement shown in FIGS. 1A-1B.
Figure 2B:
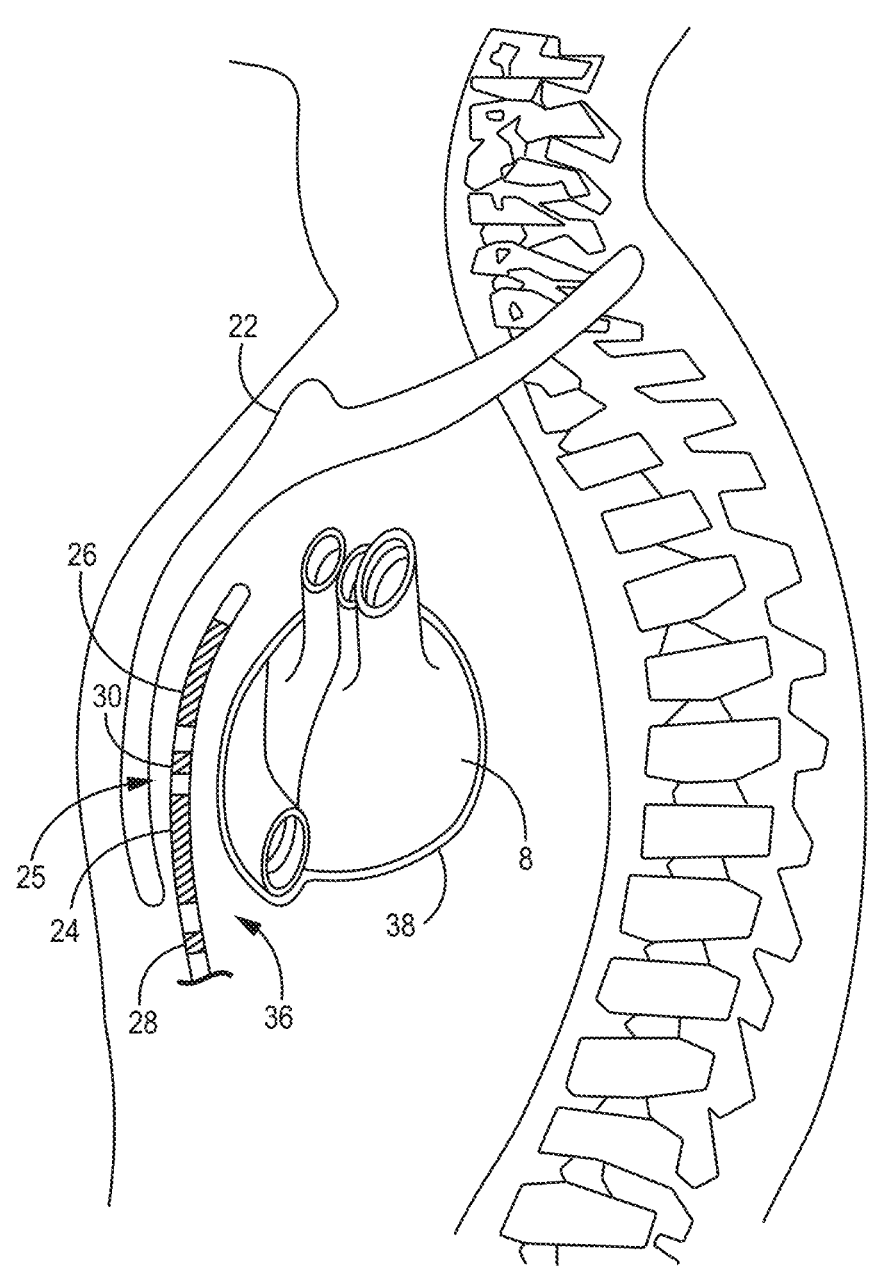
Figure 2C:
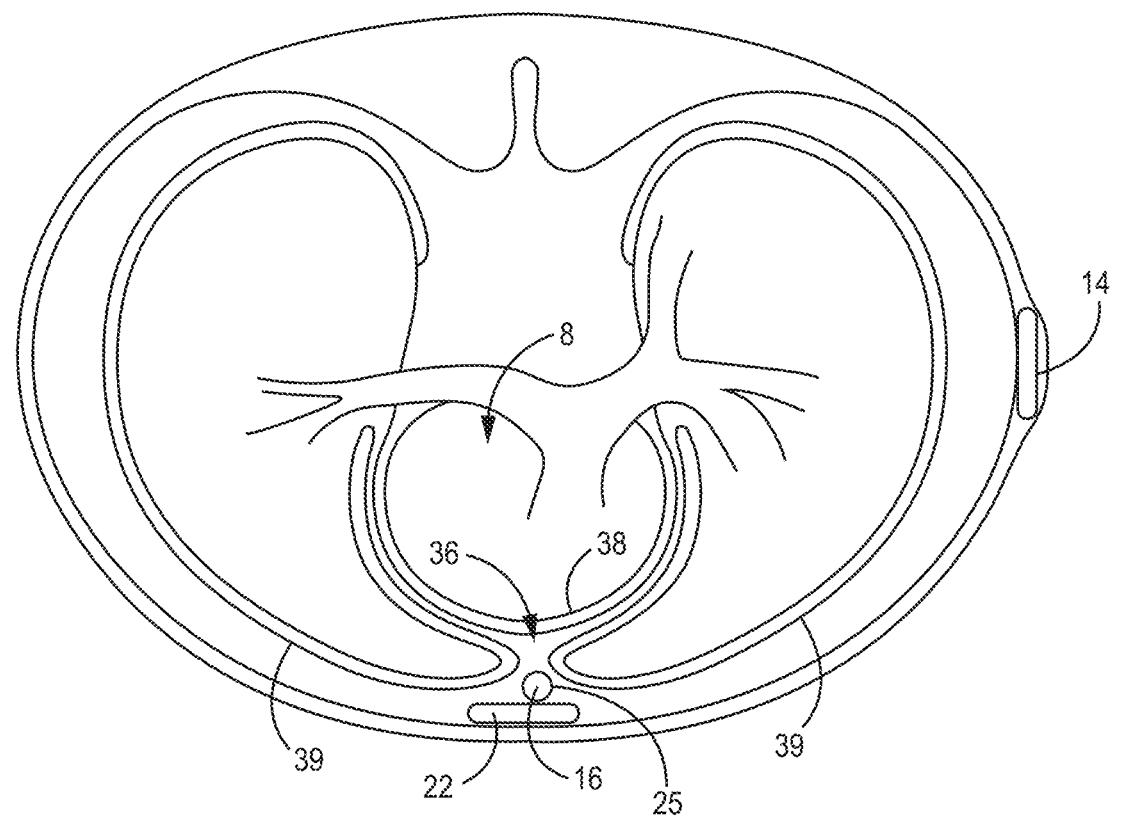

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 (see FIG. 2C) in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiac, intra-thoracic locations, including in the pleural cavity or around the perimeter of and adjacent to the pericardium 38 of heart 8.

In the various example implant locations of lead 16 and electrodes 24, 26, 28 and 30 shown and described herein, cardiac signals sensed by ICD 14 may have a relatively low and/or variable signal strength, e.g., caused by postural changes, respiration or other body movement, and/or may be contaminated by skeletal muscle myopotentials and/or environmental EMI. Undersensing of R-waves or fibrillation waves may result in an undetected tachyarrhythmia when ATP or CV/DF therapy may be needed and may result in delivery of cardiac pacing pulses during undetected VT/VF. In some cases, the onset of a VT/VF episode may occur during cardiac pacing at a programmed pacing rate such that cardiac pacing pulse delivery may interfere with VT/VF detection. Techniques disclosed herein provide improvements in controlling cardiac pacing pulse delivery to avoid initiating cardiac pacing during an undetected or undersensed VT/VF episode and to terminate cardiac pacing when a VT/VF episode begins after cardiac pacing at a programmed (or variable) pacing rate is already ongoing.

Figure 3:
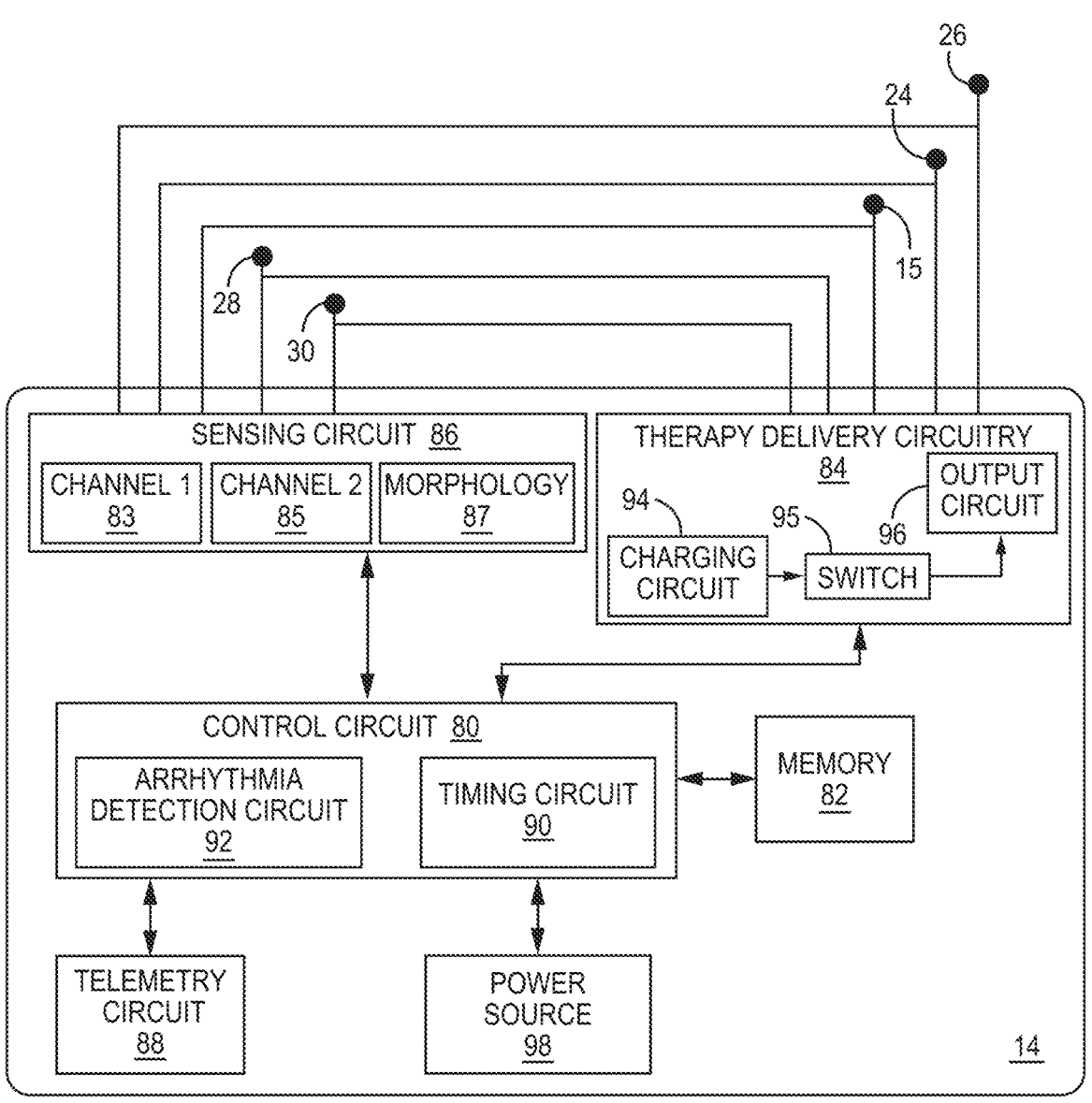
FIG. 3 is a conceptual diagram of an ICD according to one example.

FIG. 3 is a conceptual diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to a lead, such as lead 16 carrying electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3 but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware and/or software components, or integrated within common hardware, firmware and/or software components. For example, cardiac electrical signal sensing and analysis for detecting arrhythmia may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 may include hardware configured to perform subroutines of signal processing and analysis techniques disclosed herein to reduce the processing burden associated with firmware and/or software execution of processing routines. For example, hardware subroutines (HSRs) may be implemented in control circuit 80 to perform specific processing functions such as dedicated math operations, which may include any of sum, absolute value, difference, extrema, histogram counts, signal filtering (e.g., biquad filter, difference filter or other filters), etc. These HSRs could be called by control circuit firmware or software when processing and analyzing a cardiac signal for detecting arrhythmia, which may include a low pass filter, difference filter, gradient filter or other signal processing. HSRs may be called when control circuit 80 is determining various morphology parameters from a cardiac signal for determining evidence of VT/VF in a cardiac electrical signal sensed prior to the time of a scheduled pacing pulse, which may include any of a mean period, spectral width, low slope content, signal pulse amplitudes, signal pulse intervals, etc. These HSRs can unload the processing burden associated with firmware and/or software processing to reduce current drain of power source 98 and thereby extend the useful life of ICD 14.

The various circuits of ICD 14 may include an application specific integrated circuit (ASIC), an electronic circuit, a processor (shared, dedicated, or group) and memory that execute one or more software or firmware programs, a combinational logic circuit, state machine, HSR, or other suitable components or combinations of components that provide the described functionality. The particular form of software, hardware and/or firmware employed to implement the functionality disclosed herein will be determined primarily by the particular system architecture employed in the ICD and by the particular sensing, detection and therapy delivery methodologies employed by the ICD. Providing software, hardware, and/or firmware to accomplish the described functionality in the context of any modern medical device system, given the disclosure herein, is within the abilities of one of skill in the art.

Memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical signals, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally or alternatively be selectively coupled to defibrillation electrodes 24 and/or 26 for use in a sensing electrode vector together or in combination with one or more of electrodes 28, 30 and/or housing 15. Sensing circuit 86 may be enabled to receive cardiac electrical signals from at least one sensing electrode vector selected from the available electrodes 24, 26, 28, 30, and housing 15 in some examples. At least two, three or more cardiac electrical signals from two, three or more different sensing electrode vectors may be received simultaneously by sensing circuit 86 in some examples. Sensing circuit 86 may monitor one or more cardiac electrical signals for sensing cardiac event signals, e.g., R-waves attendant to intrinsic ventricular myocardial depolarizations.

In the example shown, sensing circuit 86 can monitor two cardiac electrical signals simultaneously for sensing cardiac event signals. Sensing circuit 86 may include switching circuitry for selecting which of electrodes 24, 26, 28, 30, and housing 15 are coupled as a first sensing electrode vector to a first sensing channel 83 for receiving a first cardiac electrical signal, which electrodes are coupled as a second sensing electrode vector to a second sensing channel 85 of sensing circuit 86 for receiving a second cardiac electrical signal, and which electrodes are coupled as a third sensing electrode vector to a morphology signal channel 87 for receiving a third cardiac electrical signal. Each sensing channel 83 and 85 may be configured to amplify, filter and digitize the cardiac electrical signal received from selected electrodes coupled to the respective sensing channel to improve the signal quality for sensing cardiac event signals, such as R-waves, by cardiac event detection circuitry within the respective sensing channel. The cardiac event detection circuitry within sensing circuit 86 may include one or more sense amplifiers, filters, rectifiers, threshold detectors, comparators, analog-to-digital converters (ADCs), timers or other analog and/or digital components as described further in conjunction with FIG. 4. A cardiac event sensing threshold may be automatically adjusted by each sensing channel 83 and 85 under the control of control circuit 80, based on sensing threshold control parameters, such as various timing intervals and sensing threshold amplitude values that may be determined by control circuit 80, stored in memory 82, and/or controlled by hardware, firmware and/or software of control circuit 80 and/or sensing circuit 86.

First sensing channel 83 and second sensing channel 85 may each control a cardiac event sensing threshold, e.g., an R-wave sensing threshold, that is applied to the incoming cardiac electrical signal for sensing cardiac event signals, e.g., R-waves. Upon sensing a cardiac event signal based on a sensing threshold crossing, first sensing channel 83 may produce a sensed event signal that is passed to control circuit 80. For example, upon detecting an R-wave sensing threshold crossing by the cardiac electrical signal received via a first sensing electrode vector, the first sensing channel 83 may generate a ventricular sensed event (Vsense) signal that is passed to control circuit 80. Similarly, upon detecting an R-wave sensing threshold crossing by a second cardiac electrical signal received by second sensing channel 85, the second sensing channel 85 may generate a Vsense signal that is passed to control circuit 80. The first and second sensing channels 83 and 85 may be configured to automatically adjust the R-wave sensing threshold used by each channel separately. The Vsense signals and relative timing from each other may be used by control circuit 80 for determining sensed event intervals for use in controlling bradycardia pacing and for detecting tachyarrhythmia.

In some examples, control circuit 80 is configured to identify Vsense signals as valid event signals or invalid event signals based on the relative timing of Vsense signals received from the two sensing channels 83 and 85 and/or morphology analysis of a cardiac electrical signal received from sensing circuit 86. Control circuit 80 may schedule pending pacing pulses in response to Vsense signals determined to be valid event signals. Techniques for identifying valid event signals based on Vsense signals received from two sensing channels and scheduling pacing pulses controlling the timing of bradycardia pacing pulses based on identification of valid event signals are generally disclosed in provisional U.S. Patent Application No. 63/251,803 (Greenhut, et al.), provisional U.S. Patent Application No. 63/251,820 (Greenhut, et al.) and corresponding U.S. patent application Ser. No. 17/822,681 (Greenhut, et al.), the entire content of all of which is incorporated herein by reference. The techniques disclosed herein for delaying or terminating bradycardia pacing pulses based on determining VT/VF evidence in a cardiac electrical signal sensed during a pacing escape interval may be used in conjunction with the cardiac event sensing and pacing control techniques disclosed in the above-incorporated '803 reference, '820 and '681 references. However, it is to be understood that the techniques disclosed herein may be combined with any method used for sensing ventricular signals, e.g., R-waves, and scheduling a pending cardiac pacing pulse for treating bradycardia, asystole or avoiding a long ventricular pause.

Vsense signals received from sensing circuit 86 by control circuit 80 can be used by control circuit 80 for determining sensed event intervals, which are referred to herein as RR intervals (RRIs). An RRI is the time interval between two Vsense signals received by control circuit 80 from the same sensing channel 83 or 85, which may also be referred to as an "in-channel" sensed event interval. Control circuit 80 may include a timing circuit 90 for determining RRIs between consecutive Vsense signals received from a given sensing channel 83 or 85. In some instances, when a Vsense signal is received following a delivered pacing pulse, the RRI is determined from the delivered pacing pulse to the Vsense signal. As such, RRIs may include time intervals between consecutive ventricular sensed event signals and intervals between a delivered pacing pulse and a ventricular sensed event signal. Control circuit 80 may detect VT/VF in some examples based at least in part on RRIs.

Illustrative techniques disclosed herein are described in conjunction with sensing circuit 86 configured to receive two different cardiac electrical signals by the two cardiac event sensing channels 83 and 85 for sensing R-waves from the two cardiac electrical signals and for receiving a third cardiac electrical signal by morphology signal channel 87 for passing a digitized electrocardiogram (ECG) signal to control circuit 80 for morphology analysis. The three cardiac electrical signals sensed by sensing circuit 86 may be received using three different sensing electrode vectors selected from the available electrodes 24, 26, 28 and 30 and housing 15. In other examples, two cardiac electrical signals may be received by sensing circuit 86 from two different sensing electrode vectors, with one signal passed to the first sensing channel 83 and the other signal passed to the second sensing channel 85. Either or both of the two signals may be passed to control circuit 80 as a multi-bit digital ECG signal used by control circuit 80 for morphology analysis for analysis of a predetermined time segment of the ECG signal for determining evidence of VT/VF during a pacing escape interval according to the techniques disclosed herein.

At least one cardiac electrical signal may be received by sensing circuit 86 and passed to control circuit 80 for processing and analysis for determining evidence of VT/VF in a cardiac electrical signal segment based on VT/VF morphology metrics determined from the cardiac electrical signal segment by control circuit 80. VT/VF morphology metrics are parameters determined from a time segment of a cardiac electrical signal received by control circuit 80 from sensing circuit 86 that may relate to the amplitude, slope and/or frequency or period of the cardiac electrical signal and are correlated to the likelihood of VT/VF being present in the time segment of the cardiac electrical signal. The VT/VF morphology metrics can be determined independent of sensing R-waves from the cardiac electrical signal and can therefore be used to determine evidence of VT/VF being present in the cardiac electrical signal when R-waves and/or fibrillation waves are being undersensed and VT/VF is undetected. As described below, at least one cardiac electrical signal received over one or more predetermined time segments may be analyzed for determining evidence of VT/VF in a cardiac signal segment prior to delivery of a scheduled pacing pulse.

Timing circuit 90 may be configured to control various timers and/or counters used in setting various intervals and windows used in sensing ventricular event signals, determining time intervals between received Vsense signals (and delivered pacing pulses followed by Vsense signals), performing morphology analysis and controlling the timing of cardiac pacing pulses generated by therapy delivery circuit 84. Timing circuit 90 may start a timer in response to receiving Vsense signals from sensing channels 83 and 85 (and in response to delivered ventricular pacing pulses) for timing the RRIs between consecutively received in-channel Vsense signals (and in some instances from a delivered pacing pulse to a ventricular sensed event signal). Control circuit 80 may pass the RRI to arrhythmia detection circuit 92 for determining and counting tachyarrhythmia intervals.

Control circuit 80 may include an arrhythmia detection circuit 92 configured to analyze RRIs received from timing circuit 90 and cardiac electrical signals received from morphology signal channel 87 for detecting arrhythmia. Arrhythmia detection circuit 92 may be configured to detect asystole and tachyarrhythmia based on sensed cardiac electrical signal segment(s) meeting respective asystole or tachyarrhythmia detection criteria. For example, when a threshold number of Vsense signals from one sensing channel 83 or 85 each occur at a sensed event interval (RRI) that is less than a tachyarrhythmia detection interval, control circuit 80 may detect VT/VF. An RRI that is less (shorter) than the tachyarrhythmia detection interval is referred to as a "tachyarrhythmia interval." In some examples, a tachyarrhythmia detection based on the threshold number of tachyarrhythmia intervals being reached may be confirmed or rejected based on morphology analysis of a cardiac electrical signal.

In other examples, asystole or VT/VF may be detected by arrhythmia detection circuit 92 based on morphology analysis of a cardiac electrical signal sensed by morphology signal channel 87 over a predetermined time interval, e.g., 0.5 seconds to 8 seconds, or 3 seconds in an example without requiring a determination of RRIs. In some examples, arrhythmia detection circuit 92 may perform morphology analysis of cardiac signal segments for detecting arrhythmia without necessarily analyzing RRIs determined from Vsense signals received from sensing channels 83 and 85. In other examples, morphology analysis of cardiac signal segments by arrhythmia detection circuit 92 may be triggered by control circuit 80 when undersensing of R-waves by sensing channels 83 and 85 is suspected. Techniques for detecting VT/VF are generally disclosed in provisional U.S. Patent Application No. 63/250,535 (Liu, et al.) and corresponding U.S. patent application Ser. No. 17/823,055 and in provisional U.S. Patent Application No. 63/278,955 (Aranda Hernandez, et al.) and corresponding U.S. patent application Ser. No. 18/045,135 (Aranda Hernandez), the entire content of all of which is incorporated herein by reference. The techniques disclosed herein for controlling bradycardia pacing may be combined with the arrhythmia detection techniques disclosed in the above-incorporated references. However, it is to be understood that the techniques disclosed herein for determining evidence of VT/VF in a cardiac signal segment for use in potentially delaying or terminating bradycardia pacing may be used in conjunction with any techniques for detecting VT/VF for controlling delivery of tachyarrhythmia therapies, e.g., ATP therapy and/or CV/DF shocks.

Arrhythmia detection circuit 92 may be implemented in control circuit 80 as hardware, software and/or firmware that processes and analyzes signals received from sensing circuit 86 for detecting arrhythmia, including asystole and VT/VF. Arrhythmia detection circuit 92 may identify signal pulses for determining amplitude and/or pulse interval metrics of a time segment of a cardiac electrical signal for use in detecting arrhythmia, e.g., as described in the above-incorporated references. Arrhythmia detection circuit 92 may be configured to determine morphology metrics of cardiac signal segments that are correlated to the stability, slope content, and/or frequency content of the cardiac signal segment(s). The morphology metrics may be compared to criteria for detecting asystole or for detecting VT/VF for enabling therapy delivery circuit 84 to deliver an appropriate cardiac pacing and/or CV/DF shock therapy in response to an arrhythmia detection.

In some examples, arrhythmia detection circuit 92 may include comparators and counters for counting RRIs determined by timing circuit 90 from Vsense signals received from sensing channel 83 and/or sensing channel 85 that fall into various rate detection zones for determining a ventricular rate or performing other rate- or interval-based assessment of Vsense signals for detecting and discriminating VT and VF. For example, arrhythmia detection circuit 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter. The VF detection interval threshold may be set to 300 to 350 milliseconds (ms), as an example. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. RRIs that are less than the VT detection interval but greater than or equal to the VF detection interval may be counted by a VT interval counter. VT or VF may be detected when the respective VT or VF interval counter (or a combined VT/VF interval counter) reaches a threshold number of intervals to detect (NID).

As an example, the NID to detect VT may require that the VT interval counter reaches 18 VT intervals, 24 VT intervals, 32 VT intervals or other selected NID. In some examples, the VT intervals may be required to be consecutive intervals, e.g., 18 out of 18, 24 out of 24, 32 out of the most recent 32, or 100 out of the most recent 100 consecutive RRIs. The NID required to detect VF may be programmed to a threshold number of X VF intervals out of Y consecutive RRIs. For instance, the NID required to detect VF may be 18 VF intervals out of the most recent 24 consecutive RRIs or 30 VF intervals out 40 consecutive RRIs, or as high as 120 VF intervals out of 160 consecutive RRIs as examples. When a VT or VF interval counter reaches a respective NID, a ventricular tachyarrhythmia may be detected by arrhythmia detection circuit 92. The NID may be programmable and range from as low as 12 to as high as 120, with no limitation intended. VT or VF intervals may reach a respective NID when detected consecutively or non-consecutively out of a specified number of most recent RRIs. In some cases, a combined VT/VF interval counter may count both VT and VF intervals and detect a tachyarrhythmia episode based on the fastest intervals detected when a specified NID is reached.

Arrhythmia detection circuit 92 may be configured to perform other signal analysis for determining if other detection criteria are satisfied before detecting VT or VF based on an NID being reached, such as R-wave morphology criteria, onset criteria, stability criteria and noise and oversensing rejection criteria. To support these additional analyses, sensing circuit 86 may pass a digitized ECG signal to control circuit 80, e.g., from morphology signal channel 87, for morphology analysis performed by arrhythmia detection circuit 92 for detecting and discriminating heart rhythms. A cardiac electrical signal received by the morphology signal channel 87 (and/or sensing channel 83 and/or sensing channel 85) may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac signal segments for analysis performed by control circuit 80. Control circuit 80 may be a microprocessor-based controller, which may include HSRs, that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves.

Therapy delivery circuit 84 includes at least one charging circuit 94, including one or more charge storage devices such as one or more high voltage capacitors for generating high voltage shock pulses for treating VT/VF. Charging circuit 94 may include one or more low voltage capacitors for generating relatively lower voltage pulses, e.g., for cardiac pacing therapies. Therapy delivery circuit 84 may include switching circuitry 95 that controls when the charge storage device(s) are discharged through an output circuit 96 across a selected pacing electrode vector or CV/DF shock vector.

In response to detecting VT/VF, control circuit 80 may schedule a therapy and control therapy delivery circuit 84 to generate and deliver the therapy, such as ATP and/or CV/DF shocks. Therapy can be generated by initiating charging of high voltage capacitors of charging circuit 94. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit 96 of therapy delivery circuit 84 via a control bus. The output circuit 96 may include an output capacitor through which the charged high voltage capacitor is discharged via switching circuitry, e.g., an H-bridge, which determines the electrodes used for delivering the CV/DF pulse and the pulse wave shape. Therapy delivery circuit 84 may be configured to deliver electrical stimulation pulses for inducing tachyarrhythmia, e.g., T-wave shocks or trains of induction pulses, upon receiving a programming command from external device 40 (FIG. 1A) during ICD implant or follow-up testing procedures.

In some examples, the high voltage therapy circuit configured to deliver CV/DF shock pulses can be controlled by control circuit 80 to deliver pacing pulses, e.g., for delivering ATP, post shock pacing pulses, bradycardia pacing pulses or asystole pacing pulses. Therapy delivery circuit 84 may be configured to generate and deliver cardiac pacing pulses using the high voltage capacitor(s) that are chargeable to a shock voltage amplitude by charging the high voltage capacitor(s) to a relatively lower voltage corresponding to a cardiac pacing pulse amplitude for capturing and pacing the ventricular myocardium. In other examples, therapy delivery circuit 84 may include a low voltage therapy circuit including one or more separate or shared charging circuits, switch circuits and output circuits for generating and delivering relatively lower voltage pacing pulses for a variety of pacing needs. Charging of capacitors to a programmed pulse amplitude and discharging of the capacitors for a programmed pulse width may be performed by therapy delivery circuit 84 according to control signals received from control circuit 80 for delivering cardiac pacing pulses. As described above, timing circuit 90 may include various timers or counters that control when cardiac pacing pulses are delivered.

For example, cardiac pacing pulses may be delivered at a lower rate interval controlled by timing circuit 90 according to a corresponding programmed lower rate. The programmed lower rate generally defines a minimum rate that, if the patient's intrinsic heart rate falls below, bradycardia pacing is delivered. In this way, the programmed lower rate generally controls the minimum heart rate of the patient. As described below, however, a pacing pulse may be scheduled at a hysteresis interval that can be longer than the lower rate interval in some instances. Furthermore, a pacing pulse scheduled at a hysteresis interval or the lower rate interval may be delayed in some instances due to evidence of VT/VF according to the techniques disclosed herein. When an intrinsic R-wave is not sensed before expiration of a pacing interval controlled by timing circuit 90, a pacing pulse may be delivered by the therapy delivery circuit 84 if VT/VF evidence is not determined from a cardiac signal segment sensed during the pacing interval. The microprocessor of control circuit 80 may set the amplitude, pulse width, polarity or other characteristics of cardiac pacing pulses, which may be based on programmed values stored in memory 82.

According to the techniques disclosed herein, control circuit 80 may perform processing and analysis of at least one cardiac signal segment prior to delivery of a pending pacing pulse at the expiration of a pacing escape interval by therapy delivery circuit 84. When control circuit 80 determines evidence of VT/VF in the cardiac signal segment(s) preceding the scheduled time for delivery of a pending cardiac pacing pulse, the pending pacing pulse may be delayed. Control circuit 80 may analyze one or more additional cardiac signal segments during the delay, prior to the new scheduled time of the pending cardiac pacing pulse. When VT/VF evidence is determined from the one or more additional cardiac signal segments during the pacing delay, the pending cardiac pacing pulse may be delayed again. In some examples, the pending pacing pulse may be delayed up to a maximum time interval (e.g., up to 6 seconds, 7, seconds, 8 seconds, 9 seconds or 10 seconds), referred to herein as the "maximum pacing delay." If the maximum pacing delay is reached and VT/VF has not been detected by arrhythmia detection circuit 92, therapy delivery circuit 84 may deliver the pending cardiac pacing pulse. If arrhythmia detection circuit 92 detects VT/VF at a time prior to delivery of the delayed pending pacing pulse, the pending pacing pulse may be cancelled. Therapy delivery circuit 84 may generate and deliver a tachyarrhythmia therapy, e.g., ATP therapy and/or one or more CV/DF shocks, in response to the detected VT/VF.

Control parameters utilized by control circuit 80 for sensing cardiac event signals, detecting arrhythmias, and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
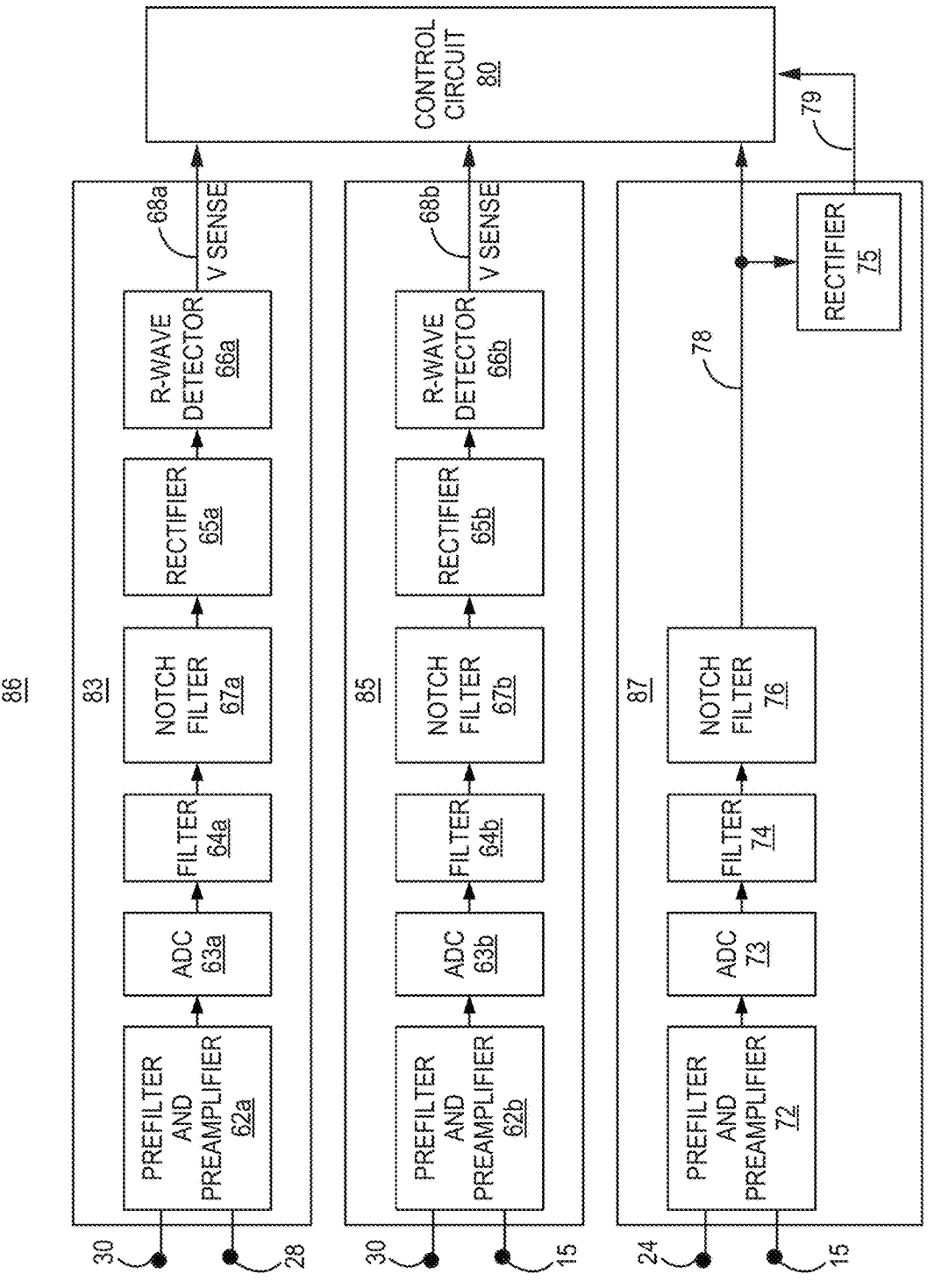
FIG. 4 is a conceptual diagram of circuitry that may be included in a sensing circuit of the ICD shown in FIG. 3 according to some examples.

FIG. 4 is a conceptual diagram of circuitry that may be included in sensing circuit 86 shown in FIG. 3 according to one example. Sensing circuit 86 may include a first sensing channel 83, second sensing channel 85 and morphology signal channel 87 according to one example. First sensing channel 83 and second sensing channel 85 may each be selectively coupled via switching circuitry included in sensing circuit 86 to a respective sensing electrode vector including at least one electrode carried by extra-cardiovascular lead 16. First sensing channel 83 may be coupled to a first sensing electrode vector for receiving a first cardiac electrical signal, and second sensing channel 85 may be coupled to a second sensing electrode vector, different than the first sensing electrode vector for receiving a second cardiac electrical signal, different than the first cardiac electrical signal. In some examples, first sensing channel 83 may be coupled to a sensing electrode vector that is a short bipole, having a relatively shorter inter-electrode distance than the sensing electrode vector coupled to the second sensing channel 85 or to morphology signal channel 87. In the example shown, the first sensing channel 83 is coupled to pace/sense electrodes 28 and 30 carried by lead 16. In some examples, first sensing channel 83 may be coupled to a sensing electrode vector that is approximately vertical (when the patient is in an upright position) or approximately aligned with the cardiac axis to increase the likelihood of a relatively high R-wave signal amplitude relative to the P-wave signal amplitude. A relatively short inter-electrode distance, e.g., between electrodes 28 and 30 carried by lead 16, may be relatively less likely to be contaminated by skeletal muscle myopotential noise, EMI or other non-cardiac noise compared to a relatively longer inter-electrode distance but may have greater variability in R-wave signal strength compared to a relatively longer inter-electrode distance.

The second sensing channel 85 may be coupled to a second sensing electrode vector that is a short bipole or a relatively longer bipole compared to the first sensing electrode vector. The second sensing electrode vector may also be generally vertical or aligned with the cardiac axis. However, the second sensing electrode vector may be orthogonal or transverse relative to the first sensing electrode vector in other examples. In the example shown, the second sensing channel 85 is coupled to pace/sense electrode 30 and housing 15 such that it is a relatively longer bipole that is substantially transverse to the sensing electrode vector coupled to the first sensing channel 83. In other examples, the first or second sensing channels may be coupled to either of pace/sense electrodes 28 or 30 paired with housing 15, either of pace/sense electrodes 28 or 30 paired with coil electrode 24, or either of pace sense electrodes 28 or 30 paired with coil electrode 26, as long as at least one electrode is different between the two sensing electrode vectors. In further examples, either or both of first or second sensing channels 83 or 85 may be coupled to a sensing electrode vector that does not necessarily include one of pace/sense electrodes 28 or 30. For example, a sensing electrode vector may be coupled to sensing channel 83 or sensing channel 85 that includes one or both of coil electrodes 24 or 26 and/or housing 15.

Sensing circuit 86 may include a morphology signal channel 87 for sensing a third cardiac electrical signal. For instance, morphology signal channel 87 may receive a raw cardiac electrical signal from a third sensing electrode vector, for example from a vector that includes one electrode 24, 26, 28 or 30 carried by lead 16 paired with housing 15. Morphology signal channel 87 may be selectively coupled to a relatively long bipole having an inter-electrode distance or spacing that is greater than the sensing electrode vector coupled to first sensing channel 83 and/or second sensing channel 85 in some examples. The third sensing electrode vector may be, but not necessarily, approximately orthogonal to at least one of the first channel sensing electrode vector or the second channel sensing electrode vector. In the example shown, coil electrode 24 and housing 15 may be coupled to morphology signal channel 85 to provide the third sensed cardiac electrical signal. In some examples, the sensing electrode vector coupled to morphology signal channel 87 may provide a relatively far-field or more global cardiac signal compared to a relatively shorter bipole that may be coupled to the first sensing channel 83 or the second sensing channel 85. In other examples, any vector selected from the available electrodes, e.g., electrodes 24, 26, 28, 30 and/or housing 15, may be included in a sensing electrode vector coupled to morphology signal channel 87.

The sensing electrode vectors coupled to first sensing channel 83 and second sensing channel 85 and, at least in some examples, morphology signal channel 87 may be different sensing electrode vectors, which may have no common electrodes or only one common electrode but not both electrodes in common between the different sensing electrode vectors. In other examples, however, the sensing electrode vector coupled to one of the first sensing channel 83 or the second sensing channel 85 may be the same sensing electrode vector coupled to the morphology signal channel 87. In this case, a sensing channel 83 or 85 and the morphology signal channel 87 may be combined or include shared components such that a morphology signal and Vsense signals may be output to control circuit 80 from one sensing channel.

The first sensing channel 83 and the second sensing channel 85 may each receive a cardiac electrical signal for sensing ventricular event signals in response to the cardiac electrical signal crossing an R-wave sensing threshold. The morphology signal channel 87 may receive a third cardiac electrical signal for passing a multi-bit digital ECG signal to control circuit 80 for morphology analysis. In the illustrative example shown in FIG. 4, the signals received by first sensing channel 83, second sensing channel 85 and morphology signal channel 87 are provided as differential input signals to a pre-filter and pre-amplifier 62*a*, 62*b*, and 72, respectively. Non-physiological high frequency and DC signals may be filtered by a low pass or bandpass filter included in each of pre-filter and pre-amplifiers 62*a*, 62*b* and 72, and high voltage signals may be removed by protection diodes included in pre-filter and pre-amplifiers 62*a*, 62*b* and 72. Pre-filter and pre-amplifiers 62*a*, 62*b* and 72 may amplify the pre-filtered signal by a gain of between 10 and 100, and in one example a gain of 17, though each channel may have a different gain and filter bandwidth. Pre-filter and pre-amplifiers 62*a*, 62*b* and 72 may convert the differential input signal to a single-ended output signal passed to an analog-to-digital converter (ADC) 63*a*, 63*b*, and 73, respectively. Pre-filter and pre-amplifiers 62*a*, 62*b* and 72 may provide anti-alias filtering and noise reduction prior to digitization.

ADC 63*a*, ADC 63*b* and ADC 73, respectively, convert the first cardiac electrical signal, second cardiac electrical signal and third cardiac electrical signal from an analog signal to a digital bit stream, which may be sampled at 128 or 256 Hz, as examples. ADC 63*a*, ADC 63*b* and ADC 73 may be sigma-delta converters (SDC), but other types of ADCs may be used. In some examples, the outputs of ADC 63*a*, ADC 63*b* and ADC 73 may be provided to decimators (not shown), which function as digital low-pass filters that increase the resolution and reduce the sampling rate of the respective cardiac electrical signals.

The digital outputs of ADC 63*a*, ADC 63*b* and ADC 73 are each passed to respective filters 64*a*, 64*b* and 74, which may be digital bandpass filters. The bandpass filters 64*a*, 64*b* and 74 may have the same or different bandpass frequencies. For example, filters 64*a* and 64*b* may have a bandpass of approximately 8 Hz to 45 Hz or from 13 Hz to 39 Hz, as examples, for passing cardiac electrical signals such as R-waves typically occurring in this frequency range. Filter 74 of the morphology signal channel 87 may have a relatively wider bandpass of approximately 2.5 to 100 Hz. In some examples, each of sensing channel 83, sensing channel 85 and morphology signal channel 87 may further include a notch filter 67*a*, 67*b*, and 76, respectively, to filter 50 Hz and 60 Hz noise signals. Each notch filter 67*a*, 67*b*, and 76 may be individually turned on or off in some examples.

The narrow bandpass and notch-filtered signal (if the notch filter is turned on) in first sensing channel 83 and second sensing channel 85 is passed from respective filter 64*a* or filter 64*b* (or 67*a* or 67*b*) to rectifier 65*a* or rectifier 65*b* to produce a filtered, rectified signal output to respective R-wave detectors 66*a* and 66*b*. First sensing channel 83 includes an R-wave detector 66*a* for sensing ventricular event signals in response to the first cardiac electrical signal crossing an R-wave sensing threshold. Second sensing channel 85 includes an R-wave detector 66*b* for sensing ventricular event signals in response to the second cardiac electrical signal crossing an R-wave sensing threshold, which may be controlled separately from the R-wave sensing threshold controlled by R-wave detector 66*a*. R-wave detectors 66*a* and 66*b* may each include an auto-adjusting sense amplifier, comparator and/or other detection circuitry that compares the incoming filtered and rectified cardiac electrical signal to an R-wave sensing threshold and produces a Vsense signal 68*a* or 68*b* when the respective first or second cardiac electrical signal crosses the respective R-wave sensing threshold outside of a post-sense (or post-pace) blanking interval.

The R-wave sensing threshold may be a multi-level sensing threshold, e.g., as disclosed in U.S. Pat. No. 10,252,071 (Cao, et al.), incorporated herein by reference in its entirety. Briefly, the multi-level sensing threshold may have a starting sensing threshold value held for a first drop time interval, which may be equal to a tachycardia detection interval or an expected R-wave to T-wave interval, then drops, e.g., in a single step decrement, to a second sensing threshold value held until a second drop time interval expires, which may be 0.3 to 2.5 seconds long and can be 0.5 to 2.5 seconds long and is 2.15 seconds (from the Vsense signal) in one example. After the second drop time interval, the sensing threshold drops to a minimum sensing threshold, which may be equal to a programmed sensitivity and is also referred to herein as the "sensing floor" because it represents the minimum amplitude of the cardiac electrical signal that may be sensed as a ventricular event. The R-wave sensing thresholds used by R-wave detector 66*a* and 66*b* may each be set to a starting value based on a maximum peak amplitude of the respective first or second cardiac electrical signal determined by the R-wave detector 66*a* or 66*b* during the most recent post-sense blanking period. In some examples, an R-wave peak tracking period may be defined as a portion of the post-sense blanking period during which the maximum peak amplitude is determined. The starting R-wave sensing threshold of each sensing channel 83 and 85 may decrease over time according to one or more stepwise drops and/or linear or non-linear decay rates until reaching the minimum sensing threshold (or until an R-wave sensing threshold crossing by the cardiac electrical signal occurs). In some instances, the R-wave sensing threshold may be adjusted to the minimum sensing threshold before the expiration of the first drop time interval or before the expiration of the second drop time interval depending on the maximum peak amplitude determined during the R-wave peak tracking period.

The techniques described herein are not limited to a specific behavior of the sensing threshold or specific R-wave sensing techniques. Instead, other decaying, step-wise adjusted or other automatically adjusted sensing thresholds may be utilized for sensing ventricular event signals from the respective first and second cardiac electrical signals. R-wave detector 66*a* or 66*b* may produce a Vsense signal 68*a* or 68*b* in response to the respective first cardiac electrical signal or second cardiac electrical signal crossing the R-wave sensing threshold. The Vsense signal 68*a* or 68*b* is passed to control circuit 80.

The wideband-filtered, digital cardiac electrical signal 78 output from morphology signal channel 87 may be passed to control circuit 80 for performing morphology-based arrhythmia detection. In some examples, the digital cardiac electrical signal 78, also referred to herein as the "morphology signal," is passed to rectifier 75 and a rectified wideband filtered signal 79 is passed to control circuit 80 for processing and analysis. In some cases, both the filtered, non-rectified signal 78 and the rectified signal 79 are passed to control circuit 80 from morphology signal channel 87 for use in determining morphology features of the ECG signal. In some instances, an n-second ECG signal segment may be buffered in memory 82 by control circuit 80 for processing and analysis for detecting asystole and tachyarrhythmia, e.g., as generally described in the above-incorporated U.S. Patent Application No. 63/278,955 and corresponding U.S. patent application Ser. No. 18/045,135. ECG signal segments analyzed by control circuit 80 may undergo additional low pass, bandpass and/or high pass filtering prior to analysis for determining morphology features or other features of the ECG signal segment for arrhythmia detection. As described below, ECG signal segments received from morphology signal channel 87 may be analyzed by control circuit 80 for determining evidence of VT/VF prior to delivery of a pending cardiac pacing pulse to reduce the likelihood of pacing into a VT/VF rhythm.

The configuration of sensing channels 83 and 85 and morphology signal channel 87 as shown in FIG. 4 is illustrative in nature and should not be considered limiting of the techniques described herein. Sensing circuit 86 may include more or fewer components than illustrated and described in FIG. 4 and some components may be shared between sensing channels 83 and 85 and morphology signal channel 87. For example, a common cardiac electrical signal from a selected sensing electrode vector may be received by a prefilter and preamplifier circuit and ADC and subsequently be passed to a narrowband filter in one of sensing channels 83 or 85 and to a wideband filter in morphology signal channel 87. In other examples, sensing circuit 86 may include only one or more than two sensing channels, each configured to produce a Vsense signal, and/or more than one morphology signal channel. In other examples, a wideband filtered morphology signal may be passed to control circuit 80 from one of sensing channels 83 or 85 for performing analysis of cardiac signal segments according to the techniques disclosed herein for use in detecting arrhythmia and/or controlling delivery of cardiac pacing pulses based on evidence of VT/VF in a cardiac signal segment. Furthermore, the components for filtering, amplifying, digitizing, rectifying, etc. may be arranged in a different order or combination than shown in FIG. 4.

Figure 5:
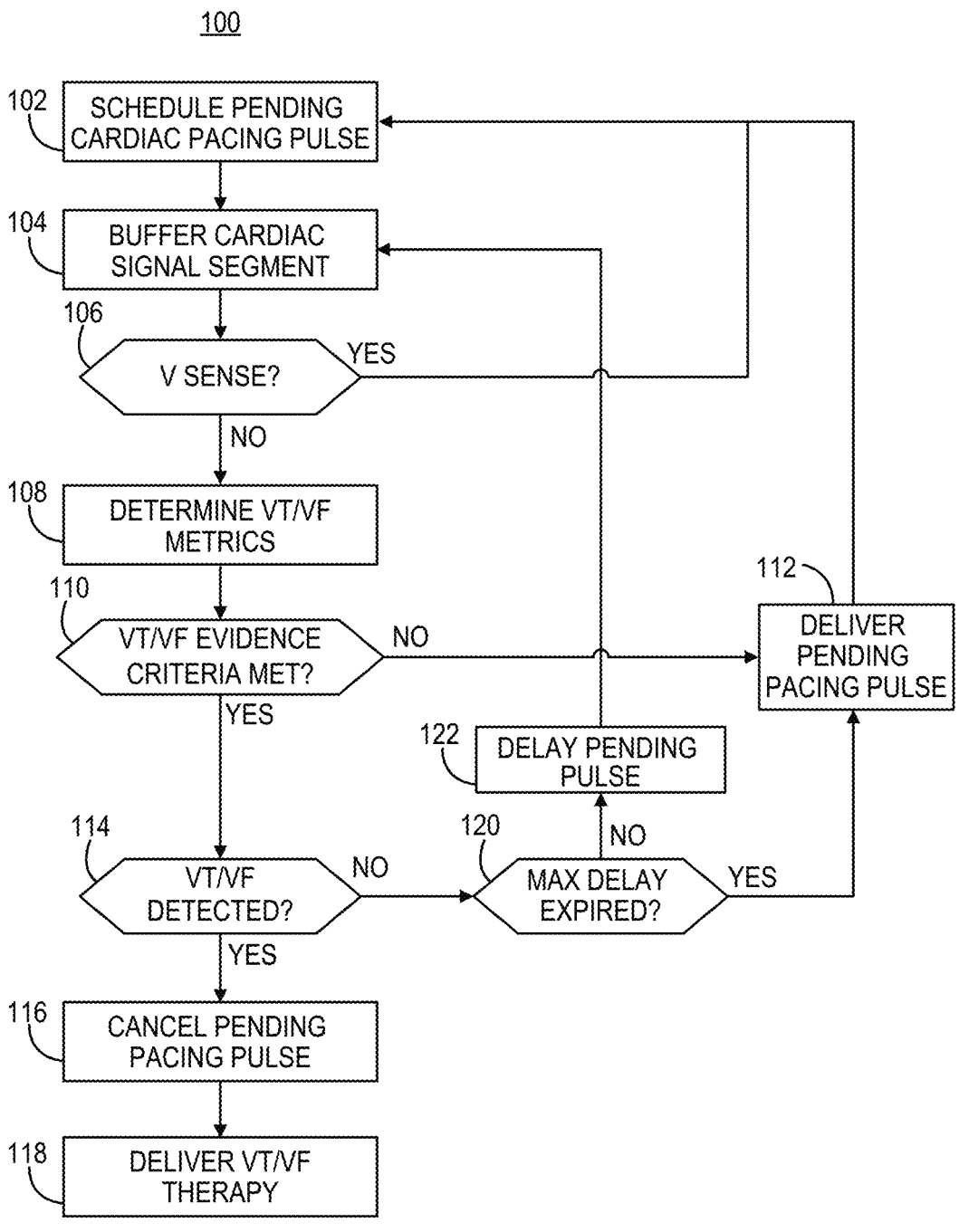
FIG. 5 is a flow chart of a method for controlling the delivery of cardiac pacing pulses according to one example.

FIG. 5 is a flow chart 100 of a method for controlling the delivery of cardiac pacing pulses according to one example. At block 102, control circuit 80 schedules a pending cardiac pacing pulse. The cardiac pacing pulse may be scheduled as a bradycardia pacing pulse for treating a slow ventricular rate or the absence of ventricular intrinsic depolarizations, e.g., in response to detecting asystole or a long ventricular pause. The techniques disclosed herein for controlling the cardiac pacing pulse delivery relate to the delivery of cardiac pacing pulses for the treatment of bradycardia or asystole. As such, the pending cardiac pacing pulse that is scheduled at block 102 is not a pacing pulse that is part of an ATP therapy scheduled in response to detecting VT/VF. In that case, known VT/VF is occurring and ATP may be scheduled for treating the VT/VF. The pending cardiac pacing pulse that is scheduled at block 102 is intended to treat bradycardia or asystole during a non-VT/VF rhythm.

The pending cardiac pacing pulse may be scheduled at block 102 by starting a pacing escape interval having a time duration that may be set according to a programmed lower rate interval, e.g., 1 second to 2 seconds, or to a hysteresis interval, which may be 2 to 6 seconds or 3 to 4 seconds in duration as examples. The pacing pulse may be scheduled at the expiration of a pacing escape interval set to the lower rate interval or the hysteresis interval and started in response to receiving a Vsense signal from one of sensing channels 83 or 85. In some examples, the pacing escape interval may be started in response to identifying a valid event signal based on a Vsense signal received from both sensing channels within a validation time window. In other examples, the pacing escape interval may be started in response to identifying a valid event signal based on a Vsense signal received from one sensing channel, e.g., sensing channel 83 or 85, and R-wave morphology criteria being met by the morphology signal sensed during a validation window started in response to the one Vsense signal. Various methods for identifying valid event signals and starting pacing escape intervals based on valid event signals are described in the above-incorporated provisional U.S. Patent Application No. 63/251,803, provisional U.S. Patent Application No. 63/251,820 and corresponding U.S. patent application Ser. No. 17/822,681. In other instances, the pacing pulse may be scheduled at the expiration of a pacing escape interval started in response to the delivery of a preceding pacing pulse by therapy delivery circuit 84.

In some examples, timing circuit 90 of control circuit 80 may set the pacing escape interval to a hysteresis interval when control circuit 80 has been receiving Vsense signals and a pacing pulse has not been delivered recently, e.g., for two or more ventricular cycles. Once a pending pacing pulse scheduled at the hysteresis interval is delivered (which may be after one or more delays following expiration of the hysteresis interval according to the techniques disclosed herein), control circuit 80 may schedule subsequent pacing pulses at the programmed lower rate interval. In some examples, timing circuit 80 may set the pacing escape interval to a hysteresis interval after delivering bradycardia pacing pulses at the programmed lower rate interval for a predetermined time interval or total number of pacing pulses. When pacing pulses are delivered by electrodes carried by a non-transvenous lead, pacing pulse delivery may be perceptible by the patient. The number of consecutively delivered pacing pulses delivered at the lower rate interval may be limited by control circuit 80 by periodically setting a hysteresis pacing escape interval to promote pacing inhibition due to sensing of intrinsic ventricular event signals during the relatively longer hysteresis interval.

At block 104, control circuit 80 may begin buffering a cardiac signal segment in memory 82. A time segment of the morphology signal sensed by morphology signal channel 87 during the pacing escape interval may be buffered in memory 82 for analysis by control circuit 80 for determining evidence of VT/VF prior to delivering the scheduled pacing pulse. For the sake of illustration, the morphology signal received from morphology signal channel 87 is described herein as the signal that is processed and analyzed for determining VT/VF evidence in cardiac signal segments for the purpose of controlling cardiac pacing pulse delivery. It is to be understood, however, that a cardiac signal sensed by any sensing channel of sensing circuit 86 may be received by control circuit 80 for processing and analysis for determining evidence of VT/VF according to the techniques disclosed herein.

As described below, buffering of the cardiac signal segment may begin after an onset delay interval following the starting time of the current pacing escape interval. The cardiac signal segment may be buffered over a time interval that is 0.25 to 3 seconds in duration, as examples. The time duration of the cardiac signal segment that is buffered at block 104 may depend on the time duration of the current pacing escape interval. For example, when the current pacing escape interval is 1 second, for pacing at a rate of 60 pulses per minute (ppm), the cardiac signal segment may be 0.4 to 0.8 seconds in duration, as examples. When the current pacing escape interval is longer, e.g., 2 to 4 seconds, the cardiac signal segment that is buffered at block 104 may be relatively longer, e.g., 1.5 to 3.5 seconds. Furthermore, multiple cardiac signal segments may be buffered during a single pacing escape interval in some examples. For the sake of convenience, one signal segment is described as being buffered and analyzed in the example flow chart 100. Other examples involving buffering and analysis of multiple cardiac signal segments during a single pacing escape interval are described below with accompanying flow charts and diagrams.

The cardiac signal segment may be buffered at block 104 up to a processing time interval prior to the expiration of the currently running pacing escape interval, e.g., 10 milliseconds (ms) to 100 ms prior to the expiration of the pacing escape interval. The time interval for buffering the cardiac signal segment may expire at a processing time interval earlier than the expiration of the pacing escape interval to allow processing time required for control circuit 80 to determine evidence of VT/VF from the cardiac signal segment and delay the pending pacing pulse before the pacing escape interval expires.

When a Vsense signal is received by control circuit 80 from sensing circuit 86 any time during the pacing escape interval (as indicated at block 106), control circuit 80 may inhibit the scheduled pacing pulse. In some examples, control circuit 80 determines if a received Vsense signal is a valid event signal before inhibiting the scheduled pacing pulse based on a Vsense signal received from one sensing channel. A Vsense signal received from one sensing channel 83 or 85 may be determined to be valid event signal based on a second Vsense signal received from the other sensing channel 85 or 83 within a validation time window started in response to the first Vsense signal.

In other examples, when a second Vsense signal is not received within the validation window, the single Vsense signal received from one sensing channel 83 or 85 may be determined to be a valid event signal based on morphological analysis of the morphology signal sensed during the validation window for determining if R-wave criteria are met. The R-wave morphology criteria may be met when a morphology matching score determined between the morphology signal sensed during the validation window and a previously stored R-wave template is greater than a match threshold. Additionally or alternatively, a noise pulse count may be determined during a post-sense blanking period. When the noise pulse count is less than a threshold number the Vsense signal may be deemed a valid event signal. In other examples, the maximum peak amplitude, peak slope, signal width, difference between the maximum and minimum of a first order difference signal determined from the cardiac electrical signal during the validation window, or other morphology features may be determined and compared to R-wave morphology criteria, singly or in any combination, for validating a single Vsense event signal received from one sensing channel. If R-wave morphology criteria are met, the single Vsense signal may be determined to be a valid event signal. Control circuit 80 may return to block 102 to schedule the next pacing pulse by restarting the pacing escape interval in response to a valid Vsense signal.

While the flow chart 100 shows checking for a Vsense signal after starting to buffer the cardiac signal segment, it is to be understood that a Vsense signal may be received by control circuit 80 at any time during the pacing escape interval. When a Vsense signal, which may be identified as a valid event signal by control circuit 80, is received prior to starting buffering or during buffering of the cardiac signal segment, the buffering and/or analysis of the cardiac signal segment may be aborted because the valid Vsense signal causes the control circuit 80 to inhibit the pending pacing pulse, which precludes pacing into any undersensed or undetected VT/VF rhythm without requiring analysis for VT/VF evidence in a cardiac signal segment.

When a Vsense signal is not received from the sensing circuit 86 (as indicated at block 106), prior to the expiration of the currently running pacing escape interval, a ventricular pacing pulse may be needed to provide ventricular rate support and avoid a long ventricular pause. In some examples, control circuit 80 may receive a Vsense signal from one sensing channel 83 or 85 that is not identified as a valid event signal by control circuit 80 at block 106. In this case the pacing escape interval may expire due to the absence of a valid Vsense signal. Control circuit 80 may not restart a pacing escape interval to inhibit a scheduled pacing pulse in response to a single Vsense signal that is determined to be an invalid event signal. However, in some instances, the absence of a Vsense signal, or the absence of a valid event signal, during a pacing escape interval may be due to undersensing of R-waves or fibrillation waves by sensing channels 83 and 85. In order to avoid delivering a bradycardia pacing pulse into a VT/VF rhythm that may be undersensed, control circuit 80 may analyze at least one buffered cardiac signal segment, which may be acquired during the pacing escape interval, e.g., immediately prior to the expiration of the pacing escape interval.

At block 108, control circuit 80 may determine one or more VT/VF morphology metrics for determining evidence of VT/VF in the cardiac signal segment sensed during the pacing escape interval. Examples of VT/VF morphology metrics that may be determined at block 110 include a low slope content, a spectral width, a mean period, a signal pulse count and/or signal pulse interval. The VT/VF morphology metrics may be compared to VT/VF evidence criteria at block 110. The VT/VF evidence criteria may include one or more thresholds, values or other requirements or conditions that are applied to the VT/VF morphology metrics, individually and/or in combination, for determining whether the slope content, frequency content, number of signal pulses and/or signal pulse intervals of the cardiac signal segment correspond to the slope content, frequency content, number of signal pulses and/or signal pulse intervals that would be expected in a cardiac signal segment during a VT/VF rhythm.

If the VT/VF evidence criteria are not met at block 110, the cardiac signal segment is unlikely to be sensed during a VT/VF rhythm. Therapy delivery circuit 84 may safely deliver the pending pacing pulse at block 112. Control circuit 80 may return to block 102 to schedule the next pacing pulse by restarting a pacing escape interval. It is to be understood that the criteria applied at block 110 for determining VT/VF evidence can be different than criteria that is applied by arrhythmia detection circuit 92 for detecting VT/VF, even though some of the same VT/VF morphology metrics may be determined from the cardiac signal segment at block 108 as are determined by arrhythmia detection circuit 92 for detecting VT/VF. For example, as described below in conjunction with FIGS. 6-8, VT/VF evidence criteria may be established by setting thresholds applied to VT/VF morphology metrics for determining when the cardiac signal segment is a VT/VF rhythm with a high sensitivity and/or specificity. In some examples, thresholds for determining VT/VF evidence with high specificity for controlling bradycardia or asystole pacing may be less sensitive than thresholds applied for detecting VT/VF for controlling tachyarrhythmia therapies. The determination of VT/VF evidence from a cardiac signal segment at block 110 for controlling cardiac pacing pulse delivery may be insufficient evidence for detecting a VT/VF episode and delivering tachyarrhythmia therapy. However, the determination of VT/VF evidence based on criteria applied at block 110 may be sufficient to determine that the cardiac signal looks enough like VT/VF that a pending pacing pulse should be delayed, reducing the likelihood of pacing into a VT/VF rhythm. The delay in delivering the pending pacing pulse may allow control circuit 80 additional time for detecting a VT/VF episode without interference by a delivered pacing pulse and without risk of accelerating a VT/VF rhythm due to pacing pulse delivery.

When VT/VF evidence criteria are met at block 110, and arrhythmia detection circuit 92 has not yet detected VT/VF according to tachyarrhythmia detection algorithms that may be executed concurrently ("no" branch of block 114), control circuit 80 may delay the pending pacing pulse at block 122. In the example shown, control circuit 80 may first verify that a maximum pacing delay has not expired at block 120. In some examples, control circuit 80 may delay a pending cardiac pacing pulse up to a maximum pacing delay after the expiration of a pacing escape interval. The maximum pacing delay may be 2 seconds, 3 seconds, 4 seconds, 5 seconds, 6 seconds, 7 seconds, 8 seconds or 9 seconds as examples. The maximum pacing delay may depend on the duration of the pacing escape interval and may be set to avoid a long ventricular pause of up to a maximum of 9 seconds, as an example, including the pacing escape interval and all subsequent pacing delays, for example. In some instances, the maximum pacing delay may be equal to a programmed hysteresis interval.

When the maximum pacing delay has not been reached ("no" branch of block 120), control circuit 80 may delay the pending pacing pulse at block 122. Control circuit 80 may delay the pending pacing pulse by a predetermined time interval, which may be equal to, less than, or greater than the current pacing escape interval. In some examples, control circuit 80 may delay the pending pacing pulse by one lower rate interval. If the current pacing escape interval is the hysteresis interval, control circuit 80 may delay the pending pacing pulse by one hysteresis interval, one lower rate interval, or another selected delay interval. Control circuit 80 may delay the pending pacing pulse by restarting the pacing escape interval set to the hysteresis interval or the lower rate interval in some examples. After delaying the pending pacing pulse, control circuit 80 may return to block 104 to begin buffering another cardiac signal segment to be analyzed for determining evidence of VT/VF.

When the maximum pacing delay has expired at block 120, control circuit 80 may deliver the pending pacing pulse at block 112 without further delay. If arrhythmia detection circuit 92 has not detected VT/VF during the maximum pacing delay, control circuit 80 may deliver the pending pacing pulse. True asystole or a long ventricular pause is likely occurring such that a pacing pulse is needed. In some examples, control circuit 80 may delay a pending pacing pulse for up to 6 to 9 seconds. For instance, control circuit 80 may restart the lower rate interval 3 to 8 times (depending on what the lower rate is programmed to) to delay the pending pacing pulse a corresponding number of times when VT/VF evidence criteria are met at block 110. If VT/VF is not detected by control circuit 80 at block 114 during the repeated delays of the pending pacing pulse, the pending pacing pulse is delivered at block 112 after a maximum pacing delay. Control circuit 80 returns to block 102 to schedule the next pacing pulse and may repeat the process of flow chart 100. It is recognized, however, that in some examples a maximum limit to the pacing delay may not be applied. Multiple pacing delay intervals may be started until a valid Vsense signal is received, VT/VF is detected or VT/VF evidence is no longer determined such that expiration of a pacing delay interval occurs with the pending pacing pulse being delivered.

When arrhythmia detection circuit 92 detects VT/VF at block 114 while a cardiac pacing pulse is pending, control circuit 80 may cancel the pending pacing pulse at block 116. Therapy delivery circuit 84 may deliver tachyarrhythmia therapy at block 118 according to a programmed menu of therapies which may include one or more ATP therapies and/or one or more CV/DF shocks. Arrhythmia detection circuit 80 may detect VT/VF at block 114 based on analysis of one or more cardiac signal segments (which may be different segments than the segment(s) that are buffered at block 104) for detecting VT/VF based on cardiac signal morphology analysis without requiring Vsense signals for determining RRIs. Methods for detecting VT/VF based on cardiac signal segment analysis are generally disclosed in above-incorporated U.S. Patent Application No. 63/278,955 and corresponding U.S. patent application Ser. No. 18/045, 135. VT/VF may be detected by control circuit 80 according to any detection algorithm, which may be executed in parallel with asystole detection and bradycardia sensing and pacing operations performed by control circuit 80. In this way, when VT/VF evidence is determined prior to the scheduled time of a pending pacing pulse but VT/VF has not yet been detected, the pending pacing pulse may be withheld for at least a delay interval to avoid interference with VT/VF detection.

Figure 6:
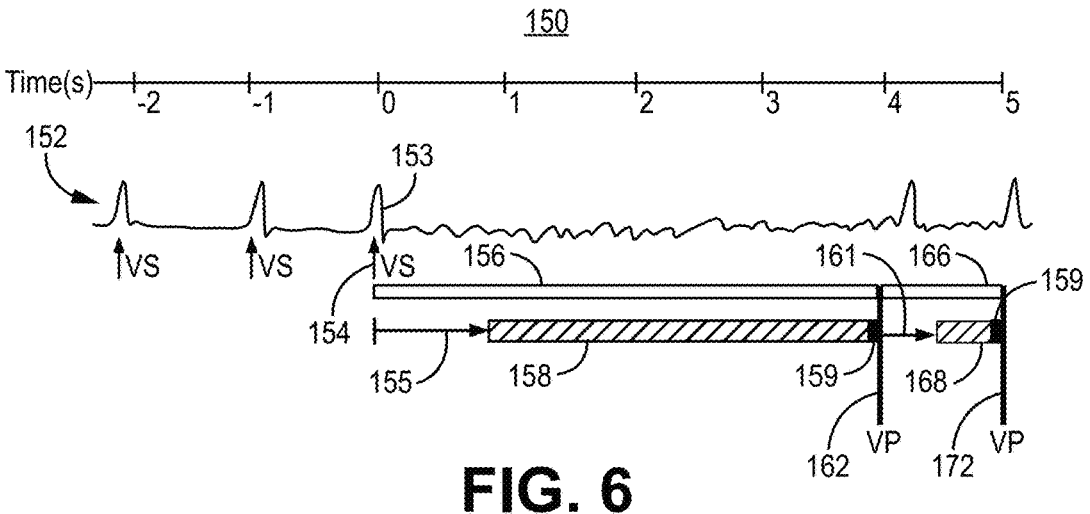
FIG. 6 is a diagram of a method for controlling delivery of cardiac pacing pulses according to one example.

FIG. 6 is a timing diagram 150 of a method for controlling delivery of cardiac pacing pulses according to one example. A cardiac electrical signal 152 may be sensed by sensing circuit 86, e.g., by morphology signal channel 87, and passed to control circuit 80. Control circuit 80 may receive Vsense signals 154, each corresponding in time to an R-wave 153 of cardiac electrical signal 152, from sensing circuit 86. A single sensing channel may be included in sensing circuit 86 for sensing R-waves or a single sensing channel may be selected out of multiple sensing channels, e.g., sensing channels 83 and 85 shown in FIG. 4, for sensing R-waves for controlling bradycardia pacing. Control circuit 80 may start a pacing escape interval in response to each Vsense signal 154.

In other examples, each Vsense signal 154 shown in FIG. 6 may correspond to a valid event signal identified by control circuit 80 according to any of the techniques disclosed in the above-incorporated U.S. Patent Application No. 63/251,803, U.S. Patent, Application No. 63/251,820 and corresponding U.S. patent application Ser. No. 17/822, 681. When ICD 14 includes two sensing channels, e.g., sensing channels 83 and 85 shown in FIG. 4, a Vsense signal received from one sensing channel 83 or 85 may be determined to be an invalid event signal by control circuit 80, e.g., if a second Vsense signal is not received from the other sensing channel 85 or 83 within a validation window of time and/or R-wave morphology criteria are not met by a cardiac electrical signal received from the sensing circuit 86 during the validation window. In some examples, when a Vsense signal is received from both sensing channels 83 and 85 within the validation window from each other, but the peak amplitude of the sensed signal is low on one or both channels (e.g., less than a threshold amplitude set to a multiple of the programmed sensitivity for the respective sensing channel), R-wave morphology criteria may be required to be met by the signal received from sensing channel 83, sensing channel 85 and/or morphology signal channel 87 for control circuit 80 to identify the time-matched Vsense signals as a valid event signal corresponding to a true R-wave. In any of these examples, control circuit 80 may not necessarily start a pacing escape interval in response to every Vsense signal that is received from a sensing channel 83 or 85 because some Vsense signals may not be determined to be valid event signals.

As such, in some examples the Vsense signals 154 shown in FIG. 6 may generally represent valid event signals identified by control circuit 80 when sensing circuit 86 includes two sensing channels. In other examples, however, when a single sensing channel is included in sensing circuit 86, or when a single sensing channel 83 or 85 is selected for sensing R-waves for controlling bradycardia pacing, control circuit 80 may start a pacing escape interval in response to each Vsense signal 154 without requiring validation of the Vsense signals as in a two-channel sensing scheme.

The pacing escape interval 156 started in response to Vsense signal 154 is shown set to a hysteresis interval of 4 seconds in this example. The pacing escape intervals started in response to the earlier Vsense signals 154 shown in FIG. 6 are not illustrated for the sake of clarity. The pacing escape intervals started in response to the earlier Vsense signals but now shown in FIG. 6 would be restarted in response to the next Vsense signal. Upon starting pacing escape interval 156, control circuit 80 may wait for an onset delay interval 155 after the Vsense signal 154 and then start buffering the cardiac electrical signal 152 over time segment 158 in memory 82. The onset delay interval 155 may be applied following a Vsense signal 154 (or delivered pacing pulse) because the onset of VT/VF is not expected to occur immediately after the Vsense signal 154. The onset of VT/VF could occur any time during a pacing escape interval after ventricular myocardial repolarization, which may be after the onset delay interval 155.

Furthermore, processing and analysis of the cardiac electrical signal 152 immediately after the Vsense signal 154 (or a post-sense blanking period) may cause unnecessary processing burden and battery drain of power source 98 because a Vsense signal may be received during a relatively high percentage of pacing escape intervals. By applying the onset delay interval 155, processing burden and power required for analyzing the cardiac electrical signal 152 prior to the time of a pending pacing pulse can be reduced. The time period immediately prior to the scheduled pacing pulse, e.g., near then end of the pacing escape interval 156, may be of greatest interest for determining if the cardiac electrical signal 152 has characteristics of VT/VF, such as the slope content, frequency content, signal pulse number and/or signal pulse intervals, that would be expected in the cardiac signal segment during a VT/VF rhythm. However, some minimum duration of a cardiac signal segment may be required for obtaining VT/VF morphology metrics determined from the cardiac signal segment that are meaningful in determining evidence of VT/VF. For example, the cardiac signal segment may be buffered over a time segment that is greater than at least one VT or VF detection interval. Examples of a minimum cardiac signal segment duration may be 300 ms, 350 ms or 400 ms. In some examples, a single, relatively short, cardiac signal segment may not provide sufficient evidence of VT/VF for deciding to delay a pacing pulse by control circuit 80. In other examples described below, therefore, multiple cardiac signal segments may be buffered and analyzed for determining VT/VF evidence.

When the pacing escape interval 156 is relatively long, as in the example of FIG. 6, control circuit 80 may buffer the cardiac electrical signal 152 over a relatively long time segment 158 for determining VT/VF morphology metrics. The cardiac signal segment may extend up to a processing interval 159 prior to the expiration of the pacing escape interval 156. Processing interval 159 is shown in FIG. 6 to represent the time that may be required for control circuit 80 to process the cardiac signal for determining one or more VT/VF morphology metrics from the cardiac signal segment sensed over time segment 158, determine if VT/VF evidence criteria are met by the VT/VF morphology metrics, and delay the pending pacing pulse if VT/VF evidence in the cardiac signal segment is positively determined. Processing interval 159 may not be shown to scale relative to the time segment 158 in FIG. 6 and may be 10 to 100 ms, or 15 to 20 ms, as examples and may depend on the particular hardware, firmware and/or software implementation of the processing and analysis performed by control circuit 80 for determining VT/VF evidence. Examples of VT/VF morphology metrics determined from the cardiac signal segment are described below, e.g., in conjunction with FIG. 9. In other examples, the processing interval 159 may occur upon expiration of the pacing escape interval 156 such that, when VT/VF evidence is not determined in the cardiac signal segment, the pending pacing pulse 162 may be delivered after a short processing delay (if a Vsense signal determined to be a valid event signal is not received during the pacing escape interval or the processing time interval).

In the example shown, control circuit 80 determines that VT/VF evidence criteria are not met such that the pending pacing pulse 162 (VP) is delivered by therapy delivery circuit 84 upon expiration of the pacing escape interval 156 (when no Vsense signal is received, or valid event signal is identified, during the pacing escape interval 156). Control circuit 80 starts a new pacing escape interval 166 in response to the delivered pacing pulse 162. The new pacing escape interval 166 may be set to a lower rate interval, e.g., 0.8 to 2 seconds or 1 second in the example shown corresponding to a programmed lower rate of 60 ppm.

Control circuit 80 may wait an onset delay interval 161 following pacing pulse 162 and begin buffering the cardiac electrical signal 152 over time segment 168. Onset interval 161 may have the same time duration as onset interval 155 in some examples, independent of the duration of the pacing escape interval that has been started. In other examples, the onset interval 161 may be relatively shorter than onset interval 155, based on the relatively shorter pacing escape interval 166. Time segment 168 may expire at the start of a processing time interval 159 prior to the expiration of the pacing escape interval 166. Control circuit 80 may determine the same VT/VF morphology metrics from the cardiac signal segment sensed over time segment 168 as determined from the relatively long cardiac signal segment sensed over time segment 158. Control circuit 80 may apply the same VT/VF evidence criteria to the VT/VF morphology metrics determined from the relatively shorter cardiac signal segment. In other examples, however, the VT/VF evidence criteria, e.g., one or more thresholds, ranges, or other conditions applied to the VT/VF morphology metrics, may be different when the cardiac signal segment, e.g., sensed or time segment 168, is a relatively shorter cardiac signal segment than when the cardiac signal segment is relatively longer, e.g., sensed over time segment 158.

The confidence in a determination of VT/VF evidence in the relatively shorter cardiac signal segment 168 that can be sensed during the relatively shorter pacing escape interval 166 may be lower than a determination of VT/VF evidence in the relatively longer cardiac signal segment acquired over time segment 158. As such, control circuit 80 may determine different VT/VF morphology metrics and/or apply different VT/VF evidence criteria to a relatively shorter cardiac signal segment in some examples and/or use multiple cardiac signal segments, that may span one or more pacing escape intervals and/or pacing delay intervals, for determining VT/VF evidence. Depending on a given VT/VF morphology metric, such as signal pulse number, a threshold, range or other condition applied to a VT/VF morphology metric may necessarily be adjusted because of the relatively shorter duration of the cardiac signal segment.

In the example shown, VT/VF evidence criteria are not met by the cardiac signal segment sensed during time segment 168 such that therapy delivery circuit 84 delivers the pending cardiac pacing pulse 172 upon the expiration of the pacing escape interval 166. It is to be understood however, that when the VT/VF evidence criteria are met by the cardiac electrical signal sensed during time segment 158 or during time segment 168, control circuit 80 may delay the pending pacing pulse, e.g., by extending the respective pacing escape interval 156 or 166, restarting a pacing escape interval without delivering the pending pacing pulse, or starting a predetermined pacing delay interval.

Figure 7:
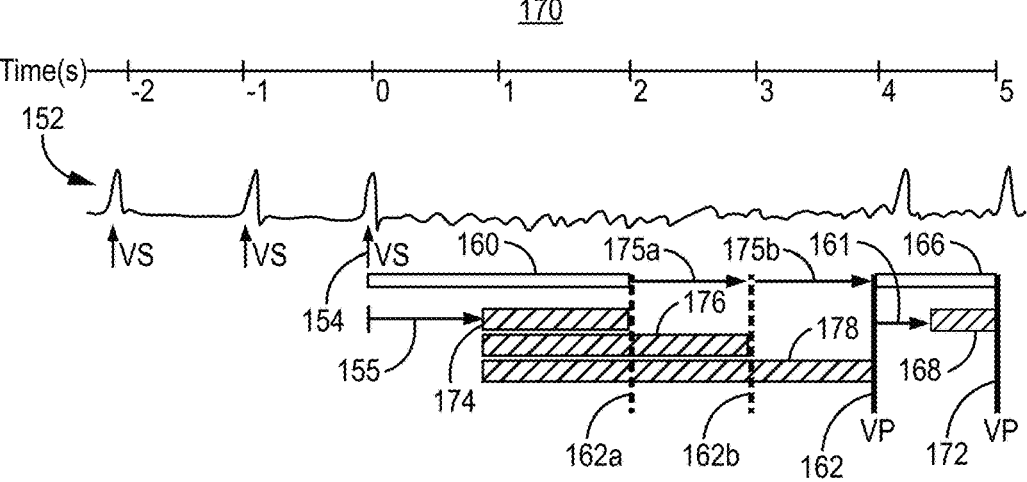
FIG. 7 is a diagram of a method for controlling delivery of cardiac pacing pulses according to another example.

FIG. 7 is a diagram 170 of a method for controlling delivery of cardiac pacing pulses according to another example. In this example, the hysteresis pacing escape interval 160 is set to two seconds and is started by control circuit 80 in response to Vsense signal 154. As described above, Vsense signal 154 may represent a ventricular event sensed by a single sensing channel that is relied on for R-wave sensing for use in controlling bradycardia in some examples. In other examples, Vsense signal 154 may represent a valid event signal identified by control circuit 80 when a Vsense signal is received from both sensing channels 83 and 85 within a validation window of each other and/or a cardiac signal sensed during the validation window started in response to a Vsense signal received from one sensing channel 83 or 85 meets R-wave morphology criteria.

Control circuit 80 may wait for onset delay interval 155 to expire and, in this example, begins buffering cardiac electrical signal 152 over multiple, different time segments 174, 176 and 178. While not illustrated in FIG. 7, it is to be understood that each of time segments 174, 176, 178 may be terminated at a processing time interval 159 prior to the time of a scheduled pending cardiac pacing pulse as shown in FIG. 6.

In the example shown, the first time segment 174 is 1 second, the second time segment 176 is 2 seconds, and the third time segment 178 is 3 seconds. In other examples, multiple different time segments may have different durations than the illustrative example shown. For example, with no limitation intended, the first time segment 174 may be 0.4 to 1.8 seconds and may expire at or just prior to the expiration of the pacing escape interval 160. The second time segment 176 may be 0.8 to 2.8 seconds and may expire at or just prior to the expiration of a pacing delay interval 175a. The third time segment 178 may be 1 second to 3.5 seconds and may expire at or just prior to a second pacing delay interval 175b.

When control circuit 80 determines that the cardiac signal segment sensed over the first time segment 174 meets VT/VF evidence criteria, the pending pacing pulse 162a is delayed by a pacing delay interval 175a, set to one second in this example. Pacing delay interval 175a may be 0.5 to 3 seconds or any other selected interval, e.g., up to a maximum pacing delay of 6 to 9 seconds, in other examples. When the cardiac electrical signal sensed during the second time segment 176 meets the VT/VF evidence criteria, the pending pacing pulse 162b is delayed by a second pacing delay interval 175b. In this example, the first and second pacing delay intervals 175a and 175b are shown to be equal, 1 second intervals. In other examples, a second pacing delay interval 175b may be longer or shorter than the first pacing delay interval 175a. Successive pacing delay intervals may be equal, progressively increased or progressively decreased when control circuit 80 determines VT/VF evidence in successively longer cardiac signal segments 174, 176 and 178. The pending pacing pulse may be delayed by one or more successive pacing delay intervals until a maximum pacing delay is reached, until a Vsense signal is received (or valid event signal is identified) or until arrhythmia detection circuit 92 detects VT/VF and control circuit 80 cancels the pending pacing pulse, whichever comes first.

In the example shown, control circuit 80 determines that VT/VF evidence criteria are not met by the third time segment 178 and delivers the pending pacing pulse 162 upon expiration of the second delay interval 175b. In response to the delivered pacing pulse 162, control circuit 80 may restart a pacing escape interval 166 set to a lower rate interval corresponding to the programmed lower rate. As described above, control circuit 80 may wait an onset delay interval 161 and buffer the cardiac electrical signal 152 over a time segment 168, e.g., 0.4 to 0.8 seconds or 0.5 seconds, leading up to the expiration of the pacing escape interval 166. In this case, VT/VF evidence is not determined from the cardiac signal segment corresponding to time segment 168, and the pending pacing pulse 172 is delivered upon expiration of pacing escape interval 166.

FIG. 7 illustrates that one or more timers for buffering cardiac signal segments of incoming morphology signal 152 may be started by control circuit 80 simultaneously, having different time durations for enabling determination of VT/VF evidence in cardiac signal segments of different durations. When the decision to deliver or delay a pending pacing pulse needs to be made by control circuit 80 before the expiration time of a relatively short pacing escape interval, e.g., 2 seconds or less, the relatively shorter cardiac signal segment contains less information (e.g., fewer ventricular cycles or in some instances only a portion of one ventricular cycle) for determining whether the signal represents a possible VT/VF rhythm. Accordingly, a first pacing delay interval 175a may be applied by control circuit 80 based on analysis of a relatively short cardiac signal segment sensed over time segment 174. A subsequent decision to deliver the pending pacing pulse 162 after the first pacing delay interval 175a may be based on a relatively longer cardiac signal segment sensed over longer time segment 176, which may overlap or encompass the first relatively short time segment 174 of cardiac electrical signal 152 but includes more information, e.g., more ventricular cycles (or lack thereof in the case of bradycardia or asystole), for basing the determination of VT/VF evidence on.

When the pending pacing pulse 162 is delayed a second time, for the second pacing delay interval 175b, control circuit 80 may analyze an even longer cardiac signal segment, sensed over time segment 178. The VT/VF morphology metrics determined from the relatively shorter time segments 174 and 176 of cardiac electrical signal 152 may indicate that the cardiac electrical signal 152 could be VT/VF in this example, such that the pending pacing pulse and subsequently delayed pending pacing pulse (represented by 162a and 162b, respectively) should be delayed again. However, when the longer cardiac signal segment corresponding to time segment 178, having more information than the two relatively shorter cardiac signal segments corresponding to time segments 174 and 176, is analyzed by control circuit 80, VT/VF evidence criteria are not met in this example. The pending pacing pulse 162 is delivered at the expiration of the second pacing delay interval 175b.

While three different time segments 174, 176 and 178 are shown in FIG. 7 for buffering three different durations of cardiac signal segments, it is to be understood that two or more than three different timers may be used by control circuit 80 for buffering cardiac signal segments of different durations for analyzing for VT/VF evidence. Furthermore, separate timers for buffering three (or other selected number) of cardiac signal segments all having the same starting time (after onset delay 155) may not be required. Instead, successively acquired cardiac signal segments may be appended to obtain longer cardiac signal segments. For example, successive cardiac signal segments corresponding to three (or other selected number) 1-second (or other duration) cardiac signal segments may be appended together to obtain the longest cardiac signal segment corresponding to time segment 178. Once the decision to delay pending pacing pulse 162a is made during a processing interval following a shorter cardiac signal segment, buffering of the cardiac electrical signal 152 may continue to obtain the second cardiac signal segment over a relatively longer time segment 176 and so on.

Figure 8:
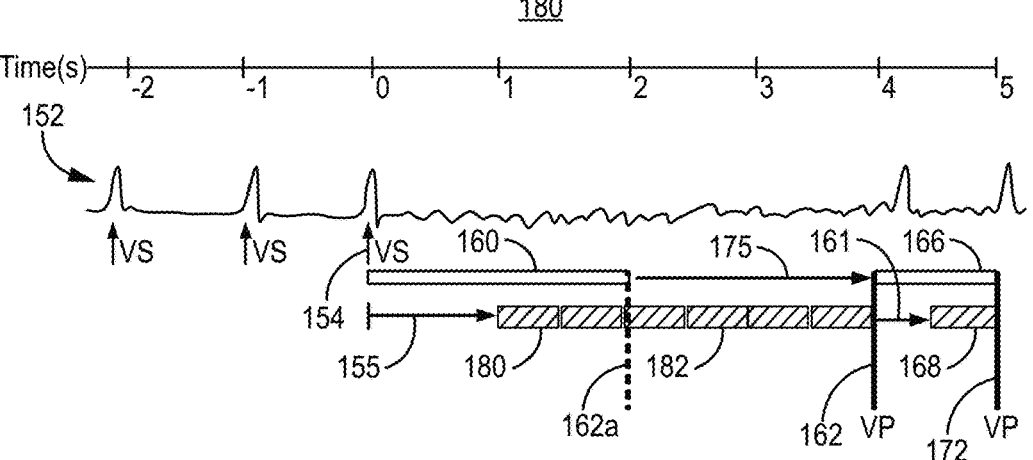
FIG. 8 is a diagram of a method for controlling delivery of cardiac pacing pulses according to yet another example.

While time segments 174, 176 and 178 are shown to all start simultaneously upon expiration of the onset delay interval 155, cardiac signal segments having different time durations may have staggered starting times. Staggered cardiac signal segments of different time durations (or the same time durations) may or may not overlap in time in various examples FIG. 8 is a diagram 180 of a method for controlling delivery of cardiac pacing pulses according to yet another example. In this example, the pacing escape interval 160 is set to a two second hysteresis interval in response to the Vsense signal 154 as described in conjunction with FIG. 7. Cardiac electrical signal 152, however, is buffered over multiple consecutive time segments 180 following an onset delay interval 155 until a processing time interval (e.g., processing time interval 159 as shown in FIG. 6) prior to the expiration of pacing escape interval 160. In this example, each time segment 180 is 0.5 seconds, however longer or shorter time segments, e.g., 0.3 to 0.8 seconds, may be used for buffering the cardiac electrical signal 152 during multiple sequential signal segments.

Control circuit 80 may determine VT/VF morphology metrics from each time segment 180, e.g., according to any of the techniques described below. Control circuit 80 may determine that VT/VF evidence criteria are met by the first two cardiac signal segments leading up to the expiration of the pacing escape interval 160. In this case, the pending pacing pulse 162a may be delayed. In order to determine VT/VF evidence, control circuit 80 may require that at least two cardiac signal segments meet VT/VF evidence criteria and/or at least the most recent cardiac signal segment meets the VT/VF evidence criteria. In response to determining evidence of VT/VF in cardiac signal segments 180 during pacing escape interval 160, control circuit 80 may delay the pending pacing pulse 162a by a pacing delay interval 175, which is equal to the 2 second hysteresis interval in the example shown but may be set to longer or shorter delay intervals. It is to be understood that pending pacing pulses 162a, 162b shown by dashed lines in FIGS. 7 and 8 are scheduled but not delivered due to VT/VF evidence being determined during the respective preceding pacing escape interval or pacing delay interval.

Control circuit 80 continues to buffer and analyze cardiac signal segments sensed during consecutive time segments 182 during the pacing delay interval 175. In the example, shown, when each time segment 182 is 0.5 seconds and the delay interval 175 is 2 seconds, control circuit 80 may analyze four cardiac signal segments by determining VT/VF morphology metrics from each signal segment that are compared to VT/VF evidence criteria. It is recognized that each time segment 182 may be slightly less than 0.5 seconds or the last time segment prior to the expiration of the pacing delay interval 175 may be less than 0.5 seconds to allow time for the processing interval 159 (shown in FIG. 6) prior to the expiration of the delay interval 175. In other examples, two or more of the time segments 182 may overlap slightly to allow for a processing interval 159 upon the expiration of the pacing delay interval 175. Alternatively, the pacing delay interval 175 may be slightly longer than the duration of the four 0.5 second cardiac signal segments to be analyzed for determining VT/VF evidence to account for processing time required for deciding whether to further delay or deliver the pending pacing pulse.

Control circuit 80 may determine if at least two out of four, at least three out of four, or at least four out of four, and/or at least the most recent cardiac signal segment ending just prior to the expiration of the pacing delay interval 175 meet VT/VF evidence criteria. In some examples, all cardiac signal segments corresponding to time segments 182, e.g., four out of four, during the pacing delay interval 175 may be required to meet the VT/VF evidence criteria. In still other examples, control circuit 80 may require a threshold number out of all of the cardiac signal segments sensed during time segments 180 and 182 that have elapsed since the expiration of the onset delay interval 155 (a total of six in this example) meet the VT/VF evidence criteria. For instance, two out of six, three out six, four out of six, or five out of six, including the most recent cardiac signal segment sensed just prior to the expiration of the pacing delay interval 175, may be required to meet VT/VF evidence criteria in order to determine evidence of VT/VF and further delay the pending pacing pulse 162. When the requisite number of cardiac signal segments sensed during pacing escape interval 160 and/or pacing delay interval 175 meet VT/VF evidence criteria, control circuit 80 may delay the pending cardiac pacing pulse 162 for another pacing delay interval, if a maximum pacing delay has not been reached.

In the example shown in FIG. 8, however, control circuit 80 determines that the requisite number of cardiac signal segments do not meet VT/VF evidence criteria, or the most recent cardiac signal segment corresponding to the latest time segment 182 before expiration of pacing delay interval 175 does not meet VT/VF evidence criteria. As such, pending pacing pulse 162 is delivered at the expiration of the pacing delay interval 175. The next pacing escape interval 166 is started, set to a lower rate interval of 1 second in the example shown. After an onset delay interval 161, the cardiac electrical signal 152 sensed over time segment 168 is buffered and evaluated by control circuit 80 for determining VT/VF evidence. If VT/VF evidence is determined, control circuit 80 may delay the pending pacing pulse 172. In the example shown, VT/VF evidence is not determined in the cardiac electrical signal 152 sensed during the pacing escape interval 166, and pending pacing pulse 172 is delivered at the expiration of pacing escape interval 166.

FIG. 8 illustrates that multiple, successive cardiac signal segments may be analyzed for determining if a threshold number of cardiac signal segments meet VT/VF evidence criteria for determining whether to delay or deliver a pending pacing pulse. In some instances, the threshold number of cardiac signal segments may occur within one pacing escape interval or one pacing delay interval. In other instances, the threshold number of cardiac signal segments may span across the pacing escape interval and/or one or more pacing delay interval(s). In the illustrative example of FIG. 8, the cardiac signal segments 180 meeting VT/VF evidence criteria and occurring before the expiration of the pacing escape interval 160 may be counted toward the required number of cardiac signal segments meeting VT/VF evidence criteria for further delaying the pending pacing pulse 162 for a second delay interval when pacing delay interval 175 expires. Furthermore, any of the six cardiac signal segments sensed during time segments 180 and time segments 182 that meet VT/VF evidence criteria may be counted toward determining VT/VF evidence for delaying the pending pacing pulse a third time, during a third pacing delay interval (not illustrated in the example of FIG. 8) after pacing delay interval 175.

Figure 9:
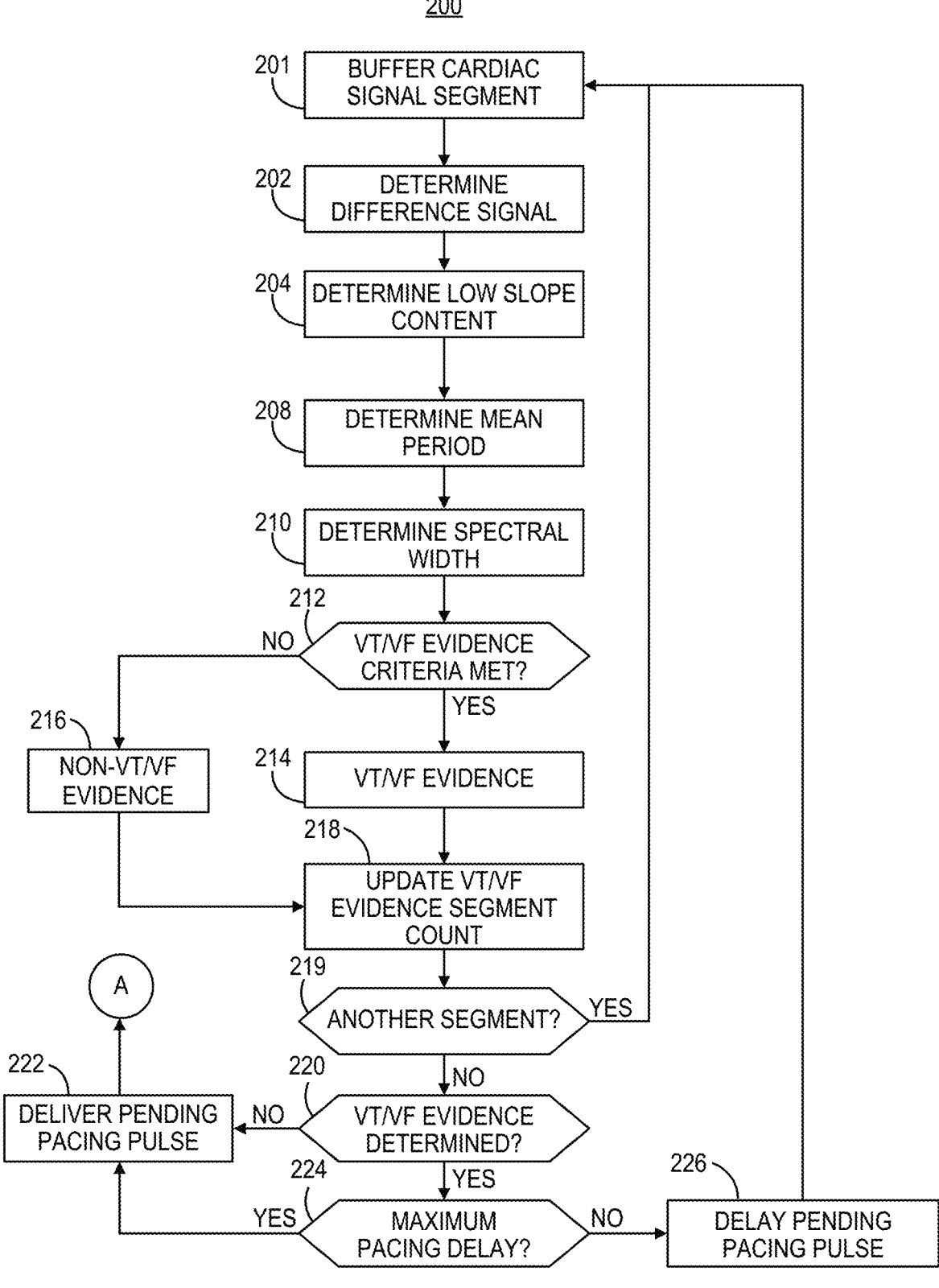
FIG. 9 is a flow chart of a method for determining VT/VF morphology metrics and determining evidence of VT/VF in a cardiac electrical signal according to some examples.

FIG. 9 is a flow chart 200 of a method for determining VT/VF morphology metrics and determining evidence of VT/VF in cardiac signal segments according to some examples. Control circuit 80 may determine one or more VT/VF morphology metrics from each cardiac signal segment acquired during a pacing escape interval and/or subsequent pacing delay interval. Each VT/VF morphology metric may be determined to enable control circuit 80 to discriminate between cardiac signal characteristics during VT/VF versus during non-VT/VF.

The process of flow chart 200 may be performed following a Vsense signal, which may be received from a single sensing channel when one sensing channel is used for sensing R-waves or a Vsense signal that is determined to be a valid event signal when two (or more) sensing channels are used for sensing R-waves as described in the above-incorporated U.S. Patent Application Nos. 63/251,803, 63/251,820 and U.S. Ser. No. 17/822,681. In general, any signal indicating the time of a ventricular intrinsic event (e.g., R-wave), in accordance with any sensing algorithm, that causes control circuit 80 to start a pacing escape interval may initiate the process of flow chart 200. The process of flow chart 200 is performed by control circuit 80 for analyzing a cardiac electrical signal received from sensing circuit 86 during the subsequent pacing escape interval that is started in response to the signal indicative of a ventricular intrinsic event and during any pacing delay intervals that are started following the pacing escape interval. As described below, the process of determining VT/VF evidence for delaying a pending pacing pulse that is scheduled following a signal indicative of an intrinsic R-wave may be different than the process of determining VT/VF evidence for delaying a pending pacing pulse that is scheduled following a delivered pacing pulse in some examples. Methods for determining VT/VF evidence during a pacing escape interval started in response to a delivered pacing pulse are described below in conjunction with FIGS. 14 and 15.

In response to sensing a ventricular event signal, control circuit 80 may buffer a cardiac signal segment at block 201, which may be sampled at 128 or 256 Hz, as examples. As described above, the cardiac signal segment may be received from the morphology signal channel 87 and may be a bandpass and notch filtered signal. In some examples, control circuit 80 may perform additional signal processing, e.g., filtering, before determining VT/VF morphology metrics. In some examples, control circuit 80 may determine a gradient signal of the cardiac signal segment, at block 201, e.g., using a central difference method, prior to calculating VT/VF morphology metrics from the cardiac electrical signal for determining evidence of VT/VF. Additionally or alternatively, control circuit 80 may be configured to filter the cardiac signal segment using a bandpass filter, such as a 2 to 40 Hz, 2 to 35 Hz, 3 Hz to 32 Hz or a 3 to 23 Hz bandpass filter as examples. The cardiac signal segment may be buffered starting from the expiration of an onset delay interval as generally described above, e.g., in conjunction with FIG. 6.

At block 202, control circuit 80 may determine a first order difference signal that is rectified for determining the VT/VF morphology metrics of low slope content (LSC) at block 204, mean period at block 208, and spectral width (SW) at block 210 from the cardiac signal segment, in this example. While these VT/VF morphology metrics are shown in flow chart 200 to be determined in a certain order, it is recognized that VT/VF morphology metrics may be determined in a different order than shown and/or determined simultaneously in parallel processing methods. In some examples one or more of these VT/VF morphology metrics may not be determined and may be omitted from the analysis of the cardiac signal segment. Each of the VT/VF morphology metrics that are determined may be determined from sample points spanning the entire cardiac signal segment.

The LSC may be determined at block 204 as the total number of sample points of the rectified, first order difference signal that have an amplitude less than a low slope amplitude threshold. Control circuit 80 may establish the low slope amplitude threshold based on a maximum peak amplitude of the first order difference signal determined from the cardiac signal segment or based on multiple local maximum peak amplitudes determined from multiple subsegments of the first order difference signal determined from the cardiac signal segment.

For example, control circuit 80 may divide the cardiac signal segment into four subsegments and determine the local maximum amplitude of each subsegment. When a local maximum amplitude is less than a percentage, e.g., 20%, of the overall maximum peak amplitude of the rectified first order difference signal, the overall maximum peak amplitude may be substituted for the local maximum amplitude. The low slope amplitude threshold may be set to a percentage or fraction of the mean of the local maximum amplitudes. In one example, the low slope amplitude threshold is set to between 5% and 10% or about one-sixteenth of the mean of the local maximum amplitudes. When the cardiac signal segment is relatively short, e.g., 0.5 seconds, the low slope amplitude threshold may be set to one-sixteenth (or other percentage) of the overall maximum peak amplitude of the cardiac signal segment without determining multiple local maximum amplitudes.

Once the low slope amplitude threshold is established, control circuit 80 may sum all of the sample points of the rectified difference signal that have an amplitude that is less than or equal to the low slope amplitude threshold. Control circuit 80 may determine the LSC by dividing the sum by the total number of sample points in the cardiac signal segment. In other examples, a LSC may be determined for each one of multiple subsegments of the cardiac signal segment, e.g., by summing all sample points of the rectified difference signal having an amplitude less than or equal to the low slope amplitude threshold and dividing by the total number of sample points in the subsegment. The LSC of the overall cardiac signal segment may be determined as the average of the subsegment LSCs.

Additionally or alternatively, control circuit 80 may determine the mean period of the cardiac signal segment at block 208. The mean period may be determined by control circuit 80 as the inverse of the mean frequency of the cardiac signal segment, which is an estimate of the center frequency of the cardiac signal segment. The mean frequency may be determined by control circuit 80 as the ratio of the average absolute amplitude of the rectified first order difference signal (sum of all sample point amplitudes of the rectified difference signal divided by total number of sample points) to the average absolute amplitude of the rectified cardiac signal segment (sum of all sample point amplitudes of the rectified cardiac signal segment divided by total number of sample points). As such, the mean period may be estimated as the ratio of the sum of all sample point amplitudes of the rectified cardiac signal segment to the sum of all sample point amplitudes of the rectified first order difference signal of the cardiac signal segment. The mean period may optionally be converted to a radian measure by multiplying this ratio by the factor $2\pi/(\text{sampling frequency})$.

Control circuit 80 may use the mean period for determining the spectral width (SW) at block 210. Control circuit 80 may determine the SW as the fundamental period of the cardiac signal segment less the mean period. In some examples, control circuit 80 may determine the fundamental period as the mean of signal peak intervals that are determined between identified signal peaks. A method for identifying signal peaks and determining signal peak intervals is described below in conjunction with FIGS. 14A and 14B. In some examples, the fundamental period may be determined as a trimmed mean, e.g., by removing one or more longest and/or one or more of the shortest peak intervals between the signal peaks identified from the rectified difference signal determined from the cardiac signal segment. The SW may be determined by control circuit 80 by subtracting the mean period determined at block 208 from the fundamental period. When no peak intervals are determinable from the cardiac signal segment, e.g., when only one signal peak is identified from the cardiac signal segment, control circuit 80 may set the fundamental period nominally to 0. Control circuit 80 may then determine the SW to be equal to the negative value of the mean period (SW equals fundamental period minus mean period). In other examples, the fundamental period used to determine SW may be determined from one or more signal peak intervals that span two or more consecutive cardiac signal segments. Example techniques for determining the LSC, mean period and SW from cardiac signal segments that may be adapted for determining VT/VF evidence from a cardiac signal segment that is sensed during a pacing escape interval are generally described in the above-incorporated U.S. Patent Application No. 63/278,955 and corresponding U.S. patent application Ser. No. 18/045,135 and in U.S. Pat. No. 8,301,233 (Zhang, et al.), incorporated herein by reference in its entirety.

At block 212, control circuit 80 may determine if the VT/VF morphology metrics of the cardiac signal segment meet VT/VF evidence criteria. In some examples, the LSC, mean period, and/or SW may each be compared to respective thresholds for determining VT/VF evidence. As described below in conjunction with FIGS. 10-12, each of the LSC, SW and mean period may be useful discriminators between VT/VF rhythms and non-VT/VF rhythms. In an illustrative example, when the mean period is at least 60 ms, the SW is less than or equal to −2 ms and the LSC is less than or equal to 0.52 (52%), control circuit 80 may determine VT/VF evidence for the cardiac signal segment at block 214. When the mean period is less than 60 ms or the SW is greater than −2 ms or the LSC is greater than 0.52, control circuit 80 may determine no VT/VF evidence for the cardiac signal segment at block 216. In another example, when the mean period is at least 60 ms and the SW normalized by mean period (SW/mean period) is less than or equal to 0.085 and greater than −1, the morphology metrics of the cardiac signal segment may be determined to meet VT/VF evidence at block 212. These example thresholds and ranges defining VT/VF evidence criteria are illustrative in nature and not intended to be limiting. Other example thresholds or other conditions that define VT/VF evidence criteria are listed below in conjunction with FIGS. 10-12.

In other examples, control circuit 80 may determine evidence of VT/VF for the cardiac signal segment when the LSC is less than a threshold set as a linear function of the SW. Accordingly, in some examples the VT/VF segment criteria requires that the LSC be less than a factor of the SW plus an offset. When LSC is plotted as a function of SW, a linear relationship between LSC and SW may discriminate VT/VF rhythm segments from non-VT/VF rhythm segments. In one example, control circuit 80 determines that the cardiac signal segment is evidence of VT/VF when the LSC falls below the line defined by m*SW+b where m is −0.05 and b is 1.16 in an example. The slope m and the y-intercept b of the linear function of SW may be selected based on patient data to yield a high specificity for determining evidence of VT/VF vs. non-VT/VF.

At block 218, control circuit 80 may update a VT/VF evidence segment count. In some examples control circuit 80 may determine VT/VF evidence for delaying a pending pacing pulse based on multiple cardiac signal segments. At block 218, a count of cardiac signal segments that are identified as VT/VF evidence out of all cardiac signal segments determined during the current pacing escape interval and/or pacing delay interval(s) can be updated by control circuit 80 based on the determination of no VT/VF evidence for the current cardiac signal segment at block 216 or the positive determination of VT/VF evidence at block 214. Control circuit 80 may determine if all cardiac signal segments available for analysis prior to expiration of the current pacing escape interval or pacing delay interval have been analyzed at block 219. When another cardiac signal segment can be buffered prior to the scheduled pending pacing pulse, control circuit 80 may return to block 201 for acquiring and analyzing the next cardiac signal segment.

When all available cardiac signal segments prior to expiration of the current pacing escape interval and/or pacing delay interval have been analyzed ("no" branch of block 219), control circuit 80 may advance to block 220 to determine if VT/VF evidence is determined in a requisite number (and temporal location relative to the scheduled pending pacing pulse) of the cardiac signal segments. When a threshold number of consecutive or non-consecutive cardiac signal segments (which may be only one out of one in some instances) are determined to be VT/VF evidence ("yes" branch of block 220), therapy delivery circuit 84 may delay the pending pacing pulse at block 226.

In some examples, control circuit 80 may determine whether to deliver or delay a pending cardiac pacing pulse based on analysis of a single cardiac signal segment prior to expiration of the pacing escape interval (e.g., as depicted in FIG. 6). In this case, blocks 218, 219 and 220 may be omitted. Control circuit 80 may advance directly to block 222 to deliver the pending pacing pulse when the single cardiac signal segment is determined to be no VT/VF evidence at block 216 or directly to block 224 when the single cardiac signal segment is determined to be VT/VF evidence at block 214.

When VT/VF evidence is determined, based on one or more cardiac signal segments, control circuit 80 may determine whether a maximum pacing delay has been reached at block 224. In some examples, control circuit 80 may delay a pending pacing pulse up to a maximum pacing delay, which may be four to nine seconds as examples. If a maximum pacing delay has not been reached, as determined at block 224, control circuit 80 may delay the pending pacing pulse at block 226. Control circuit 80 may start a pacing delay interval and return to block 201 to begin buffering the next cardiac signal segment. When the maximum pacing delay has been reached as determined at block 224, control circuit 80 may deliver the pending pacing pulse at block 222. If a valid Vsense signal has not been received from sensing circuit 86 and a VT/VF detection has not been made by arrhythmia detection circuit 92 during the maximum pacing delay, therapy delivery circuit 84 may deliver the pending pacing pulse at block 222 since a true asystole (or bradycardia or long pause) may be present.

Referring again to block 220, control circuit 80 may determine that VT/VF evidence criteria are not met for withholding the pending pacing pulse when less than a threshold number of the cardiac signal segments are determined to be VT/VF evidence, and/or when the most recent cardiac signal segment is determined as non-VT/VF evidence (at block 216) based on the morphology metrics, e.g., LSC, mean period and/or SW of the cardiac signal segment(s) analyzed. Control circuit 80 may determine that there is not sufficient evidence of a potential VT/VF rhythm to warrant withholding the pending pacing pulse. Therapy delivery circuit 84 may deliver the pending pacing pulse at block 222.

While not explicitly shown in FIG. 9, it is to be understood that when control circuit 80 receives a Vsense signal from sensing circuit 206 any time prior to the expiration of the pacing escape interval or a subsequent pacing delay interval (including the processing time interval), control circuit 80 may terminate the process of analyzing the cardiac signal segment(s) and return to block 201 without delivering the pending pacing pulse at block 222. The Vsense signal may be received from a single sensing channel or identified as a valid event signal when two sensing channels are included in sensing circuit 204 (e.g., as generally disclosed in the above-incorporated provisional U.S. Patent Application No. 63/251,803, provisional U.S. Patent Application No. 63/251,820 and corresponding U.S. patent application Ser. No. 17/822,681). The pending pacing pulse may be inhibited, and the next pacing pulse may be scheduled by starting a new pacing escape interval in response to a valid Vsense signal. The next cardiac signal segment may be buffered during the new pacing escape interval at block 201 for subsequent analysis and the process of flow chart 200 may be repeated.

Figure 16:
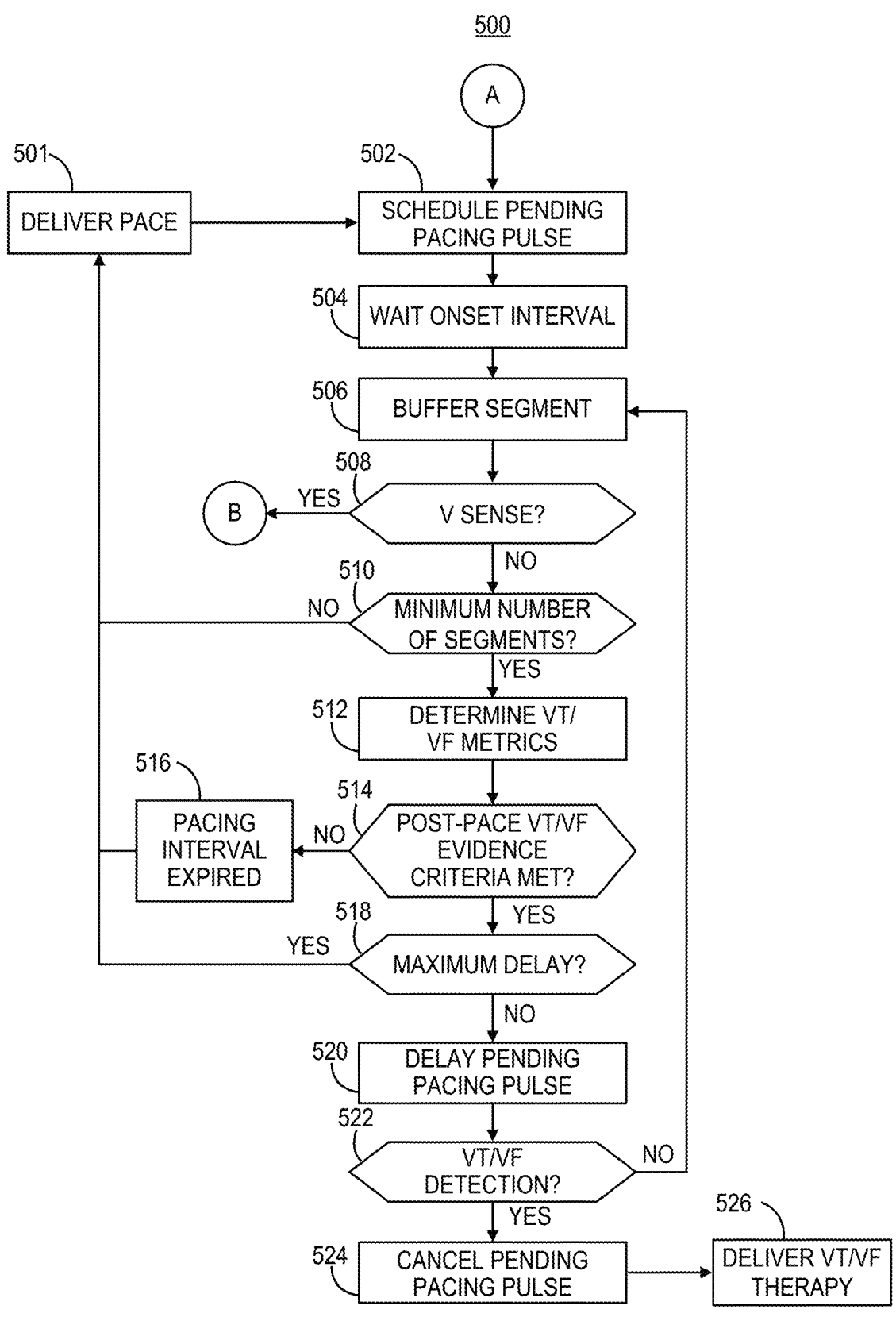
FIG. 16 is a flow chart of a method for controlling the delivery of cardiac pacing pulses scheduled at pacing escape intervals started in response to delivered pacing pulses according to some examples.

Once a pending pacing pulse is delivered at block 222, control circuit 80 may advance to the process of flow chart 500 shown in FIG. 16, as indicated by connector "A." The process of analyzing cardiac signal segments for deciding to delay or withhold a pacing pulse after pacing has begun may be different than the process of flow chart 200, which may be performed following a signal indicative of a valid, sensed intrinsic ventricular event. As such, the pacing pulse delivered at block 222 may be the first pacing pulse since a Vsense signal has been received from sensing circuit 86 (or a valid event signal has been identified) by control circuit 80. Control circuit 80 may perform a different process for determining when to delay a pending pacing pulse that has been scheduled at a pacing escape interval started in response to delivery of a preceding pacing pulse.

Figure 10:
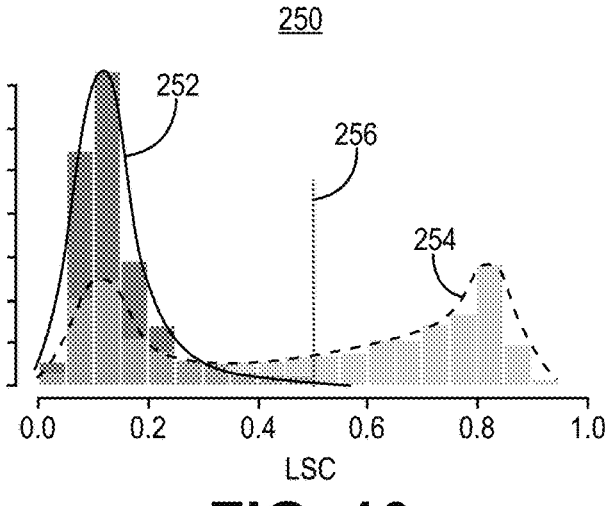
FIG. 10 is a plot of an example frequency distribution of values of the low slope content (LSC) determined from cardiac signal segments that are received during VT/VF rhythms and from cardiac signal segments that are received during non-VT/VF rhythms.

FIG. 10 is a plot 250 of the frequency distribution of values of the LSC determined from cardiac signal segments that are received during VT/VF and from cardiac signal segments that are received during non-VT/VF rhythms. In this example, the cardiac signal segments are 0.5 seconds in duration. It is recognized than when the cardiac signal segments are a different duration, the distribution of values of the LSC may be different than the example shown in FIG. 10.

The LSCs of signal segments received during VT/VF are shown by the approximated frequency distribution curve 252. The LSCs of signal segments received during non-VT/VF rhythms are shown by the approximated frequency distribution curve 254. As observed in FIG. 10, LSC is a relatively sensitive discriminator between VT/VF and non-VT/VF cardiac signal segments. In the example shown, the frequency distribution curve 254 corresponding to non-VT/VF cardiac signal segments is observed to include two peaks, around 0.1 and around 0.85. Multiple peaks in the non-VT/VF frequency distribution may arise because cardiac signal segments sensed during non-VT/VF rhythms may include multiple types of rhythms or conditions, such as normal sinus rhythm, sinus tachycardia, supraventricular tachyarrhythmias, noise contaminated cardiac electrical signals, relatively large T-waves, relatively large P-waves, ectopic or aberrantly conducted beats, etc.

A LSC threshold, however, for discriminating between VT/VF rhythms and non-VT/VF rhythms may be set between 0.15 and 0.5, as examples. A hypothetical LSC threshold 256 of 0.52 (e.g., 52% of all sample points are less than the low slope amplitude threshold) is shown. When the LSC is less than the threshold 256, control circuit 80 may determine evidence of VT/VF in a cardiac signal segment sensed during a pacing escape interval (or subsequent pacing delay interval) with a relatively high specificity.

Figure 11:
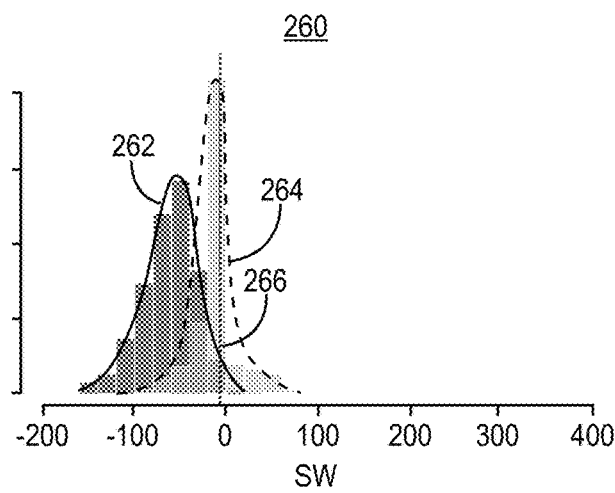
FIG. 11 is a plot of an example frequency distribution of values of spectral width (SW) determined from cardiac signal segments that are sensed during VT/VF rhythms and during non-VT/VF rhythms.

FIG. 11 is a plot 260 of the frequency distribution of values of SW that occur during VT/VF signal segments as shown by the approximated frequency distribution curve 262 and during non-VT/VF signal segments as shown by the approximated frequency distribution curve 264. As observed in FIG. 11, SW is a relatively sensitive discriminator between VT/VF and non-VT/VF cardiac signal segments. A hypothetical SW threshold 266 of −2 that discriminates between VT/VF signal segments and non-VT/VF signal segments with a relatively high degree of specificity is shown. The SW threshold 266 may be between −80 and 0 ms in various examples. The SW can be negative or a very low value during VT/VF because the fundamental period, estimated as a mean signal peak interval as described below, is nearly equal to or less than the mean period of the signal segment. The SW, therefore, can be negative during VT/VF intervals. Noise contaminated signal segments and asystole signal segments are likely to have a relatively larger, positive SW.

Figure 12:
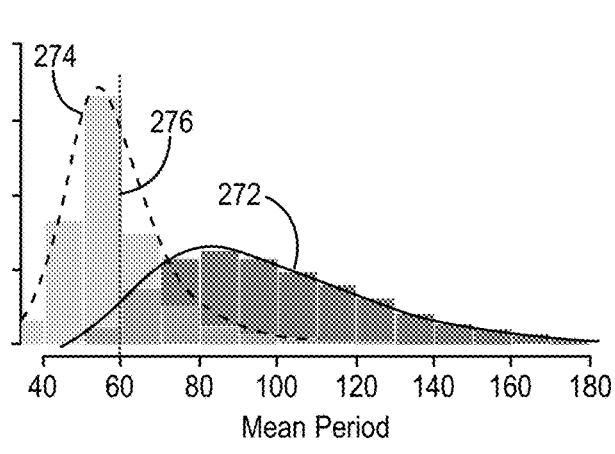
FIG. 12 is a plot of an example frequency distribution of values of mean period that are determined from non-VT/VF cardiac signal segments and from VT/VF cardiac signal segments.

FIG. 12 is a plot 270 of the frequency distribution of values of mean period that can be determined from VT/VF signal segments as shown by the approximated frequency distribution curve 272 and determined from non-VT/VF signal segments as shown by the approximated frequency distribution curve 274. As observed in FIG. 12 the mean period can be used as one VT/VF morphology metric determined from cardiac signal segments for discriminating between evidence of VT/VF and non-VT/VF cardiac signal segments. A hypothetical mean period threshold 276 that discriminates between evidence of VT/VF signal segments and non-VT/VF signal segments with a high sensitivity and specificity is shown. The mean period threshold may be between 50 and 100 ms and is 60 ms in an example.

The cardiac signal segment VT/VF morphology metrics of LSC, SW and/or mean period may be used alone or in combination for determining evidence of VT/VF in a cardiac signal segment based on comparisons to respective individual thresholds, e.g., thresholds 256, 266 and 276 as shown in FIGS. 10, 11 and 12 in some examples. For example, when at least two or when all three metrics meet a VT/VF threshold requirement, VT/VF evidence may be determined to be present in the cardiac signal segment. When any one of the LSC, SW or mean period does not meet a VT/VF threshold requirement, no VT/VF evidence may be determined for the cardiac signal segment. The LSC threshold 256 (FIG. 10), SW threshold 266 (FIG. 11) and mean period threshold 276 (FIG. 12) may each be selected to provide an overall high specificity for detecting evidence of VT/VF in a cardiac signal segment. The thresholds 256, 266 and 276 may be selected in a manner that yields high specificity of VT/VF evidence determinations when all three VT/VF morphology metrics of LSC, SW and mean period are used in combination. In some examples, at least one threshold may be selected to provide high sensitivity while another threshold may be selected to provide high specificity to detecting VT/VF evidence in a cardiac signal segment. In other examples, a linear function between two of the metrics, such as between LSC and SW, may be defined for determining a signal segment as VT/VF evidence. In still other examples, a three-dimensional relationship between LSC, SW and mean period may be determined for defining VT/VF evidence criteria.

Other combinations of morphology metrics may include determining ratios, differences, or other relationships of the morphology metrics. For example, the ratio of SW to mean period may be compared to a respective threshold for determining VT/VF evidence from a cardiac signal segment in some examples. When the mean period is at least 60 ms and the SW/mean period ratio is less than or equal to 0.1, for example, the cardiac signal segment may be determined to be VT/VF evidence. In another example, when the mean period is at least 60 and the SW/mean period ratio is less than or equal to a variable threshold that may be defined as a function of the mean period, the cardiac signal segment may be determined to be VT/VF evidence. In an illustrative example, when SW/mean period ratio is less than 0.085 and greater than −1, and the MP is at least 60 ms for a 0.5 second segment, the cardiac signal segment may be determined to be VT/VF evidence. Other thresholds may be defined depending on the time length of the cardiac signal segment for reliably discriminating between the morphology metrics of VT/VF evidence and a non-VT/VF evidence based on mean period and the SW normalized by mean period. The combination of mean period and SW normalized by mean period as morphology metrics used for determining VT/VF evidence in a cardiac signal segment may reliably detect evidence of VT/VF without requiring determining LSC from the cardiac signal segment. It is recognized, however, that numerous criteria may be conceived for determining evidence of VT/VF from a cardiac signal segment sensed during a pacing escape interval or a pacing delay interval using a variety of combinations of LSC, mean period and/or SW, one or more rate metrics, and/or one or more noise metrics as further described below. Such combinations may include mathematical combinations of two or more metrics (e.g., SW normalized by mean period). VT/VF evidence criteria may include one or more thresholds applied to a respective metric or mathematical combination of metrics where each threshold can be defined as a constant or as a function, e.g., a linear function, of a metric determined from the cardiac signal segment.

In particular, the VT/VF morphology metrics, e.g., LSC, SW, and/or mean period, may be compared to thresholds for discriminating between VT/VF and asystole with a high degree of certainty. For example, in some cases, noise pulses and/or large P-waves may be present in the cardiac signal segment when ventricular asystole is occurring (e.g., during atrioventricular block). The VT/VF morphology metrics and corresponding threshold(s) are selected to discriminate between a noisy signal during asystole and true VT/VF when low amplitude fibrillation waves may be undersensed by sensing circuit 86.

In some examples, arrhythmia detection circuit 92 may analyze cardiac signal segments for detecting VT/VF for controlling tachyarrhythmia therapy delivery by therapy delivery circuit 84. The duration of cardiac signal segments, the VT/VF morphology metrics and/or the VT/VF detection criteria applied to the VT/VF morphology metrics used for detecting VT/VF for controlling tachyarrhythmia therapy delivery may be different than the duration of the cardiac signal segments, the VT/VF morphology metrics and/or VT/VF evidence criteria applied to determine evidence of VT/VF for controlling bradycardia pacing therapy. For example, arrhythmia detection circuit 92 may be configured to determine the LSC, SW and mean period from cardiac signal segments for detecting VT/VF that may be buffered over the same or different time segments as cardiac signal segments analyzed by control circuit 80 for controlling pacing pulse delivery.

The thresholds or other conditions applied to the LSC, SW, and/or mean period by arrhythmia detection circuit 92 for detecting VT/VF for controlling delivery of a tachyarrhythmia therapy, e.g., ATP therapy or a CV/DF shock, may be different than the thresholds or other conditions applied to the LSC, SW, and/or mean period for determining VT/VF evidence for delaying a pending cardiac pacing pulse that is scheduled for treating a too slow or absent ventricular depolarization rate, e.g., a heart rate slower than a programmed lower rate or applied hysteresis interval. In order to determine evidence of VT/VF with acceptable specificity and/or sensitivity, the thresholds or other criteria applied to VT/VF morphology metrics determined from relatively short cardiac signal segments sensed during a pacing escape interval (or pacing delay interval) may be set differently than thresholds or other criteria applied to the same VT/VF morphology metrics (e.g., LSC, SW and mean period) that are determined over relatively longer cardiac signal segments for detecting VT/VF. In some examples, thresholds applied to VT/VF morphology metrics for detecting VT/VF may be selected to achieve a relatively higher sensitivity and/or specificity for detecting VT/VF than the thresholds applied to VT/VF morphology metrics for determining evidence of VT/VF for controlling bradycardia pacing in some examples. Relatively lower sensitivity and/or specificity may be acceptable for determining evidence of VT/VF for controlling bradycardia pacing. Examples of techniques for detecting VT/VF for controlling tachyarrhythmia therapies based on the VT/VF morphology metrics of LSC, SW and mean period are generally disclosed in the above-incorporated U.S. Patent Application No. 63/278,955 and corresponding U.S. patent application Ser. No. 18/045,135.

Figure 13:
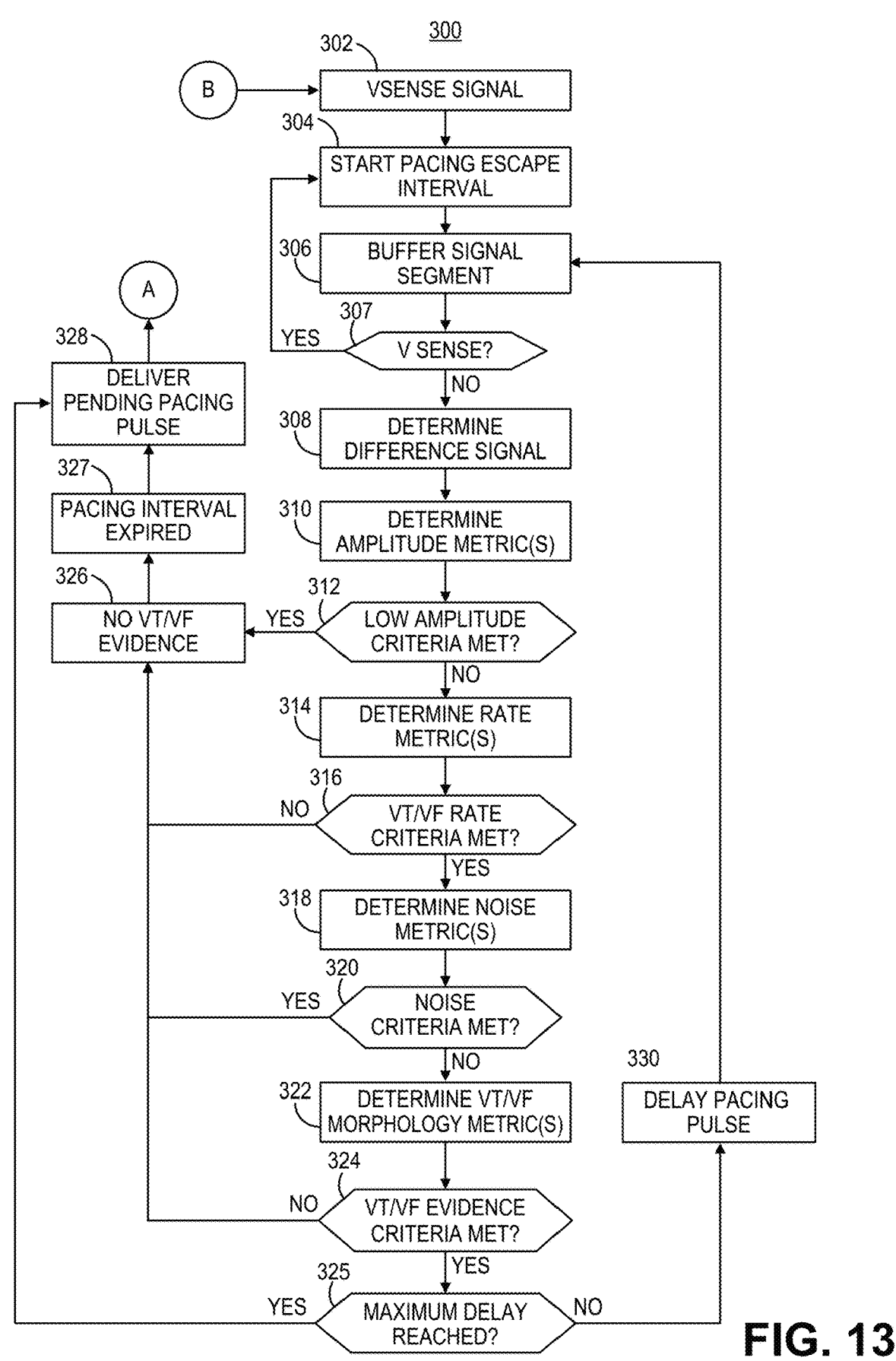
FIG. 13 is a flow chart of a method for determining VT/VF evidence according to another example.

FIG. 13 is a flow chart 300 of a method for determining VT/VF evidence in cardiac signal segments according to another example. Flow chart 300 may be performed during a pacing escape interval and/or pacing delay interval started in response to a Vsense signal sensed at block 302 for determining whether to delay or deliver a pending cardiac pacing pulse. As described above, the Vsense signal sensed at block 302 may be determined to be a valid event signal based on receiving a Vsense signal from two sensing channels 83 and 85 within a validation window from each other and/or a cardiac signal sensed during the validation window meeting R-wave morphology criteria. The pending pacing pulse is scheduled by starting the pacing escape interval at block 304 in response to the Vsense signal (or valid event signal determination).

At block 306, control circuit 80 may buffer one or more cardiac signal segments, e.g., according to any of the examples described above in conjunction with FIGS. 6-8. If control circuit 80 receives a valid Vsense signal as indicated at block 307, at any time during the pacing escape interval or a subsequent pacing delay interval (including during a processing time interval), control circuit 80 may inhibit the pending pacing pulse and return to block 304 to start a new pacing escape interval. In some examples, the currently buffered cardiac signal segment may be discarded, and any analysis of the cardiac signal segment may be aborted. A new cardiac signal segment may be buffered at block 306 after starting the new pacing escape interval.

At block 308 control circuit 80 may determine a rectified difference signal from each cardiac signal segment for determining VT/VF morphology metrics. As described above, in some examples, control circuit 80 may determine a gradient signal, e.g., using a central difference method, followed by bandpass filtering prior to determining the difference signal from the cardiac signal segment. As such, the cardiac signal segment from which the various VT/VF morphology metrics are determined for determining VT/VF evidence may be a rectified, difference signal determined from the bandpass filtered, gradient signal of the cardiac signal segment. Determination of the gradient signal can accentuate differences in the VT/VF morphology metrics determined from VT/VF rhythm segments and non-VT/VF rhythm segments.

Control circuit 80 may delay a pending cardiac pacing pulse based on determining VT/VF evidence when a requisite number of cardiac signal segments are determined to be VT/VF evidence segments. For the sake of convenience, the analysis performed for determining VT/VF evidence is described in conjunction with FIG. 13 as being performed on one cardiac signal segment during the pacing escape interval or a subsequent pacing delay interval for making the decision to delay or deliver the pending pacing pulse. It is to be understood however, that two or more cardiac signal segments buffered during the pacing escape interval and/or one or more subsequent pacing delay intervals may be analyzed for determining evidence of VT/VF as described in any of the examples given above, e.g., in conjunction with FIGS. 6-8.

At block 310, control circuit 80 may determine an amplitude metric from the cardiac signal segment. The amplitude metric may be determined by identifying signal peaks during the cardiac signal segment and determining a representative signal peak amplitude from the signal peaks. The representative signal peak amplitude may be a maximum, minimum, mean, median, trimmed mean or median or other representative value of the absolute amplitude of signal peaks occurring during the cardiac signal segment. In other examples, the amplitude metric may be mean, median, maximum or other representative value of the absolute amplitude of all signal samples during the cardiac signal segment.

Figure 14A:
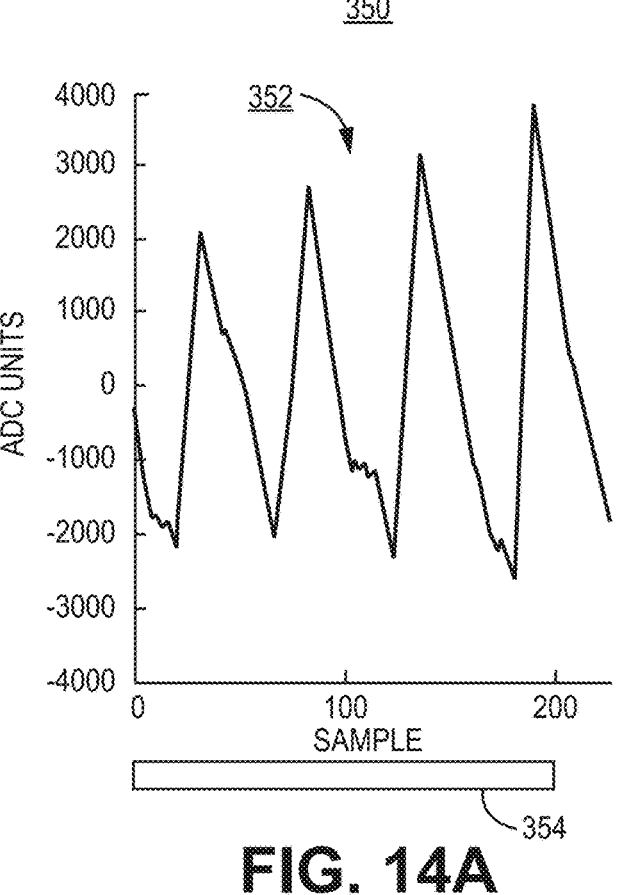
FIG. 14A is a diagram of a cardiac electrical signal that may be received from the sensing circuit of FIG. 4 during a pacing escape interval.

FIG. 14A is a diagram 350 of a cardiac electrical signal 352 that may be received from morphology signal channel 87 during a pacing escape interval and buffered in memory

Figure 14B:
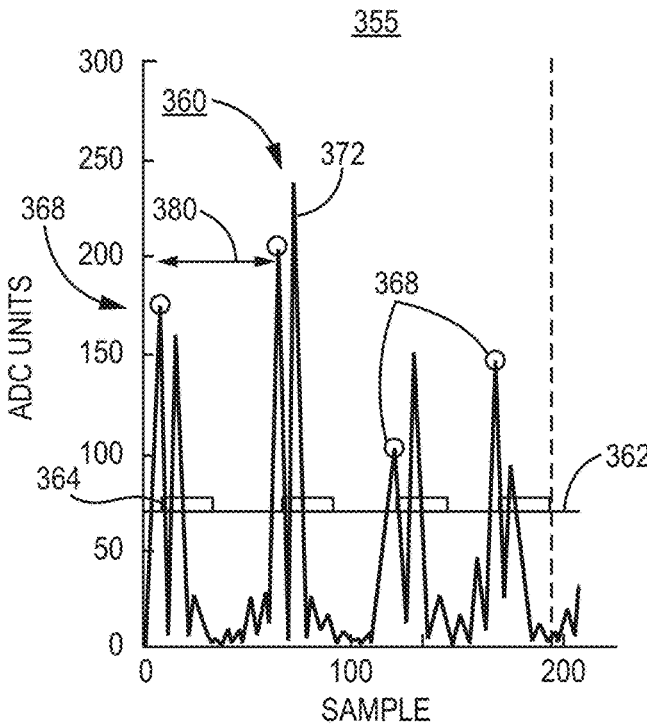
FIG. 14B is a diagram of a rectified first order difference signal determined from the cardiac electrical signal of FIG. 14A depicting a method for determining an amplitude metric and a rate metric from the cardiac signal segment according to some examples.

82 over a time segment 354 at block 306 of FIG. 13. FIG. 14B is a diagram 355 of a method for determining an amplitude metric at block 310 of FIG. 13 from the cardiac electrical signal of FIG. 14A. The cardiac electrical signal 352 shown in FIG. 14A may be a wide band and notch filtered signal received from morphology signal channel 87. In this example, the cardiac electrical signal 352 is sensed during a VT/VF rhythm. The time segment 354 is a 0.75 second time segment in the example shown but can be longer or shorter in other examples. Time segment 354 starts after an onset delay that is started when the pacing escape interval (not shown in FIG. 14A) is started and may end at a processing interval earlier than the pacing escape interval ending time (e.g., as described in conjunction with FIG. 6). Control circuit 80 may process the received signal 352 to determine a gradient signal that is bandpass filtered. Control circuit 80 may determine a first order difference signal from the bandpass filtered, gradient signal that is subsequently rectified to obtain the rectified difference signal 360 shown in FIG. 14B.

Control circuit 80 may establish a signal pulse amplitude threshold used for identifying signal pulses in the cardiac signal segment buffered over time segment 354. In the example shown, the signal pulse amplitude threshold 362 is set to one-third of the maximum peak amplitude 372 of the rectified, first order difference signal segment 360. As described below, the signal pulse amplitude threshold 362 can be used to identify signal pulses 368 having a maximum peak greater than the signal pulse amplitude threshold 362. In other examples, control circuit 80 may establish the signal pulse amplitude threshold by first dividing the cardiac signal segment into multiple subsegments, e.g., 0.125 to 1 second subsegments depending at least in part on the total duration of the cardiac signal segment. Control circuit 80 may determine local maximum amplitudes during each subsegment. If a local maximum amplitude is less than a percentage, e.g., less than 30%, less than 25%, or less than 20% of the overall maximum peak amplitude of the entire cardiac signal segment, control circuit 80 may set the local maximum amplitude to be equal to the overall maximum peak amplitude. Control circuit 80 may determine a signal pulse amplitude threshold used for identifying signal pulses as a predetermined percentage, e.g., 15 to 50% or about one-sixth to one-half, of the average of the local maximum amplitudes of the subsegments.

After establishing a signal pulse threshold 362, control circuit 80 may identify each signal pulse of the rectified, difference signal having an amplitude that is greater than the signal pulse amplitude threshold 362 and separated by a minimum signal interval 364 from a preceding identified signal pulse. The minimum signal interval 364 may be a predetermined number of sample points, e.g., 20 to 45 sample points or 25 sample points equal to about 97.6 ms at a sampling rate of 256 Hz as an example. The maximum peaks of signal pulses 368 (four signal pulses marked by circles in this example) having an amplitude greater than signal pulse amplitude threshold 362 and separated by a minimum signal interval 364 are identified as signal pulses by control circuit 80 and may correspond to ventricular event signals, e.g., R-waves or fibrillation waves. The identified signal pulses 368 may be used for determining an amplitude metric and an estimate of the ventricular rate from the cardiac signal segment buffered over time segment 354.

Control circuit 80 may determine the amplitude metric at block 310 of FIG. 13 as a representative amplitude of all of the identified signal pulses 368 shown in FIG. 14B. The representative amplitude can be determined as a mean amplitude of all of the identified signal pulse peaks 368 in some examples. Control circuit 80 may additionally or alternatively determine a peak amplitude metric by determining the maximum peak amplitude of all the identified signal pulses 368. The representative amplitude metric determined from each cardiac signal segment may be correlated to the likelihood of ventricular activity being present in the cardiac signal segment.

Referring again to FIG. 13, control circuit 80 may compare the amplitude metric determined at block 310 of FIG. 13 to low amplitude criteria at block 312. For example, the amplitude metric may be compared to a low amplitude threshold at block 312, which may be 0.050 to 0.3 millivolts (mV) or about 0.1 mV or 0.2 mV in various examples. When the amplitude metric is less than the low amplitude threshold, control circuit 80 may determine no VT/VF evidence at block 326. In response to determining no VT/VF evidence at block 326, therapy delivery circuit 84 may deliver the pending pacing pulse at block 328 upon determining that the current pacing escape interval (or pacing delay interval) has expired at block 327. When the amplitude metric(s) meet the low amplitude criteria at block 312, intrinsic ventricular event signals are likely to be absent such that VT/VF is unlikely to be present, indicating a need for cardiac pacing pulse delivery, e.g., as in asystole or a long ventricular pause.

It is to be understood that in some examples, one or more cardiac signal segments buffered during the pacing escape interval and/or any subsequent pacing delay intervals may be required to have an amplitude metric that is less than the low amplitude threshold at block 312 for determining no VT/VF evidence at block 326. If a requisite or threshold number (one or more) of the cardiac signal segments being analyzed have an amplitude metric greater than the low amplitude threshold, control circuit 80 may determine that low amplitude criteria are not met at block 312 and proceed to block 314 to continue the analysis for determining evidence of VT/VF.

At block 314, control circuit 80 may determine a rate metric by determining a peak interval 380 (see FIG. 14B) between each pair of consecutive signal pulses 368 identified in the cardiac signal segment at block 310. For the sake of clarity, only one peak interval 380 is labeled in FIG. 14B, between the first two consecutive signal pulses 368 identified during time segment 354. However, it is to be understood that the peak intervals from the first to the second signal pulse, from the second to the third signal pulse, and from the third to the fourth signal pulse (of the four identified signal pulses 368), may each be determined by control circuit 80.

Control circuit 80 may determine the rate metric at block 314 of FIG. 13 as the mean of all peak intervals 380 determined during the cardiac signal segment. Depending on the length of the cardiac signal segment and the ventricular rate, only a single peak may be identified in some cardiac signal segments. A single peak interval may be indeterminable from one cardiac signal segment. In this case, the ventricular rate may be determined to be less than a VT/VF rate such that VT/VF rate criteria are not met at block 316. Control circuit 80 may determine no VT/VF evidence at block 326 based on a single signal pulse being identified in the cardiac signal segment in some examples. The pending pacing pulse may be delivered by therapy delivery circuit at block 328. In other examples, control circuit 80 may proceed to block 318 to continue an analysis of the cardiac signal segment for determining evidence of VT/VF when the rate metric is indeterminable due to only a single signal pulse being determined during the cardiac signal segment.

When at least two signal pulses are identified at block 310, control circuit 80 may determine at least one peak interval at block 314. When more than two peak intervals can be determined (e.g., between at least three identified signal pulses), control circuit 80 may determine the peak interval metric as the mean, median, minimum, maximum, range or other representative value of the peak intervals. The peak interval metric may be compared to an interval threshold corresponding to a VT/VF rate for determining VT/VF evidence at block 316. When the peak interval metric is greater than or equal to a VT/VF interval threshold, e.g., 220 to 350 ms or 260 ms as an example, the cardiac signal segment may be determined as a non-VT/VF evidence segment at block 326. The VT/VF interval threshold applied at block 316 may correspond to the VT interval zone or the VF interval zone, which may be programmable by a user. The pending pacing pulse may be delivered at block 328 in response to no VT/VF evidence being determined at block 326 based on the rate metric not meeting VT/VF rate criteria at block 316.

When the rate metric, which may be a single peak interval determined between two identified signal pulses or a representative value of multiple peak intervals determined between multiple identified signal pulses, is less than a VT/VF interval threshold at block 316, control circuit 80 may determine that the rate metric meets a VT/VF evidence requirement relating to the ventricular rate. In the example of FIG. 14B, the peak intervals 380 determined between consecutively identified signal pulses 368 are approximately 200 ms, less than an example VT/VF interval threshold of 220 ms. As such, control circuit 80 may determine that the cardiac signal segment meets the VT/VF evidence rate criteria at block 316 of FIG. 13.

Additionally or alternatively, control circuit 80 may determine a count of the signal pulses 368 identified in the cardiac signal segment. The identified signal pulses 368 are at least a threshold time interval 364 apart and, based on the time duration of the cardiac signal segment, a count of the identified signal peaks 368 can be an indication of the average rate of signal pulses during the cardiac signal segment. For instance, four signal pulses 368 are identified in the cardiac signal segment that is 0.75 seconds long, indicating an average rate interval of less than the example VT/VF interval threshold of 220 ms. A threshold number of more than 3 signal pulses in a 0.75 second segment may meet VT/VF rate criteria in an illustrative example. A metric of the peak intervals 380 and/or the count of identified signal pulses 368 may be compared to VT/VF rate criteria at block 316 of FIG. 13.

Referring again to FIG. 13, when the VT/VF rate criteria are met, control circuit 80 may optionally determine one or more noise metrics from the cardiac signal segment at block 318. Noise metrics may be identified to discriminate between a noisy signal segment and a cardiac signal segment that includes VT/VF evidence. The noise metrics determined at block 318 may include a mean rectified amplitude (MRA), a normalized mean rectified amplitude (NMRA), a muscle noise pulse count (MNPC) and/or a mean period. Depending on the overall duration of the cardiac signal segment, the noise metrics may be determined by first dividing the cardiac signal segment into multiple subsegments in some examples. For example, a 3-second cardiac signal segment of 768 samples (256 Hz sampling rate) may be divided into four subsegments of 192 samples. Each noise metric may be determined for each subsegment then the metric for the overall cardiac signal segment may be determined by averaging the noise metrics determined for each subsegment. In other examples, the noise metrics may be determined for the entire cardiac signal segment without first dividing the segment into subsegments. A 0.5 second cardiac signal segment may be divided into four 0.125 second subsegments or analyzed as a whole in various examples. As described above, control circuit 80 may determine the noise metrics from a rectified, difference signal determined from the cardiac signal segment received from morphology signal channel 87. In some examples, the first order difference signal is determined after determining a gradient signal and/or bandpass filtering of the cardiac signal segment, e.g., using a passband of 2 to 40 Hz or 3 to 32 Hz.

At block 318, control circuit 80 may determine a mean rectified amplitude (MRA) of the cardiac signal segment by summing all sample points in the rectified difference signal determined from the cardiac signal segment (or subsegment) and dividing by the total number of sample points. The MRA may be used for determining the NMRA by control circuit 80 by determining the absolute maximum peak amplitude during the cardiac signal segment (or subsegment) and dividing the MRA by the absolute maximum peak amplitude. Other example methods for determining a NMRA are generally disclosed in the above-incorporated U.S. Pat. No. 8,301,233.

At block 318, control circuit 80 may additionally or alternatively determine a MNPC. Control circuit 80 may determine the MNPC by from the bandpass filtered, first order difference signal from the buffered cardiac signal segment. Zero crossings of the non-rectified difference signal may be set by identifying consecutive positive and negative sample points and setting the amplitude of either the positive or negative sample point having the lowest absolute amplitude to zero to demarcate the zero crossings in the non-rectified signal segment. The difference signal with zero crossings set may then be rectified to facilitate identification of muscle noise pulses. Control circuit 80 may determine a noise pulse amplitude threshold by determining the maximum amplitude of the rectified difference signal over the entire cardiac signal segment (or a subsegment if determining MNPCs for multiple subsegments first) and setting the noise pulse amplitude threshold to a portion or percentage of the maximum amplitude. For instance, the noise pulse amplitude threshold may be set to be one-eighth of the maximum amplitude of the rectified difference signal. The noise pulse amplitude threshold used for determining a MNPC and the signal pulse amplitude threshold used for identifying signal pulses for determining an amplitude metric at block 310 and rate metric at block 314 may be determined separately to separately identify likely noise signals, such as skeletal muscle myopotential noise, and likely ventricular event signals, respectively.

Each signal pulse in the cardiac signal segment having an amplitude equal to or greater than the noise pulse amplitude threshold and having a pulse width (the time interval or number of sample points between zero-crossings) that is less than or equal to a noise pulse width threshold (e.g., a maximum of 6 sample points between zero-crossings) may be counted as a muscle noise pulse at block 318. All muscle noise pulses meeting the noise pulse amplitude threshold and the noise pulse width threshold requirements may be counted for determining a total MNPC. Other example techniques for determining a MNPC are generally disclosed in U.S. Pat. No. 10,561,332 (Zhang, et al.), incorporated herein by reference in its entirety. As indicated above, control circuit 80 may determine the MNPC for the entire cardiac signal segment or determine the MNPC for multiple subsegments and then determine the MNPC for the entire segment as the average (or sum) of the subsegment MNPCs.

In some examples, the MNPC is determined for each one of multiple cardiac signal segments (or subsegments) during a pacing escape interval and/or one or more pacing delay intervals by counting the number of identified muscle noise pulses and determining the maximum MNPC out of multiple cardiac signal segments (or subsegments) as a noise metric at block 318. Additionally or alternatively, control circuit 80 may identify each cardiac signal segment (or subsegment) having a MNPC that is at least a threshold value, e.g., a MNPC of at least 4 to 10, depending on the overall duration of the cardiac signal segment (or subsegment). Control circuit 80 may determine a noise metric at block 318 as a count of the cardiac signal segments (or subsegments) that have a MNPC that is at least the threshold value. Other example methods for determining noise metrics by identifying skeletal muscle noise pulses are generally disclosed in U.S. Pat. No. 7,761,142 (Ghanem, et al.), incorporated herein by reference in its entirety.

At block 318, control circuit 80 may additionally or alternatively determine the mean period of the cardiac signal segment. As described above, control circuit 80 may determine the mean period as the inverse of the mean frequency of the cardiac signal segment, which is an estimate of the center frequency of the cardiac signal segment. The mean period may be estimated as the ratio of the sum of all sample point amplitudes of the rectified cardiac signal segment to the sum of all sample point amplitudes of the rectified first order difference signal.

At block 320, control circuit 80 may determine whether noise criteria are met in some examples. When noise criteria are met, the cardiac signal segment may be noise contaminated but is unlikely to include VT/VF and may be determined as non-VT/VF evidence at block 326. The noise criteria include one or more thresholds or other conditions that are applied to the noise metrics determined at block 318 for one or more cardiac signal segments for identifying the presence of noise during the pacing escape interval and/or one or more pacing delay intervals. The noise criteria applied at block 320 may discriminate between a signal segment that includes skeletal muscle myopotentials and/or electromagnetic interference (EMI) or other noise signals and a cardiac signal segment that likely includes R-waves or fibrillation waves occurring in a VT/VF rhythm.

In some examples control circuit 80 compares the NMRA to a threshold value at block 320. When the NMRA is less than or equal to the threshold, the deviation of the cardiac signal from baseline is relatively low, which may indicate a noisy segment because the cardiac signal is frequently near or crossing the baseline. A relatively high degree of deviation from the baseline, as indicated by a relatively high NMRA, may be evidence of VT/VF because fewer, relatively larger signals may be present in the cardiac signal segment. The NMRA threshold may be between 40 and 50 in some examples. If the NMRA is less than or equal to the corresponding threshold at block 320, control circuit 80 may determine noise criteria are met and advance to block 326 to determine no VT/VF evidence in the cardiac signal segment(s). Therapy delivery circuit 84 may deliver the pending pacing pulse at block 328 when the current pacing escape interval (or pacing delay interval) expires at block 327. If the NMRA is greater than the threshold, control circuit 80 may advance to block 322 to evaluate VT/VF morphology metrics for determining evidence of VT/VF.

Additionally or alternatively, at block 320 control circuit 80 may compare the highest MNPC determined from the cardiac signal segments or subsegments to a threshold value. Control circuit 80 may determine that noise criteria are met when the highest MNPC is greater than a threshold value and determine no VT/VF evidence at block 326. The threshold value compared to the highest MNPC may be between 2 and 12 in some examples and may depend on the duration of the cardiac signal segment(s) or subsegments. In one illustrative example, for a 0.5 second cardiac signal segment, the noise criteria applied at block 320 may include requiring the NMRA to be less than or equal to a threshold of 40 to 50, e.g., 47, and the highest MNPC be equal to or greater than a threshold of 2 to 10, e.g., 3. Control circuit 80 may determine that noise criteria are met at block 320 and determine no VT/VF evidence at block 326 in response to these conditions being met.

Additionally or alternatively, control circuit 80 may compare a count of cardiac signal segments (or subsegments) that have a MNPC greater than a threshold number of pulses, e.g., 2 to 8 pulses, to a noise threshold value at block 320. Either a single segment (or subsegment) having a high MNPC or a threshold number of segments (or subsegments) having a moderately high MNPC can be an indication of a noisy cardiac signal, but not evidence of VT/VF. For example, when at least 2, 3, 4 or other selected number of cardiac signal segments (or subsegments) are determined to have a MNPC of at least 2 to 6 (or any other selected threshold MNPC), control circuit 80 may determine that noise criteria are met at block 320. In some examples, when the count of segments (or subsegments) having a MNPC greater than a threshold number is at least 3 and the NMRA for those segments (or subsegments) is less than or equal to a corresponding threshold, e.g., 47, control circuit 80 may determine that noise criteria are met at block 320.

Figure 14C:
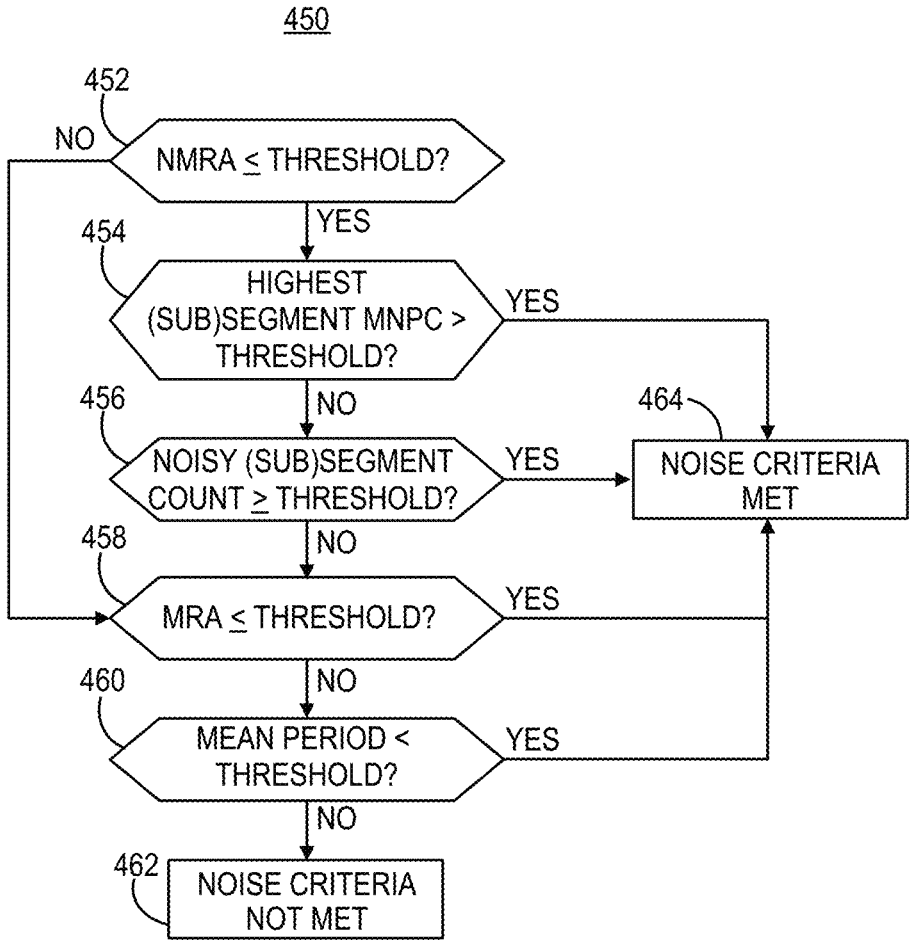
FIG. 14C is a flow chart of a method for determining when noise criteria are met at block 320 of FIG. 13 according to some examples.

FIG. 14C is a flow chart 450 of a method for determining when noise criteria are met at block 320 of FIG. 13 according to some examples. For instance, control circuit 80 may apply a first set of noise criteria to the NMRA and the MNPC(s) (blocks 452, 454 and 456) according to any of the examples given above to determine if noise criteria are met at block 320. If this first set of criteria is unmet, alternative criteria may be applied to other noise metrics (e.g., at blocks 458 and 460) determined for the cardiac signal segment(s). The first set of criteria may require that the NMRA is less than or equal to a threshold (block 452) and either the highest segment (or subsegment) MNPC is greater than a threshold pulse count (block 454) or the count of noisy cardiac signal segments (or subsegments), each having at least a threshold number of muscle noise pulses, is greater than or equal to a threshold number (block 456).

Control circuit 80 may additionally or alternatively determine that noise criteria are met at block 320 of FIG. 13 when the MRA is determined to be less than a threshold (block 458 of FIG. 14C). If the NMRA does not meet the threshold applied at block 452, or the MNPC(s) do not meet the criteria applied at blocks 454 or 456, control circuit 80 may compare the MRA to an MRA threshold value at block 458. When the MRA is low, the relatively low amplitude cardiac signal segment is unlikely to include true R-waves or fibrillation waves and may be determined to meet noise criteria at block 464 (and at block 320 of FIG. 13). No VT/VF evidence may be determined at block 326 in FIG. 13. The MRA threshold may be between 30 and 40, as examples, and can be 33 in an example.

Control circuit 80 may additionally or alternatively determine that noise criteria are met at block 320 of FIG. 13 when the mean period is less than a respective threshold. When the mean period is less than 50, 60, 70, 80, 85, 90 or other selected threshold at block 460 of FIG. 14C, control circuit 80 may determine that the noise criteria are met (block 464) by the cardiac signal segment and determine no VT/VF evidence at block 326 of FIG. 13. A relatively high mean period may indicate relatively low frequency R-waves or fibrillation waves are present in the cardiac signal segment as opposed to relatively higher frequency noise pulses. As such, if the mean period is greater than the threshold at block 320, control circuit 80 may advance to block 322 to determine VT/VF morphology metrics for determining VT/VF evidence.

When the noise metrics determined for the cardiac signal segment(s) meet the noise criteria applied at block 320, which may be criteria applied to one or more of the MRA, NMRA, highest MNPC, count of signal segments or subsegments having at least a minimum MNPC, and/or mean period, singly or in one or more combinations as shown in FIG. 14C, control circuit 80 can determine that the cardiac signal segment is not evidence of VT/VF at block 326. Other methods may be used for determining noise metrics and determining that a cardiac signal segment is contaminated by non-cardiac noise signals at block 320 than the specific examples given herein. Therapy delivery circuit 84 may deliver the pending pacing pulse at block 328 upon expiration of the current pacing escape interval (or pacing delay interval) at block 327 when no VT/VF evidence is determined based on noise criteria being met at block 320.

In other examples, when noise criteria are met at block 320, control circuit 80 may withhold pacing pulse delivery for one or more delay intervals or a predetermined time interval. Control circuit 80 may withhold pacing pulse delivery until a maximum delay interval is reached or until the noise subsides and noise criteria are not met before delivering a pacing pulse. When pacing is delayed or withheld due to noise, control circuit 80 may continue to buffer and analyze cardiac signal segments according to the process of flow chart 300.

When the noise metrics determined for the cardiac signal segment(s) do not meet the noise criteria applied at block 320, control circuit 80 may advance to block 322. For example, as shown in FIG. 14C, when the NMRA, MNPC(s), MRA, and/or mean period do not meet the respective thresholds applied at blocks 452, 454, 456, 458 and/or 460, control circuit 80 may determine that noise criteria are not met at block 462. It is to be understood that determination of noise metrics and evaluation whether noise criteria are met at blocks 318 and 320 of FIG. 13 are optional. In some examples, blocks 318 and 320 may be omitted in the process executed by control circuit 80 for determining VT/VF evidence. Control circuit 80 may advance from block 316 to block 322 without determining and evaluating noise metrics.

At block 322, control circuit 80 may determine any of the example VT/VF morphology metrics from the cardiac signal segment(s) described above, e.g., the LSC, SW and/or mean period. Control circuit 80 compares the VT/VF morphology metrics to the VT/VF evidence criteria at block 324. The VT/VF evidence criteria may include a threshold applied to each respective VT/VF morphology metric determined at block 322, or according to any of the VT/VF evidence criteria described above, that promotes determination of VT/VF evidence with a high degree of specificity for avoiding delivering cardiac pacing during VT/VF. When the VT/VF evidence criteria are met at block 324, the pending pacing pulse may be delayed by control circuit 80 at block 330 if a maximum pacing delay has not been reached at block 325.

If the maximum pacing delay has been reached, as determined at block 325, therapy delivery circuit 84 may deliver the pending pacing pulse at block 328 if VT/VF has not been detected by arrhythmia detection circuit 92 during the maximum pacing delay and a Vsense signal deemed to be a valid event signal has not been received during the maximum pacing delay. If the VT/VF evidence criteria are not met at block 324 for the cardiac signal segment(s) sensed during the pacing escape interval and/or one or more pacing delay intervals, control circuit 80 determines no VT/VF evidence at block 326. Therapy delivery circuit 84 delivers the pending pacing pulse at block 328 upon expiration of the current pacing escape interval (or pacing delay interval) as determined at block 327. When the pending pacing pulse is delivered, control circuit 80 may start a new pacing escape interval and may advance to the flow chart of FIG. 16 as indicated by connector "A." As described below, a different process for determining VT/VF evidence during post-pace pacing escape intervals may be performed than the process performed by control circuit 80 during post-sense pacing escape intervals for controlling pacing pulse delivery.

Figure 15:
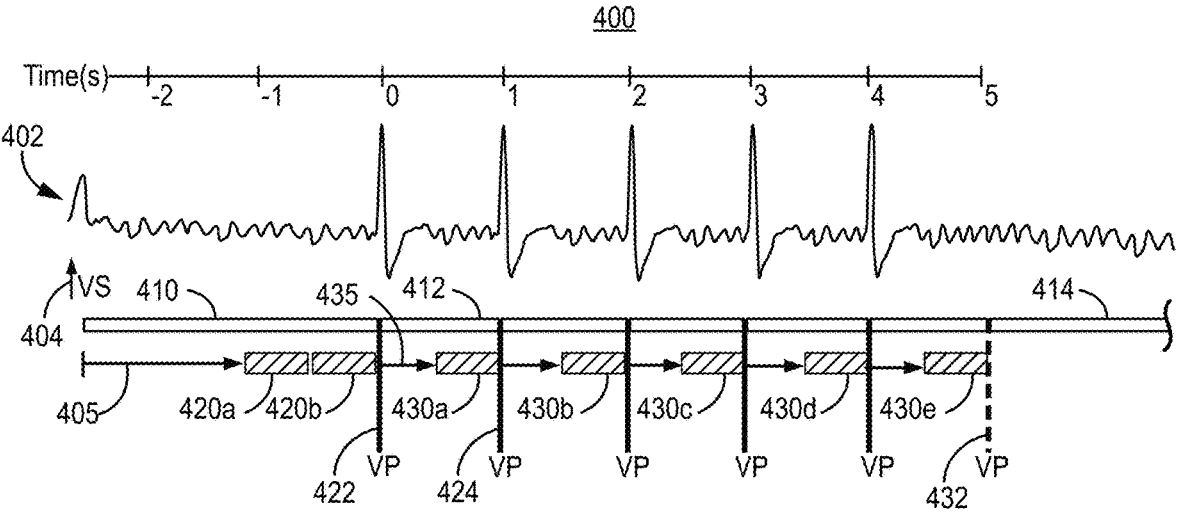
FIG. 15 is a diagram of a method for determining evidence of VT/VF during cardiac signal segments sensed between delivered cardiac pacing pulses according to some examples.

FIG. 15 is a diagram 400 of a method for determining evidence of VT/VF during cardiac signal segments sensed between delivered cardiac pacing pulses according to some examples. A cardiac electrical signal 402 sensed by sensing circuit 86 is passed to control circuit 80 for buffering cardiac signal segments during pacing escape intervals 410 and 412. Control circuit 80 starts a hysteresis pacing escape interval 410 in response to receiving a Vsense signal 404 from sensing circuit 86. The Vsense signal 404 may correspond to a single Vsense signal received from one of sensing channels 83 or 85 when a single sensing channel is selected for sensing R-waves. In other examples, Vsense signal 404 may represent a Vsense signal determined to be a valid event signal when a Vsense signal is received from both sensing channel 83 and 85 within a validation window and/or a cardiac electrical signal sensed during the validation window meets R-wave morphology criteria. The hysteresis pacing escape interval may be 1.5 to 6 seconds long in various examples and is shown as being about 2.5 seconds in FIG. 15.

As described above, control circuit 80 may wait for an onset delay interval 405 after starting the pacing escape interval 410. If another Vsense signal determined to be a valid event signal is not received during pacing escape interval 410, control circuit 80 may buffer a cardiac signal segment during one or more time segments 420a and 420b, collectively time segments 420, extending up to a processing time interval (not illustrated in FIG. 15) for analysis prior to the expiration of hysteresis pacing escape interval 410. When no evidence of VT/VF is determined by control circuit 80 based on the analysis of cardiac signal segments 420 according to any of the examples given above (e.g., in conjunction with FIG. 5, 9 or 13), therapy delivery circuit 84 delivers the pending cardiac pacing pulse 422 upon expiration of the hysteresis pacing escape interval 410.

In response to the delivered pacing pulse 422, control circuit 80 may start a lower rate pacing escape interval 412. The lower rate pacing escape interval 412 is 1 second in this example but may be set to correspond to a programmed lower rate of 30 to 70 ppm in various examples. Control circuit 80 may wait for a post-pace onset delay interval 435 and buffer a cardiac signal segment sensed over time segment 430a for determining evidence of VT/VF during the lower rate pacing escape interval 412.

One relatively short cardiac signal segment corresponding to time segment 430a may be insufficient for determining VT/VF evidence, however. As such, control circuit 80 may determine VT/VF morphology metrics, and in some examples an amplitude metric, rate metric, and/or noise metric(s) as generally described above in conjunction with FIG. 13, from the cardiac signal segment sensed over time segment 430a and buffer the determined data in memory 82. In some examples, control circuit 80 may determine if the cardiac signal segment is a VT/VF evidence segment or a non-VT/VF evidence segment based on the determined metrics and flag the cardiac signal segment in memory 82 accordingly.

Control circuit 80, however, may not decide to delay the pending pacing pulse 424 based on one cardiac signal segment corresponding to time segment 430a. The pending pacing pulse 424 may be delivered by therapy delivery circuit 84 upon expiration of the pacing escape interval 412 even when the cardiac signal segment sensed during the lower rate pacing escape interval 412 (during time segment 430a) is determined to be a VT/VF evidence segment. Control circuit 80 may be configured to accumulate VT/VF evidence data from multiple post-pace cardiac signal segments sensed during successive lower rate pacing escape intervals 412, each started in response to a delivered pacing pulse (VP). Control circuit 80 may determine that VT/VF evidence criteria is met for delaying or withholding cardiac pacing that has already started when a threshold number of the post-pace cardiac signal segments (corresponding to time segments 430a-430e, collectively 430) are determined to be VT/VF evidence segments.

VT/VF evidence criteria for delaying a pending cardiac pacing pulse after pacing has already begun at a given pacing rate (which may be a fixed or variable pacing rate) may include requiring at least a minimum number of cardiac signal segments, e.g., 2, 3 4, 5, 6, 7, or 8 cardiac signal segments, sensed during post-pace pacing escape intervals be analyzed for determining VT/VF evidence before delaying a cardiac pacing pulse. For example at least 3, 4, 5, 6, 8 or other selected number of pacing pulses may be delivered before making a decision to delay a pacing pulse based on analysis of the cardiac signal sensed during the associated pacing escape intervals. Control circuit 80 may determine VT/VF evidence criteria are met when a predetermined percentage or ratio, e.g., at least half, at least two-thirds, at least three-fourths, 100% or other selected percentage or portion of a minimum number of cardiac signal segments sensed during post-pace pacing escape intervals are identified as VT/VF evidence segments. In some examples, the most recent one, two, or three cardiac signal segments may be required to be identified as VT/VF evidence segments in order for the VT/VF evidence criteria to be met to delay or withhold a pending pacing pulse that is scheduled to consecutively follow a preceding pacing pulse.

In the example shown, at least 5 cardiac signal segments sensed during post-pace pacing escape intervals 412 (during time segments 430) are required to be analyzed in order to stop or delay pacing being delivered, e.g., at the programmed lower rate. In an illustrative example, when at least 3 out of 5 cardiac signal segments corresponding to time segments 430 and at least the latest cardiac signal segment corresponding to time segment 430e are identified as VT/VF evidence segments, control circuit 80 may delay pending pacing pulse 432 (shown by dashed line to indicated that it is not delivered). Control circuit 80 may start a pacing delay interval 414 to delay the pending pacing pulse 432 that would normally be delivered at the expiration of the lower rate pacing escape interval 412. The pacing delay interval 414 may be set to the lower rate pacing escape interval, to a hysteresis pacing escape interval, or set to a pacing delay interval, e.g., up to 9 seconds, to enable control circuit 80 to detect VT/VF according to tachyarrhythmia detection algorithms being executed by arrhythmia detection circuit 92 without interference of pacing artifact in the cardiac electrical signals sensed by sensing circuit 86 during the pacing delay interval 414.

If VT/VF is detected by control circuit 80 (e.g., by arrhythmia detection circuity 92) during the pacing delay interval 414, the pending pacing pulse may be cancelled and therapy delivery circuit 84 may can deliver a tachyarrhythmia therapy, e.g., ATP therapy and/or CV/DF shock. If VT/VF is not detected and a Vsense signal determined to be a valid event signal is not received during the pacing delay interval 414, therapy delivery circuit 84 can deliver the pending pacing pulse upon expiration of the pacing delay interval 414. In some examples, control circuit 80 may continue analyzing cardiac signal segments sensed during the pacing delay interval 414, e.g., according to any of the examples described above in conjunction with FIGS. 5-13. A cardiac signal segment may be buffered from cardiac electrical signal 402 during pacing delay interval 414, e.g., during a time segment that starts after an onset delay interval.

In some examples, if VT/VF evidence criteria is not met during the pacing delay interval 414, e.g., based on a minimum number of cardiac signal segments being analyzed, the pacing delay interval 414 could be truncated early by control circuit 80. The pending pacing pulse 432 could be delivered by therapy delivery circuit 84 upon determining no VT/VF evidence based on the minimum number of cardiac signal segments, prior to expiration of pacing delay interval 414. To illustrate, if pacing delay interval 414 is set to eight seconds to allow time for control circuit 80 to detect VT/VF based on VT/VF detection algorithms being executed by arrhythmia detection circuit 92, and if six to eight consecutive cardiac signal segments spanning at least three to four seconds during the pacing delay interval 414 are determined to be non-VT/VF evidence segments, the pacing delay interval 414 may be truncated early. The pending pacing pulse 432 may be delivered upon determining no VT/VF evidence based on the analysis of at least four seconds (or other specified time interval) of accumulated cardiac signal segment data determined during the pacing delay interval 414.

FIG. 16 is a flow chart 500 of a method for controlling the delivery of cardiac pacing pulses scheduled at pacing escape intervals started in response to delivered pacing pulses according to some examples. Control circuit 80 may enter the process of flow chart 500 at block 502 upon delivering the first pacing pulse of a series of pacing pulses. In some instances, control circuit 80 enters the process of flow chart 500 after the first pacing pulse is delivered following expiration of a post-sense pacing escape interval (and in some cases one or more pacing delay intervals), e.g., at block 328 of FIG. 13, as indicated by connector "A." The post-sense pacing escape interval may be a hysteresis interval, which may be extended up to a maximum pacing delay. In response to the first pacing pulse being delivered following the expiration of a post-sense pacing escape interval, control circuit 80 may schedule the next pacing pulse at block 502 by starting a post-pace pacing escape interval, which may be a lower rate pacing escape interval as described in conjunction with FIG. 15.

In other examples, however, the process of flow chart 500 may begin at block 501 when a pacing pulse is delivered by therapy delivery circuit 84 without starting a pacing escape interval in response to a Vsense signal. For instance, control circuit 80 may be configured to detect asystole based on analysis of one or more cardiac signal segments when Vsense signals are not being received from sensing circuit 86. Techniques for detecting asystole are generally disclosed in the above-incorporated U.S. Patent Application No. 63/278,955 and corresponding U.S. patent application Ser. No. 18/045,135. Upon detection of asystole by control circuit 80, therapy delivery circuit 84 may deliver a pacing pulse (at block 501). Control circuit 80 may schedule the next pacing pulse at block 502 at a pacing escape interval, e.g., corresponding to the programmed hysteresis interval or corresponding to a programmed lower rate.

In other instances, a pacing pulse may be delivered at block 501 by therapy delivery circuit 84 as a post-shock pacing pulse. A post-shock pacing pulse may be delivered when a Vsense signal (deemed to be a valid event signal) is not received by control circuit 80 from sensing circuit 86 within a specified time interval following a CV/DF shock delivered by therapy delivery circuit 84. In response to delivering a post-shock pacing pulse, control circuit 80 may schedule a next pacing pulse at block 502, e.g., at a hysteresis interval or at a lower rate pacing escape interval.

At block 504, control circuit 80 may wait an onset delay interval before buffering a cardiac signal segment in memory 82 at block 506. In other examples, the morphology signal from morphology signal channel 87 may be buffered in memory 82 on an ongoing basis, but the cardiac signal segment analyzed for VT/VF evidence determination may not begin until the end of the onset delay interval. The onset delay interval may be selected to extend at least through a post-pace blanking period to avoid analysis of a pacing artifact in the sensed cardiac electrical signal. The onset delay interval may be longer than the post-pace blanking period. The post-pace onset delay interval may be 0.20 to 1 second, as examples, and may depend on the overall duration of the post-pace pacing escape interval. The post-pace onset delay interval is at least 0.3 seconds in some examples.

The cardiac electrical signal may be buffered in memory 82 at block 506 over a time segment starting from the end of the post-pace onset delay interval until a processing time interval before the expiration time of the post-pace pacing escape interval. The duration of the time segment over which the cardiac signal segment is buffered may be determined by control circuit 80 as a percentage, e.g., 50 to 100%, of the pacing escape interval less the processing time interval less a post-pace blanking period in some examples. The onset delay interval may be set as the difference between the post-pace pacing escape interval and the determined duration of the cardiac signal segment.

It is to be understood that at any time during the pacing escape interval, if a Vsense signal is received by control circuit 80 from the sensing circuit 86 as indicated at block 508 (which may be determined to be a valid event signal as described above in conjunction with FIG. 5), control circuit 80 may inhibit the pending pacing pulse and start a post-sense pacing escape interval. Control circuit 80 may return to the process of flow chart 300 of FIG. 13 as indicated by connector "B." Control circuit 80 may enter the process of flow chart 300 of FIG. 13 at block 302 when the Vsense signal is received (and deemed valid), and a pending pacing pulse is scheduled at a post-sense pacing escape interval at block 304 of FIG. 13.

Referring again to FIG. 16, after buffering the cardiac signal segment at block 506, if no valid Vsense signals have been received ("no" branch of block 508), control circuit 80 may determine if a minimum number of cardiac signal segments have been buffered at block 510. The minimum number of cardiac signal segments may correspond to a minimum cumulative time duration of the buffered cardiac signal segments that is required for determining VT/VF evidence with a high enough confidence to warrant interrupting pacing at the current pacing rate. The minimum number of segments may depend on the duration of each segment and may be between 3 and 10 segments when the cardiac signal segment is 0.5 seconds in duration, as illustrative examples.

If the minimum number of buffered signal segments has not been reached at block 510, therapy delivery circuit 84 delivers the pending pacing pulse at block 501 without delay upon expiration of the current post-pace pacing escape interval. The next pacing pulse is scheduled at block 502, e.g., by restarting the lower rate (or other) pacing escape interval. When the minimum number of buffered signal segments sensed during post-pace pacing escape intervals has been reached ("yes" branch of block 510), control circuit 80 may determine VT/VF metrics from all of the buffered signal segments at block 512.

When pacing has started (e.g., at block 501), the time duration of the post-pace, pacing escape interval started at block 502 may not be long enough to buffer a cardiac signal segment that contains enough signal information for reliably discriminating between VT/VF evidence and no VT/VF evidence. Accordingly, control circuit 80 may control therapy delivery circuit 84 to deliver multiple cardiac pacing pulses at the lower rate (and/or hysteresis) pacing intervals to accumulate multiple, relatively shorter cardiac signal segments for analysis for VT/VF evidence determination before deciding to delay a pending pacing pulse.

In some examples, control circuit 80 may determine the VT/VF morphology metrics from each individual signal segment, buffered during each post-pace pacing escape interval, to identify each segment as either a VT/VF evidence segment or a non-VT/VF evidence segment. As described above, the VT/VF morphology metrics determined at block 512 may include LSC, SW and/or mean period as examples. In some examples, control circuit 80 may identify signal pulses, e.g., using the techniques generally described in conjunction with FIG. 13 and FIGS. 14A and 14B, for determining an amplitude metric and/or a rate metric used for identifying an individual cardiac signal segment as a VT/VF evidence segment or non-VT/VF evidence segment. Identification of an individual cardiac signal segment as a VT/VF evidence segment or a non-VT/VF evidence segment based on the amplitude metric and/or rate metric determined from identified signal pulses may be performed without determining other VT/VF morphology metrics, such as LSC, SW and/or mean period. However, as described above, the VT/VF morphology metrics may be determined when the amplitude metric and/or rate metric do not result in identifying the cardiac signal segment as a non-VT/VF segment. In some examples, one or more noise metrics may be determined for identifying an individual cardiac signal segment as a non-VT/VF segment when noise criteria are met, as generally described in conjunction with FIG. 13 and FIG. 14C.

Each of the minimum number of cardiac signal segments may be analyzed and flagged as either a VT/VF evidence segment or a non-VT/VF evidence segment in a buffer in memory 82. A count of the VT/VF evidence segments may be maintained in memory 82, e.g., as an X of Y count, for determining whether to delay a pending pacing pulse after the minimum number of cardiac signal segments have been acquired during post-pace pacing escape intervals and subsequently analyzed.

In some examples, control circuit 80 may wait until all of the minimum number of cardiac signal segments have been buffered in memory 82 to start processing and analysis of the signal segments. In this way, control circuit 80 may avoid unnecessary processing and analysis of the cardiac signal segments, and thereby conserve power source 98, if a Vsense signal (determined to be a valid event signal) is received from sensing circuit 86 before all of the minimum number of cardiac signal segments have been buffered. In this case, a processing time interval may be optional after each cardiac signal segment before expiration of the respective pacing escape interval. A processing time interval may instead be provided after all of the minimum number of cardiac signal segments have been acquired so that analysis of all of the buffered cardiac signal segments may occur during one processing time interval, after the minimum number of segments have been buffered.

In still other examples, control circuit 80 may append the buffered cardiac signal segments together to obtain an n-second segment from which VT/VF morphology metrics may be determined. VT/VF morphology metrics, an amplitude metric and/or noise metrics may be determined from the appended cardiac signal segments in some examples for use in determining VT/VF evidence in the cardiac signal, e.g., using the techniques generally described above in conjunction with FIG. 13. However, determination of a rate metric based on intervals between identified signal pulse peaks may be irrelevant since the appended signal segments are discontinuous segments.

At block 514, control circuit 80 determines if post-pace VT/VF evidence criteria are met. The post-pace VT/VF evidence criteria may be the same or different than the post-sense VT/VF evidence criteria, e.g., as applied at block 324 of FIG. 13. To illustrate, control circuit 80 may set a post-sense hysteresis pacing interval to four seconds and acquire six 0.5-second cardiac signal segments during the post-sense hysteresis pacing interval. When at least 4 out of 6 of the cardiac signal segments, including the most recent of the cardiac signal segments, are identified as VT/VF evidence segments, e.g., based on the LSC, SW and/or mean period meeting respective thresholds or other VT/VF evidence criteria according to any of the examples given herein, control circuit 80 may determine that the post-sense VT/VF evidence criteria are met and start a pacing delay interval. At block 514 of FIG. 16, control circuit 80 may determine, in an analogous manner, that the post-pace VT/VF evidence criteria are met when at least 4 out of 6 post-pace cardiac signal segments are VT/VF evidence segments, including the most recent cardiac signal segment. In other examples, however, different post-pace VT/VF evidence criteria may be applied to the metrics determined from the cardiac signal segments sensed during post-pace pacing escape intervals than the VT/VF evidence criteria applied to one or more cardiac signal segments sensed during a post-sense pacing escape interval, which may be a hysteresis interval, and/or one or more pacing delay intervals. Furthermore, different VT/VF morphology metrics, amplitude metrics, rate metrics, and/or noise metrics may be determined from post-pace cardiac signal segments than the VT/VF morphology metrics, amplitude metrics, rate metrics, and/or noise metrics determined from post-sense cardiac signal segments.

In response to determining that the post-pace VT/VF evidence criteria are not met at block 514, the pending pacing pulse may be delivered at block 501 upon expiration of the pacing escape interval as determined at block 516. The process of flow chart 500 may be repeated. When the minimum number of cardiac signal segments has already been reached, control circuit 80 may evaluate the accumulated cardiac signal segments for determining if the post-pace VT/VF evidence criteria are met at block 514. Cardiac signal segments and/or VT/VF evidence data determined from the cardiac signal segments may be buffered in memory 82 in a first in first out manner so that a determination of whether the post-pace VT/VF evidence criteria are met may be made after each subsequent pacing pulse, without waiting for a new minimum number of cardiac signal segments to be acquired. In other examples, a predetermined number of pacing pulses may be delivered after each determination of VT/VF evidence criteria not being met at block 514 to enable control circuit 80 to buffer the next minimum number of cardiac signal segments sensed during the same number of post-pace pacing escape intervals.

In response to determining that the post-pace VT/VF evidence criteria are met at block 514, control circuit 80 may delay the pending pacing pulse at block 520, if a maximum pacing delay has not been reached, as determined at block 518. In some examples, when the maximum pacing delay has been reached, and VT/VF has not been detected or a valid Vsense signal has not been received, control circuit 80 may return to block 501 to deliver the pending pacing pulse.

If the maximum pacing delay has not been reached ("no" branch of block 524), control circuit 80 may delay the pending pacing pulse at block 520 by restarting a lower rate pacing escape interval in some examples. If control circuit 80 has not detected VT/VF (at block 522), control circuit 80 may return to block 506 to buffer the next cardiac signal segment during the restarted pacing escape interval. In other examples, control circuit 80 may delay the pending pacing pulse at block 520 by starting a hysteresis interval or any another pace delay interval. The pace delay interval may be longer than the lower rate pacing escape interval. In this case, control circuit 80 may return to block 506, as long as a VT/VF detection has not been made by arrhythmia detection circuit 92, and buffer one or more cardiac signal segments in memory 82 during the pace delay interval. By applying a relatively longer pace delay interval at block 520 than the lower rate interval, arrhythmia detection circuit 92 can have more time for detecting VT/VF without interference of pacing artifact in the cardiac electrical signals.

If arrhythmia detection circuit 92 detects VT/VF at block 522 after control circuit 80 delays a pending cardiac pacing pulse (or at any time during delivery of the pacing pulses), control circuit 80 may cancel the pending pacing pulse (at block 524) and deliver a tachyarrhythmia therapy (e.g., ATP therapy and/or CV/DF shock) at block 526. After the VT/VF therapy, when the tachyarrhythmia is successfully terminated, therapy delivery circuit 84 may deliver a post-shock pacing pulse in some cases such that control circuit 80 re-enters the process of flow chart 500 at block 501. In other instances, control circuit 80 may receive a Vsense signal from sensing circuit 86 that is determined to be a valid event signal following termination of the VT/VF and may enter the process of flow chart 300 of FIG. 13 at block 302, for example.

The disclosure further provides the following examples:

Example 1. A medical device including a sensing circuit configured to sense at least one cardiac electrical signal, a therapy delivery circuit configured to deliver cardiac pacing pulses, and a control circuit in communication with the sensing circuit and the therapy delivery circuit. The control circuit is configured to schedule a pending pacing pulse by starting a first pacing escape interval, receive a first cardiac signal segment from the at least one cardiac electrical signal sensed by the sensing circuit during the first pacing escape interval, determine tachyarrhythmia evidence in the first cardiac signal segment; and delay the pending pacing pulse scheduled at an expiration of the first pacing escape interval in response to determining the tachyarrhythmia evidence in at least the first cardiac signal segment.

Example 2. The medical device of example 1 wherein the sensing circuit is further configured to sense cardiac event signals from the at least one cardiac electrical signal and the control circuit is further configured to schedule the pending pacing pulse by starting the first pacing escape interval in response to the sensing circuit sensing a cardiac event signal.

Example 3. The medical device of example 1 wherein the control circuit is further configured to schedule the pending pacing pulse by starting the first pacing escape interval in response to the therapy delivery circuit delivering a cardiac pacing pulse.

Example 4. The medical device of any of examples 1-3 wherein the control circuit is further configured to delay the pending pacing pulse by restarting the first pacing escape interval.

Example 5. The medical device of any of examples 1-3 wherein the control circuit is further configured to delay the pending pacing pulse by starting a pacing delay interval different than the first pacing escape interval.

Example 6. The medical device of any of examples 1-5 wherein the control circuit is further configured to receive a plurality of cardiac signal segments including the first cardiac signal segment from the at least one cardiac electrical signal and determine tachyarrhythmia evidence in at least a threshold number of the plurality of cardiac signal segments. The control circuit may delay the pending pacing pulse in response to determining the tachyarrhythmia evidence in at least the threshold number of the plurality of cardiac signal segments.

Example 7. The medical device of any of examples 1-6 wherein the control circuit is further configured to determine the tachyarrhythmia evidence in the first cardiac signal segment by identifying signal pulse peaks from the first cardiac signal segment, determining peak intervals between the identified signal pulse peaks and determining that the peak intervals meet a tachyarrhythmia rate threshold.

Example 8. The medical device of any of examples 1-7 wherein the control circuit is further configured to determine the tachyarrhythmia evidence in the first cardiac signal segment by determining at least one of: a low slope content from the first cardiac signal segment; a spectral width from the first cardiac signal segment; or a mean period from the first cardiac signal segment. The control circuit may determine that at least one of the low slope content, the spectral width and/or the mean period meet tachyarrhythmia evidence criteria and determine the tachyarrhythmia evidence in the first cardiac signal segment in response to at least one of the low slope content, the spectral width and/or the mean period meeting the tachyarrhythmia evidence criteria.

Example 9. The medical device of any of examples 1-8 wherein the control circuit is further configured to determine the tachyarrhythmia evidence in the first cardiac signal segment by determining a spectral width from the cardiac signal segment and determining a mean period from the cardiac signal segment. The control circuit may determine that the mean period meets a first threshold and determine that a ratio of the spectral width and the mean period meets a second threshold. The control circuit may determine the tachyarrhythmia evidence in the first cardiac signal segment based on the mean period meeting the first threshold and the ratio of the spectral width and the mean period meeting the second threshold.

Example 10. The medical device of any of examples 1-9 wherein the control circuit is further configured to receive a second cardiac signal segment from the at least one cardiac electrical signal sensed by the sensing circuit after delaying the pending pacing pulse and determine no tachyarrhythmia evidence in the second cardiac signal segment. The therapy delivery circuit is further configured to deliver the delayed pending pacing pulse in response to the control circuit determining no tachyarrhythmia evidence in at least the second cardiac signal segment.

Example 11. The medical device of any of examples 1-10 wherein the control circuit is further configured to receive a second cardiac signal segment from the at least one cardiac electrical signal sensed by the sensing circuit, determine an amplitude metric from the second cardiac signal segment, determine that the amplitude metric is less than an amplitude threshold, and determine no tachyarrhythmia evidence in the second cardiac signal segment in response to the amplitude metric being less than the amplitude threshold. The therapy delivery circuit is further configured to deliver the delayed pending pacing pulse in response to the control circuit determining no tachyarrhythmia evidence in at least the second cardiac signal segment.

Example 12. The medical device of any of examples 1-11 wherein the control circuit is further configured to receive a second cardiac signal segment from the at least one cardiac electrical signal sensed by the sensing circuit, determine at least one noise metric from the second cardiac signal segment, and determine no tachyarrhythmia evidence in the second cardiac signal segment based on the at least one noise metric. The therapy delivery circuit is further configured to deliver the delayed pending pacing pulse in response to the control circuit determining no tachyarrhythmia evidence in at least the second cardiac signal segment.

Example 13. The medical device of example 12 wherein the control circuit is further configured to determine the at least one noise metric from the second cardiac signal segment by determining at least one of: a count of noise pulses in the second cardiac signal segment; a mean rectified amplitude of the second cardiac signal segment; a normalized mean rectified amplitude of the second cardiac signal segment; and/or a mean period of the second cardiac signal segment.

Example 14. The medical device of any of examples 1-13 wherein the control circuit is further configured to delay the pending pacing pulse by setting a first delay interval in response to determining tachyarrhythmia evidence in at least the first cardiac signal segment, receive a second cardiac signal segment from the at least one cardiac electrical signal sensed by the sensing circuit during the first delay interval, determine tachyarrhythmia evidence in the second cardiac signal segment, and delay the pending pacing pulse by setting a second delay interval in response to determining the tachyarrhythmia evidence in at least the second cardiac signal segment.

Example 15. The medical device of any of examples 1-14, wherein the therapy delivery circuit is further configured to deliver a plurality of pacing pulses, and the control circuit is further configured to start a plurality of pacing escape intervals comprising the first pacing escape interval, wherein each pacing escape interval of the plurality of pacing escape intervals is started in response to the therapy delivery circuit delivering a pacing pulse of the plurality of pacing pulses. The control circuit is configured to receive a plurality of cardiac signal segments comprising the first cardiac signal segment from the at least one cardiac electrical signal, wherein the plurality of cardiac signal segments are sensed by the sensing circuit during the plurality of pacing escape intervals. The control circuit is further configured to determine tachyarrhythmia evidence in the plurality of cardiac signal segments and delay the pending pacing pulse scheduled at the expiration of the first pacing escape interval in response to determining the tachyarrhythmia evidence in the plurality of cardiac signal segments.

Example 16. The medical device of any of examples 1-15 wherein the control circuit is further configured to determine that a maximum pacing delay of the pending pacing pulse is reached, and the therapy delivery circuit is configured to deliver the pending pacing pulse in response to the maximum pacing delay being reached.

Example 17. The medical device of any of examples 1-16 wherein the control circuit is further configured to determine the tachyarrhythmia evidence without detecting a tachyarrhythmia based on the first cardiac signal segment.

Example 18. The medical device of any of examples 1-17, wherein the control circuit is further configured to detect a tachyarrhythmia from the at least one cardiac electrical signal after delaying the pending pacing pulse and cancel the pending pacing pulse in response to detecting the tachyarrhythmia. The therapy delivery circuit may be further configured to deliver a tachyarrhythmia therapy in response to the control circuit detecting the tachyarrhythmia.

Example 19. A method comprising sensing at least one cardiac electrical signal, scheduling a pending pacing pulse by starting a first pacing escape interval, receiving a first cardiac signal segment from the at least one cardiac electrical signal sensed during the first pacing escape interval, determining tachyarrhythmia evidence in the first cardiac signal segment, and delaying the pending pacing pulse scheduled at an expiration of the first pacing escape interval in response to determining the tachyarrhythmia evidence in at least the first cardiac signal segment.

Example 20. The method of example 19 further comprising sensing cardiac event signals from the at least one cardiac electrical signal and scheduling the pending pacing pulse by starting the first pacing escape interval in response to sensing a cardiac event signal from the cardiac electrical signal.

Example 21. The method of example 19 further comprising delivering a cardiac pacing pulse and scheduling the pending pacing pulse by starting the first pacing escape interval in response delivering a cardiac pacing pulse.

Example 22. The method of any of examples 19-21 further comprising delaying the pending pacing pulse by restarting the first pacing escape interval.

Example 23. The method of any of examples 19-21 further comprising delaying the pending pacing pulse by starting a pacing delay interval different than the first pacing escape interval.

Example 24. The method of any of examples 19-23 further comprising receiving a plurality of cardiac signal segments including the first cardiac signal segment from the at least one cardiac electrical signal, determining tachyarrhythmia evidence in at least a threshold number of the plurality of cardiac signal segments, and delaying the pending pacing pulse in response to determining the tachyarrhythmia evidence in at least the threshold number of the plurality of cardiac signal segments.

Example 25. The method of any of examples 19-24 wherein determining the tachyarrhythmia evidence in the first cardiac signal segment comprises identifying signal pulse peaks from the first cardiac signal segment, determining peak intervals between the identified signal pulse peaks, and determining that the peak intervals meet a tachyarrhythmia rate threshold.

Example 26. The method of any of examples 19-25 wherein determining the tachyarrhythmia evidence in the first cardiac signal segment comprises determining at least one of: a low slope content from the first cardiac signal segment; a spectral width from the first cardiac signal segment; and a mean period from the first cardiac signal segment. The method may further include determining that at least one of the low slope content, the spectral width and/or the mean period meet tachyarrhythmia evidence criteria; and determining the tachyarrhythmia evidence in the first cardiac signal segment in response to at least one of the low slope content, the spectral width and/or the mean period meeting the tachyarrhythmia evidence criteria.

Example 27. The method of any of examples 19-26 wherein determining the tachyarrhythmia evidence in the first cardiac signal segment comprises determining a spectral width from the cardiac signal segment and determining a mean period from the cardiac signal segment. The method may include determining that the mean period meets a first threshold, determining that a ratio of the spectral width and the mean period meets a second threshold and determining the tachyarrhythmia evidence in the first cardiac signal segment based on the mean period meeting the first threshold and the ratio of the spectral width and the mean period meeting the second threshold.

Example 28. The method of any of examples 19-27 further comprising: receiving a second cardiac signal segment from the at least one cardiac electrical signal sensed after delaying the pending pacing pulse, determining no tachyarrhythmia evidence in the second cardiac signal segment, and delivering the delayed pending pacing pulse in response to determining no tachyarrhythmia evidence in at least the second cardiac signal segment.

Example 29. The method of any of examples 19-28 further comprising, receiving a second cardiac signal segment from the at least one cardiac electrical signal, determining an amplitude metric from the second cardiac signal segment, determining that the amplitude metric is less than an amplitude threshold, and determining no tachyarrhythmia evidence in the second cardiac signal segment in response to the amplitude metric being less than the amplitude threshold. The method may further include delivering the delayed pending pacing pulse in response to determining no tachyarrhythmia evidence in at least the second cardiac signal segment.

Example 30. The method of any of examples 19-29 further comprising receiving a second cardiac signal segment from the at least one cardiac electrical signal, determining at least one noise metric from the second cardiac signal segment, determining no tachyarrhythmia evidence in second cardiac signal segment based on the at least one noise metric, and delivering the delayed pending pacing pulse in response to determining no tachyarrhythmia evidence in at least the second cardiac signal segment.

Example 31. The method of example 30 wherein determining the at least one noise metric from the second cardiac signal segment comprises determining at least one of: a count of noise pulses in the second cardiac signal segment; a mean rectified amplitude of the second cardiac signal segment; a normalized mean rectified amplitude of the second cardiac signal segment; and/or a mean period of the second cardiac signal segment.

Example 32. The method of any of examples 19-31 further comprising delaying the pending pacing pulse by setting a first delay interval in response to the determining tachyarrhythmia evidence in at least the first cardiac signal segment, receiving a second cardiac signal segment from the at least one cardiac electrical signal sensed during the first delay interval, determining tachyarrhythmia evidence in the second cardiac signal segment, and delaying the pending pacing pulse by setting a second delay interval in response to determining the tachyarrhythmia evidence in at least the second cardiac signal segment.

Example 33. The method of any of examples 19-32 further comprising delivering a plurality of pacing pulses, starting a plurality of pacing escape intervals comprising the first pacing escape interval, wherein each pacing escape interval of the plurality of pacing escape intervals is started in response to a delivered pacing pulse of the plurality of pacing pulses. The method may further include receiving a plurality of cardiac signal segments comprising the first cardiac signal segment from the at least one cardiac electrical signal, wherein the plurality of cardiac signal segments are sensed during the plurality of pacing escape intervals. The method may further include determining tachyarrhythmia evidence in the plurality of cardiac signal segments and delaying the pending pacing pulse scheduled at the expiration of the first pacing escape interval in response to determining the tachyarrhythmia evidence in the plurality of cardiac signal segments.

Example 34. The method of any of examples 19-33 further comprising determining that a maximum pacing delay of the pending pacing pulse is reached and delivering the pending pacing pulse in response to the maximum pacing delay being reached.

Example 35. The method of any of examples 19-34 further comprising determining the tachyarrhythmia evidence without detecting a tachyarrhythmia based on the first cardiac signal segment.

Example 36. The method of any of examples 19-35 further comprising detecting a tachyarrhythmia from the at least one cardiac electrical signal after delaying the pending pacing pulse, cancelling the pending pacing pulse in response to detecting the tachyarrhythmia, and delivering a tachyarrhythmia therapy in response to detecting the tachyarrhythmia.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a sensing circuit configured to sense at least one cardiac electrical signal;
a therapy delivery circuit configured to deliver cardiac pacing pulses; and
a control circuit in communication with the sensing circuit and the therapy delivery circuit, the control circuit configured to:
schedule a pending pacing pulse of the cardiac pacing pulses by starting a first pacing escape interval;
receive a first cardiac signal segment from the at least one cardiac electrical signal sensed by the sensing circuit during the first pacing escape interval;
determine tachyarrhythmia evidence in the first cardiac signal segment by determining at least one tachyarrhythmia morphology metric from the first cardiac signal segment; and
delay the pending pacing pulse scheduled at an expiration of the first pacing escape interval in response to determining the tachyarrhythmia evidence in at least the first cardiac signal segment.

2. The medical device of claim 1, wherein:
the sensing circuit is further configured to sense cardiac event signals from the at least one cardiac electrical signal;
the control circuit is further configured to schedule the pending pacing pulse by starting the first pacing escape interval in response to the sensing circuit sensing a cardiac event signal.

3. The medical device of claim 1, wherein the control circuit is further configured to schedule the pending pacing pulse by starting the first pacing escape interval in response to the therapy delivery circuit delivering a cardiac pacing pulse.

4. The medical device of claim 1, wherein the control circuit is further configured to delay the pending pacing pulse by restarting the first pacing escape interval.

5. The medical device of claim 1, wherein the control circuit is further configured to delay the pending pacing pulse by starting a pacing delay interval different than the first pacing escape interval.

6. The medical device of claim 1, wherein the control circuit is further configured to:
receive a plurality of cardiac signal segments including the first cardiac signal segment from the at least one cardiac electrical signal;
determine tachyarrhythmia evidence in at least a threshold number of the plurality of cardiac signal segments; and
delay the pending pacing pulse in response to determining the tachyarrhythmia evidence in at least the threshold number of the plurality of cardiac signal segments.

7. The medical device of claim 1, wherein the control circuit is further configured to determine the tachyarrhythmia evidence in the first cardiac signal segment by:
identifying signal pulse peaks from the first cardiac signal segment;
determining peak intervals between the identified signal pulse peaks; and
determining that the peak intervals meet a tachyarrhythmia rate threshold.

8. The medical device of claim 1, wherein the control circuit is further configured to determine the tachyarrhythmia evidence in the first cardiac signal segment by:
determining at least one of:
a low slope content from the first cardiac signal segment;
a spectral width from the first cardiac signal segment; and
a mean period from the first cardiac signal segment;
determining that at least one of the low slope content, the spectral width and the mean period meet tachyarrhythmia evidence criteria; and
determining the tachyarrhythmia evidence in the first cardiac signal segment in response to the at least one of the low slope content, the spectral width and the mean period meeting the tachyarrhythmia evidence criteria.

9. The medical device of claim 1, wherein the control circuit is further configured to determine the tachyarrhythmia evidence in the first cardiac signal segment by:
determining a spectral width from the cardiac signal segment;
determining a mean period from the cardiac signal segment;
determining that the mean period meets a first threshold;
determining that a ratio of the spectral width and the mean period meets a second threshold; and
determining the tachyarrhythmia evidence in the first cardiac signal segment based on the mean period meeting the first threshold and the ratio of the spectral width and the mean period meeting the second threshold.

10. The medical device of claim 1, wherein:
the control circuit is further configured to:
receive a second cardiac signal segment from the at least one cardiac electrical signal sensed by the sensing circuit after delaying the pending pacing pulse; and
determine no tachyarrhythmia evidence in the second cardiac signal segment; and
the therapy delivery circuit is further configured to deliver the delayed pending pacing pulse in response to the control circuit determining no tachyarrhythmia evidence in at least the second cardiac signal segment.

11. The medical device of claim 1, wherein:

the control circuit is further configured to:

receive a second cardiac signal segment from the at least one cardiac electrical signal sensed by the sensing circuit;

determine an amplitude metric from the second cardiac signal segment;

determine that the amplitude metric is less than an amplitude threshold; and determine no tachyarrhythmia evidence in the second cardiac signal segment in response to the amplitude metric being less than the amplitude threshold; and the therapy delivery circuit is further configured to deliver the delayed pending pacing pulse in response to the control circuit determining no tachyarrhythmia evidence in at least the second cardiac signal segment.

12. The medical device of claim 1, wherein:

the control circuit is further configured to:

receive a second cardiac signal segment from the at least one cardiac electrical signal sensed by the sensing circuit;

determine at least one noise metric from the second cardiac signal segment; and determine no tachyarrhythmia evidence in the second cardiac signal segment based on the at least one noise metric; and the therapy delivery circuit is further configured to deliver the delayed pending pacing pulse in response to the control circuit determining no tachyarrhythmia evidence in at least the second cardiac signal segment.

13. The medical device of claim 1, wherein the control circuit is further configured to:

delay the pending pacing pulse by setting a first delay interval in response to determining tachyarrhythmia evidence in at least the first cardiac signal segment;

receive a second cardiac signal segment from the at least one cardiac electrical signal sensed by the sensing circuit during the first delay interval;

determine tachyarrhythmia evidence in the second cardiac signal segment; and delay the pending pacing pulse by setting a second delay interval in response to determining the tachyarrhythmia evidence in at least the second cardiac signal segment.

14. The medical device of claim 1, wherein:

the therapy delivery circuit is further configured to deliver a plurality of pacing pulses; and the control circuit is further configured to:

start a plurality of pacing escape intervals comprising the first pacing escape interval, wherein each pacing escape interval of the plurality of pacing escape intervals is started in response to the therapy delivery circuit delivering a pacing pulse of the plurality of pacing pulses;

receive a plurality of cardiac signal segments comprising the first cardiac signal segment from the at least one cardiac electrical signal, wherein the plurality of cardiac signal segments are sensed by the sensing circuit during the plurality of pacing escape intervals;

determine tachyarrhythmia evidence in the plurality of cardiac signal segments; and delay the pending pacing pulse scheduled at the expiration of the first pacing escape interval in response to determining the tachyarrhythmia evidence in the plurality of cardiac signal segments.

15. The medical device claim 1, wherein:

the control circuit is further configured to determine that a maximum pacing delay of the pending pacing pulse is reached; and the therapy delivery circuit is configured to deliver the pending pacing pulse in response to the maximum pacing delay being reached.

16. The medical device of claim 1, wherein the control circuit is further configured to determine the tachyarrhythmia evidence without detecting a tachyarrhythmia based on the first cardiac signal segment.

17. The medical device of claim 1, wherein:

the control circuit is further configured to:

detect a tachyarrhythmia from the at least one cardiac electrical signal after delaying the pending pacing pulse; and cancel the pending pacing pulse in response to detecting the tachyarrhythmia; and the therapy delivery circuit is further configured to deliver a tachyarrhythmia therapy in response to the control circuit detecting the tachyarrhythmia.

18. A method comprising:

sensing at least one cardiac electrical signal;

scheduling a pending pacing pulse for delivery by a therapy delivery circuit by starting a first pacing escape interval;

receiving a first cardiac signal segment from the at least one cardiac electrical signal sensed during the first pacing escape interval;

determining tachyarrhythmia evidence in the first cardiac signal segment by determining at least one tachyarrhythmia morphology metric from the first cardiac signal segment; and controlling the therapy delivery circuit to delay the pending pacing pulse scheduled at an expiration of the first pacing escape interval in response to determining the tachyarrhythmia evidence in at least the first cardiac signal segment.

19. The method of claim 18, further comprising:

sensing cardiac event signals from the at least one cardiac electrical signal; and scheduling the pending pacing pulse by starting the first pacing escape interval in response to sensing a cardiac event signal from the cardiac electrical signal.

20. The method of claim 18, further comprising:

delivering a cardiac pacing pulse; and scheduling the pending pacing pulse by starting the first pacing escape interval in response to delivering the cardiac pacing pulse.

21. The method of claim 18, further comprising delaying the pending pacing pulse by restarting the first pacing escape interval.

22. The method of claim 18, further comprising delaying the pending pacing pulse by starting a pacing delay interval different than the first pacing escape interval.

23. The method of claim 18, further comprising:

receiving a plurality of cardiac signal segments including the first cardiac signal segment from the at least one cardiac electrical signal;

determining tachyarrhythmia evidence in at least a threshold number of the plurality of cardiac signal segments; and delaying the pending pacing pulse in response to determining the tachyarrhythmia evidence in at least the threshold number of the plurality of cardiac signal segments.

24. The method of claim 18, wherein determining the tachyarrhythmia evidence in the first cardiac signal segment comprises:

identifying signal pulse peaks from the first cardiac signal segment;

determining peak intervals between the identified signal pulse peaks; and determining that the peak intervals meet a tachyarrhythmia rate threshold.

25. The method of claim 18, wherein determining the tachyarrhythmia evidence in the first cardiac signal segment comprises:

determining at least one of:

a low slope content from the first cardiac signal segment;

a spectral width from the first cardiac signal segment; and a mean period from the first cardiac signal segment;

determining that at least one of the low slope content, the spectral width and the mean period meet tachyarrhythmia evidence criteria; and determining the tachyarrhythmia evidence in the first cardiac signal segment in response to the at least one of the low slope content, the spectral width and the mean period meeting the tachyarrhythmia evidence criteria.

26. The method of claim 18, wherein determining the tachyarrhythmia evidence in the first cardiac signal segment comprises:

determining a spectral width from the cardiac signal segment;

determining a mean period from the cardiac signal segment;

determining that the mean period meets a first threshold;

determining that a ratio of the spectral width and the mean period meets a second threshold; and determining the tachyarrhythmia evidence in the first cardiac signal segment based on the mean period meeting the first threshold and the ratio of the spectral width and the mean period meeting the second threshold.

27. The method of claim 18, further comprising:

receiving a second cardiac signal segment from the at least one cardiac electrical signal sensed after delaying the pending pacing pulse;

determining no tachyarrhythmia evidence in the second cardiac signal segment; and delivering the delayed pending pacing pulse in response to determining no tachyarrhythmia evidence in at least the second cardiac signal segment.

28. The method of claim 18, further comprising:

receiving a second cardiac signal segment from the at least one cardiac electrical signal;

determining an amplitude metric from the second cardiac signal segment;

determining that the amplitude metric is less than an amplitude threshold; and determining no tachyarrhythmia evidence in the second cardiac signal segment in response to the amplitude metric being less than the amplitude threshold; and delivering the delayed pending pacing pulse in response to determining no tachyarrhythmia evidence in at least the second cardiac signal segment.

29. The method of claim 18, further comprising:

receiving a second cardiac signal segment from the at least one cardiac electrical signal;

determining at least one noise metric from the second cardiac signal segment;

determining no tachyarrhythmia evidence in second cardiac signal segment based on the at least one noise metric; and delivering the delayed pending pacing pulse in response to determining no tachyarrhythmia evidence in at least the second cardiac signal segment.

30. The method of claim 18, further comprising:

delaying the pending pacing pulse by setting a first delay interval in response to the determining tachyarrhythmia evidence in at least the first cardiac signal segment;

receiving a second cardiac signal segment from the at least one cardiac electrical signal sensed during the first delay interval;

determining tachyarrhythmia evidence in the second cardiac signal segment; and delaying the pending pacing pulse by setting a second delay interval in response to determining the tachyarrhythmia evidence in at least the second cardiac signal segment.

31. The method of claim 18, further comprising:

delivering a plurality of pacing pulses;

starting a plurality of pacing escape intervals comprising the first pacing escape interval, wherein each pacing escape interval of the plurality of pacing escape intervals is started in response to a delivered pacing pulse of the plurality of pacing pulses;

receiving a plurality of cardiac signal segments comprising the first cardiac signal segment from the at least one cardiac electrical signal, wherein the plurality of cardiac signal segments are sensed during the plurality of pacing escape intervals;

determining tachyarrhythmia evidence in the plurality of cardiac signal segments; and delaying the pending pacing pulse scheduled at the expiration of the first pacing escape interval in response to determining the tachyarrhythmia evidence in the plurality of cardiac signal segments.

32. The method of claim 18, further comprising:

determining that a maximum pacing delay of the pending pacing pulse is reached; and delivering the pending pacing pulse in response to the maximum pacing delay being reached.

33. The method of claim 18, further comprising determining the tachyarrhythmia evidence without detecting a tachyarrhythmia based on the first cardiac signal segment.

34. The method of claim 18, further comprising:

detecting a tachyarrhythmia from the at least one cardiac electrical signal after delaying the pending pacing pulse;

cancelling the pending pacing pulse in response to detecting the tachyarrhythmia; and delivering a tachyarrhythmia therapy in response to detecting the tachyarrhythmia.

35. A non-transitory, computer readable medium storing a set of instructions that, when executed by a control circuit of a medical device having a therapy delivery circuit, cause the medical device to:

sense at least one cardiac electrical signal;

schedule a pending pacing pulse for delivery by the therapy delivery circuit by starting a pacing escape interval;

receive a cardiac signal segment from the at least one cardiac electrical signal sensed during the pacing escape interval;

determine tachyarrhythmia evidence in the cardiac signal segment by determining a at least one tachyarrhythmia morphology metric from the first cardiac signal segment; and delay the pending pacing pulse scheduled for delivery by the therapy delivery circuit at an expiration of the pacing escape interval in response to determining the tachyarrhythmia evidence in at least the cardiac signal segment.

* * * * *